United States Patent
Dzubay et al.

(10) Patent No.: US 10,845,373 B2
(45) Date of Patent: Nov. 24, 2020

(54) FLUOROGENIC PH SENSITIVE DYES AND THEIR METHOD OF USE

(71) Applicant: LIFE TECHNOLOGIES CORPORATION, Carlsbad, CA (US)

(72) Inventors: Jeffrey Dzubay, Bend, OR (US); Kyle Gee, Springfield, OR (US); Vladimir Martin, Eugene, OR (US); Aleksey Rukavishnikov, Eugene, OR (US); Daniel Beacham, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/899,021

(22) Filed: Feb. 19, 2018

(65) Prior Publication Data

US 2018/0238912 A1    Aug. 23, 2018

Related U.S. Application Data

(60) Division of application No. 14/937,736, filed on Nov. 10, 2015, now Pat. No. 9,939,454, which is a continuation of application No. 13/614,995, filed on Sep. 13, 2012, now abandoned, which is a continuation of application No. 11/927,588, filed on Oct. 29, 2007, now abandoned.

(60) Provisional application No. 60/940,323, filed on May 25, 2007, provisional application No. 60/863,318, filed on Oct. 27, 2006.

(51) Int. Cl.
| | |
|---|---|
| G01N 33/84 | (2006.01) |
| G01N 33/58 | (2006.01) |
| C07D 311/82 | (2006.01) |
| C07D 311/90 | (2006.01) |
| C07D 405/12 | (2006.01) |
| C07D 413/04 | (2006.01) |
| C07D 491/22 | (2006.01) |
| C07D 209/14 | (2006.01) |
| C09K 11/06 | (2006.01) |
| C07F 5/02 | (2006.01) |
| C07K 1/13 | (2006.01) |
| C09B 7/00 | (2006.01) |
| C09B 11/12 | (2006.01) |
| C09B 11/28 | (2006.01) |
| C09B 57/00 | (2006.01) |
| C09B 69/00 | (2006.01) |
| G01N 31/22 | (2006.01) |
| G01N 33/50 | (2006.01) |
| C09B 11/24 | (2006.01) |
| G01N 33/80 | (2006.01) |

(52) U.S. Cl.
CPC ........... *G01N 33/84* (2013.01); *C07D 209/14* (2013.01); *C07D 311/82* (2013.01); *C07D 311/90* (2013.01); *C07D 405/12* (2013.01); *C07D 413/04* (2013.01); *C07D 491/22* (2013.01); *C07F 5/02* (2013.01); *C07K 1/13* (2013.01); *C09B 7/00* (2013.01); *C09B 11/12* (2013.01); *C09B 11/24* (2013.01); *C09B 11/28* (2013.01); *C09B 57/00* (2013.01); *C09B 69/00* (2013.01); *C09K 11/06* (2013.01); *G01N 31/22* (2013.01); *G01N 33/5005* (2013.01); *G01N 33/5058* (2013.01); *G01N 33/5091* (2013.01); *G01N 33/582* (2013.01); *G01N 33/80* (2013.01); *G01N 2333/245* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 1,885,591 | A | 11/1932 | Coulthard et al. |
| 4,057,530 | A | 11/1977 | Pigerol et al. |
| 4,603,209 | A | 7/1986 | Tsien et al. |

(Continued)

FOREIGN PATENT DOCUMENTS

| | | |
|---|---|---|
| CN | 1660783 A | 8/2005 |
| EP | 0343560 A2 | 11/1989 |

(Continued)

OTHER PUBLICATIONS

Lefevre et al., "Texas Red-X and Rhodamine Red-X, New Derivatives of Sulforhodamine 101 and Lissamine Rhodamine B with Improved Labeling and Fluorescence Properties", Bioconjugate Chemistry, vol. 7, pp. 482-489). (Year: 1996).*

(Continued)

*Primary Examiner* — Michelle F. Paguio Frising

(57) ABSTRACT

A new class of pH sensitive fluorescent dyes and assays relating thereto are described. The dyes and assays are particularly suited for biological applications including phagocytosis and monitoring intracellular processes. The pH sensitive fluorescent dyes of the present invention include compounds of Formula I:

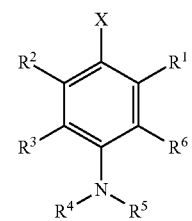

wherein the variables are described throughout the application.

8 Claims, 18 Drawing Sheets

(56) References Cited

U.S. PATENT DOCUMENTS

| | | |
|---|---|---|
| 4,711,955 A | 12/1987 | Ward et al. |
| 4,774,339 A | 9/1988 | Haugland et al. |
| 4,810,636 A | 3/1989 | Corey |
| 4,812,409 A | 3/1989 | Babb et al. |
| 4,849,362 A | 7/1989 | Demarinis et al. |
| 4,945,171 A | 7/1990 | Haugland et al. |
| 5,047,519 A | 9/1991 | Hobbs, Jr. et al. |
| 5,049,673 A | 9/1991 | Tsien et al. |
| 5,132,432 A | 7/1992 | Haugland et al. |
| 5,187,288 A | 2/1993 | Kang et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,352,803 A | 10/1994 | Mattingly |
| 5,362,628 A | 11/1994 | Haugland et al. |
| 5,405,975 A | 4/1995 | Kuhn et al. |
| 5,433,896 A | 7/1995 | Kang et al. |
| 5,442,045 A | 8/1995 | Haugland et al. |
| 5,451,343 A | 9/1995 | Neckers et al. |
| 5,453,517 A | 9/1995 | Kuhn et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,573,904 A | 11/1996 | Mattingly |
| 5,627,027 A | 5/1997 | Waggoner |
| 5,648,270 A | 7/1997 | Kuhn et al. |
| 5,696,157 A | 12/1997 | Wang et al. |
| 5,714,327 A | 2/1998 | Houthoff et al. |
| 5,773,227 A | 6/1998 | Kuhn et al. |
| 5,798,276 A | 8/1998 | Haugland et al. |
| 5,830,912 A | 11/1998 | Gee et al. |
| 5,846,737 A | 12/1998 | Kang |
| 5,847,162 A | 12/1998 | Lee et al. |
| 6,017,712 A | 1/2000 | Lee et al. |
| 6,025,505 A | 2/2000 | Lee et al. |
| 6,048,982 A | 4/2000 | Waggoner |
| 6,080,852 A | 6/2000 | Lee et al. |
| 6,130,101 A | 10/2000 | Mao et al. |
| 6,162,931 A | 12/2000 | Gee et al. |
| 6,201,134 B1 | 3/2001 | Nagano et al. |
| 6,229,055 B1 | 5/2001 | Klaubert et al. |
| 6,339,392 B1 | 1/2002 | Ashihara |
| 6,348,599 B1 | 2/2002 | Cummins et al. |
| 6,403,807 B1 | 6/2002 | Singh et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,756,231 B1 | 6/2004 | Nagano et al. |
| 6,833,386 B2 | 12/2004 | Nagano et al. |
| 6,974,873 B2 | 12/2005 | Leung et al. |
| 6,977,305 B2 | 12/2005 | Leung et al. |
| 7,005,518 B2 | 2/2006 | Peng et al. |
| 7,102,005 B2 | 9/2006 | Agnew et al. |
| 7,524,974 B2 | 4/2009 | Nagano et al. |
| 9,910,051 B2 | 3/2018 | Beacham et al. |
| 9,939,454 B2 | 4/2018 | Dzubay et al. |
| 2004/0038306 A1 | 2/2004 | Agnew et al. |
| 2004/0229852 A1 | 11/2004 | Lin et al. |
| 2006/0051874 A1 | 3/2006 | Reed et al. |
| 2007/0238884 A1* | 10/2007 | Smith ............ C09B 11/28 549/224 |
| 2008/0249321 A1 | 10/2008 | Nagano et al. |
| 2008/0274907 A1 | 11/2008 | Beacham et al. |
| 2013/0102021 A1 | 4/2013 | Beacham et al. |
| 2015/0037834 A1 | 2/2015 | Beacham et al. |

FOREIGN PATENT DOCUMENTS

| | | |
|---|---|---|
| EP | 0424261 A1 | 4/1991 |
| EP | 2064290 B1 | 10/2013 |
| EP | 2727965 | 3/2019 |
| ES | 2116229 A1 | 7/1998 |
| FR | 1391547 A | 3/1965 |
| JP | S5116659 A | 2/1976 |
| JP | S53124257 A | 10/1978 |
| JP | S62216792 A | 9/1987 |
| JP | H011611062 A | 6/1989 |
| JP | H05155870 A | 6/1993 |
| JP | H0666802 A | 3/1994 |
| JP | 2004339220 A | 12/2004 |
| JP | 2005539243 A | 12/2005 |
| JP | 2006233110 A | 9/2006 |
| JP | 2006521290 A | 9/2006 |
| JP | 2010508295 A | 3/2010 |
| WO | WO-9739064 A1 | 10/1997 |
| WO | WO-2004025259 A2 | 3/2004 |
| WO | WO-2004042347 A2 | 5/2004 |
| WO | WO-2005013966 A1 | 2/2005 |
| WO | WO-2005085811 A1 | 9/2005 |
| WO | WO-2005098437 A2 | 10/2005 |
| WO | WO-2008076524 A2 | 6/2008 |
| WO | WO-2008076524 A3 | 10/2008 |

OTHER PUBLICATIONS

Bajorek et al., "Fluorescence Probes Based on 9-Acridyl Derivatives of Aromatic Amines for Monitoring Free-Radical Polymerization", University of Technology and Agriculture, Faculty of Chemical Technology and Engineering, Journal of Polymer Science: Part A: Polymer Chemistry, vol. 40, 2002, pp. 3481-3488.

Bouizar, et al., "Purification and Characterization of Calcitonin Receptors in Rat Kidney Membranes by Covalent Cross-Linking Techniques", European Journal of Biochemistry, vol. 155, No. 1, 1986, 141-147.

Braun et al., "Direct measurement of cytosolic calcium and pH in living Chlamydomonas reinhardtii cells", European Journal of Cell Biology, vol. 78, Mar. 1999, 199-208.

Brinkley, "A Brief Survey of Methods for Preparing Protein Conjugates with Dyes, Haptens, and Cross-Linking Reagents", Bioconjugate Chemistry. vol. 3, No. 1, 1992, 2-13.

Browning, et al., "Studies on the Differing Effects of the Tumor Necrosis Factor and Lymphotoxin on the Growth of Several Human Tumor Lines", Journal of Immunology, vol. 143, No. 6, 1989, 1859-1867.

El-Shishtawy, et al., "A new Vilsmeier-type reaction for one-pot synthesis of pH sensitive fluroscnet cyaninie dyes.", Tetrahedron, vol. 62, No. 33, Aug. 14, 2006, 7793-7798.

EP13187570, "Extended European Search Report", dated Apr. 8, 2014. dated Apr. 8, 2014, 1-6.

Extended European Search Report for Application No. 07871255.1, dated Sep. 7, 2011, 6 pages.

Fiala, "Ineffective Phagocytosis of Amyloid-Beta by Macrophages of Alzheimer's Disease Patients", Journal of Alzheimer's Disease vol. 7, 2005, 221-232.

Haugland, Richard P., "Molecular Probes Handbook of Fluorescent Probes and Research Products", Ninth Edition, CD ROM, Table of Contents, Molecular Probes, Inc., 2002, 1-6.

Herbich, et al., "Electronic Structure and Molecular Conformation in the Excited Charge Transfer Singlets States of 9-Acridyl and Other Aryl Derivatives of Aromatic Amines", Journal of American Chemistry. vol. 120, 1998, 1014-1029.

Hyrc, et al., "Ion Selectivity of low affinity ratiometric calcium indicators : mag-Fura-2, Fura-2FF and BTC", Cell Calcium, vol. 27, No. 2, 2000, 75-86.

Intl Application No. PCT/US2007/082617, International Preliminary Report on Patentability dated Apr. 28, 2009, 1-12.

Intl PCT/US2007/082617, "International Search Report and Written Opinion", dated Aug. 7, 2008, 1-18.

Johnson, Invitation to Organic Chemistry, Jone & Barlett Learning,1999, 24.

Jung, et al., "Crosslinking of platelet glycoprotein lb by N-succinimidyl (4-azidophenyldithio)propionate and 3,3'-dithiobis(sulfosucininnidyl propionate)", Biochimica et Bioohvsica Acta vol. 761, No. 2, 1983, 152-162.

(56) References Cited

OTHER PUBLICATIONS

Kirpichenok, L.K. et al., "Photochemical reactions of 7-aminocoumarins 1. [2+2]-cycloadducts with vinyl buytl ether and acrylonitrile", Chemisty of Heterocycllic Compounds, vol. 24, No. 9, 1988, 959-965.

Kojima, et al., "Bioimaging of Nitric Oxide with Fluorescent Indicators Based on the Rhodamine Chromophore", Analytical Chemistry, vol. 73, No. 9, May 1, 2001, 1967-1973.

Martinez-Zaguilan, et al., "Selection of fluorescent ion indicators for simultaneous measurements of pH and Ca2+", Cell Calcium, vol. 19, No. 4, 1996, 337-349.

Oliver, A. et al., "Effects of Temperature on Calcium-Sensitive Fluorescent Probes", Biophysical Journal, vol. 78, 2000, pp. 2116-2126.

Oszczapowicz et al., "Amidines. Part 40. Amidine-Deuteriochloroform Complexes. Influence of Amidine Basicity on the Frequency of C-D Stretching Vibrations", Journal of the Chemical Society, Perkins Translations 2, 2000, 2343-2346.

Park, et al., "Characterization of the Cell Surface Receptor for a Multi-Lineage Colony-Stimulating Factor (CSF-2alpha)*", Journal of Biological Chemistry, vol. 261, No. 1, 1986, 205-210.

Raju, B. et al., "A Fluorescent Indicator for Measuring Cytosolic Free Magnesium" American Journal of Physiology, Laboratory of Molecular Biophysics, National Institute of Environmental Health Sciences, 1989, C540-0548.

Scott, et al., "Analysis of the uptake of the fluorescent marker 2', 7'-bis-(2 carboxyethyl1)-5(and 6)-carboxyfluorescin (BCECF) by hydro genosomes in Trichomonas vaginalis", European Journal of Cell Biology, vol. 76, 1998, 139-145.

Joshi, S. et al., "ATP Synthase complex from Bovine Heart Mitochondria. Subunit Arrangements as Revealed by Nearest Analysis and Susceptibility to Trypsin", The Journal of Biological Chemistry vol. 265, No. 24 1990, 14518-14525.

Wan et al., "A rapid and simple microfluorometric phagocytosis assay", Journal of Immunological Methods 1993, vol. 162, pp. 1-7.

Yoshida, Katsuhira et al., "Heterocyclic quinol-type fluorophores. Part 2. Solid-state fluorescence enhancement behaviour of benzofurano[3,2-b]-naphthoquinol-type naphthoquinol-typoThe IUPAC name for the parent benzofurano[3,2-b]naphthoquinone is naphtho[2,3-b]benzofuran-6, 11-dione", Journal of the Chemical Society, Perkin Transactions 2., No. 3, 2002, 708-714.

Zarling, et al., "Mapping of Lymphocyte Surface Polypeptide Antigens by Chemical Cross-Linking with BSOCOES", Journal of Immunolooy. vol. 124, No. 2, 1980, 913-920.

Zhang, Laura , "Curcuminoids enhance amyloid-beta uptake by macrophages of Alzheimer's disease patients", Journel of Alzheimer's Disease, vol. 10, 2006, 1-7.

\* cited by examiner

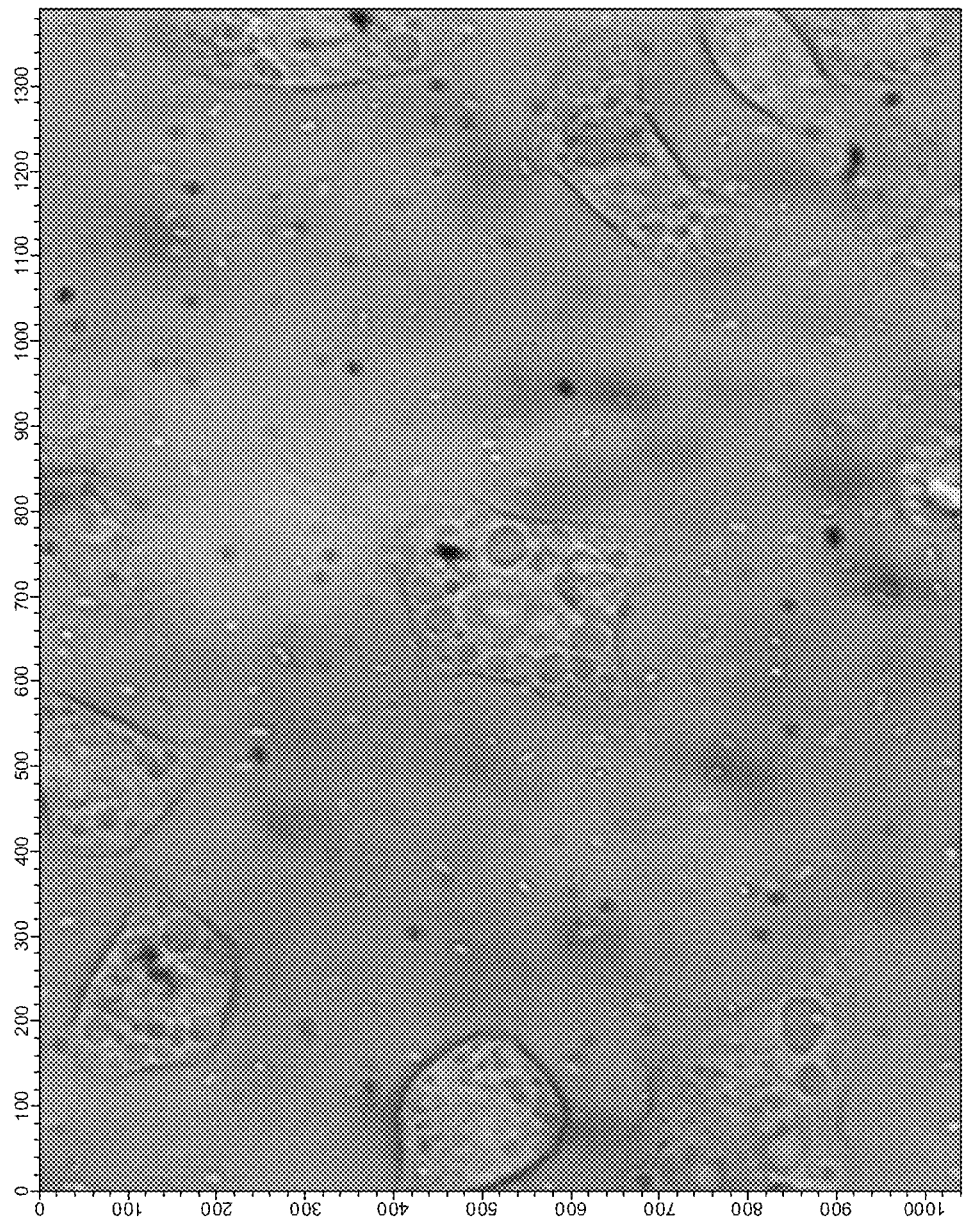

FLUOROGENIC PH SENSITIVE DYES AND THEIR METHOD OF USE

CROSS-REFERENCE TO RELATED APPLICATIONS

This application is a Divisional of U.S. Non-Provisional Ser. No. 14/937,736 filed Nov. 10, 2015, which is a Continuation of U.S. Non-Provisional Ser. No. 13/614,995 filed Sep. 13, 2012, now abandoned, which is a Continuation of U.S. Non-Provisional Ser. No. 11/927,588, filed Oct. 29, 2007, now abandoned, which claims the benefit of Provisional Application Nos. 60/863,318, filed 27 Oct. 2006 and 60/940,323, filed 25 May 2007, all of which are incorporated by reference in their entireties.

FIELD OF THE INVENTION

Novel pH sensitive fluorescent dyes and assays for use in a variety of applications including monitoring of intracellular processes are disclosed.

BACKGROUND OF THE INVENTION pH sensitive fluorescent dyes employed in biological research and medical diagnostics belong to two groups, each distinguished by the origin of fluorescent responses to changes in pH. The first group includes compounds having fluorescence controlled by the ionization of phenolic hydroxyl groups in a fluorophore. Examples include fluorescein, carboxyfluorescein, Oregon Green®, SNARF®, SNAFL®, and HPTS indicators.

U.S. Patent Publication No. 2006/0051874 (M. W. Reed, et al) describes fluorescein-like structures incorporated into a fluorescent detector for monitoring pH of the blood in bank storages. Because the degree of ionization of these type molecules increase upon lowering the acidity of the environment, they become more fluorescent as pH increases.

Fluorescent pH sensors of the second group include an amino group (aliphatic or aromatic) as an indicator moiety along with a reporter fluorescent dye moiety. When such a molecule adsorbs a photon, creating an excited electronic state, the electron of the amino group's unshared pair transfers to the orbital vacated by excitation. Such an electron transfer, referred to as Photoinduced Electron Transfer (PET) prevents the excited molecule from emission transition, thus the fluorescence of the dye is quenched. Protonation of the amino group changes the nature and energy of the pair's orbital and stops the PET. As a result, the fluorescent reporter moiety responds to a pH change. Because protonation of the amino group cancels the quenching, the PET-based sensors become more fluorescent as pH decreases.

Examples of PET-based pH sensors include LysoSensor dyes, which contain dimethylamino group as an indicator moiety and CypHer® 5E dye having an indolenine indicator group. One disadvantage of these sensors is that the working range is shifted to the acidic side because of the low pKa of the indicator amino group.

A family of rhodamine-based pH sensors are described in WO 2005/098437. The dyes have a benzene ring substituted ortho to the xanthene moiety by —OH or —SH (or their deprotonated forms) and WO 2005/098437 states that the —OH or —SH is believed responsible for the pH response of the dye. These dyes display a pH-dependency similar to amine PET indicators but were designed to have pKa values of less than 6 based on a perceived need for a pH sensor that would target cell compartments with a pH of less than 6. The WO 2005/098437 application purports that the strong electron withdrawing properties of the tetramethylrhodamine moiety in the dyes, significantly decreases the pKa of the indicator group, thus shifting sensors' working range toward highly acidic pH values. However, this thereby limits the applicability of the dyes described in WO 2005/098 at a physiological pH (e.g pH 6-7), especially in biological systems. These prior art compounds have been found by us to have potentially inconvenient instability in solution.

Accordingly, there is a need for additional pH sensitive fluorescent dyes, advantageously with improved properties, including in at least some compounds the ability to detect pH changes in biological systems. It is an object of the present invention to develop a novel class of fluorescent pH sensors, desirably mitigating or removing the disadvantages of the compounds known in art. Particularly, it is an object of aspects of the present invention to provide a relatively stable class of pH sensors, preferably with a working range towards neutral and other biologically relevant pH values.

SUMMARY OF THE INVENTION

The invention relates to pH-sensitive fluorescent dyes which in one aspect are characterized by omission of a hydroxyl or thiol group required by WO 2005/098437 (for more on this see the paragraphs below immediately following the heading "Detailed Description of the Invention"). The current invention in one of its aspects introduces a new family of pH-sensitive fluorescent dyes, having significant advantages over existing fluorescent pH-sensors.

The invention includes within its ambit compounds for example for use as fluorescent pH sensors, the compounds being of Formula A:

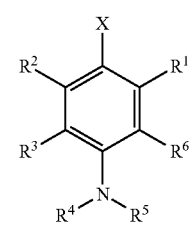

A wherein, $R^1$-$R^6$ are hydrogen or substituents other than electron withdrawing groups; and X is a fluorophore;

or $R^1$ and $R^3$-$R^6$ are hydrogen or substituents other than electron withdrawing groups and X and $R^2$ together form a moiety comprising a 5- or 6-membered heterocyclic ring fused to the benzene ring of formula A between positions X and $R^2$, the compounds being characterised in that $R^1$ and $R^2$ are not hydroxy, thiol or a deprotonated form of either.

One aspect of the present invention provides a compound of Formula I:

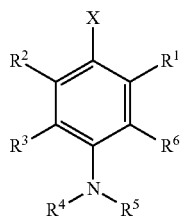

wherein,
- $R^1$, $R^2$, $R^3$ and $R^6$ are each independently H, Z, or an electron donating group (EDG);
- $R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;
- $R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;
- X is a fluorophore;
- Y is $=CR^bR^c$ or $=CR^bR^d$;
- Z is $-OR^c$, $-SR^c$, $-NR^bR^c$;
- $R^b$ is H, alkyl, or substituted alkyl;
- $R^c$ is alkyl or substituted alkyl; and
- $R^d$ is amino or substituted amino;
with the proviso that at least one of Y or Z is present, or a stereoisomer, tautomer, or salt thereof.

An embodiment of the invention provides a compound of Formula II:

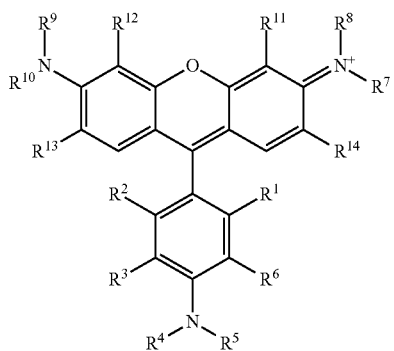

wherein,
- $R^1$, $R^2$, $R^3$ and $R^6$ are each independently H, Z, or an electron donating group (EDG);
- $R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;
- $R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;
- $R^7$, $R^8$, $R^9$ and $R^{10}$ are each independently selected from the group consisting of alkyl, substituted alkyl, aryl, substituted aryl, heteroaryl, substituted heteroaryl, cycloalkyl, substituted cycloalkyl, heterocyclyl, and substituted heterocyclyl; and
- $R^{11}$, $R^{12}$, $R^{13}$ and $R^{14}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $-SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or
- $R^{11}$ and $R^{14}$ are taken together with $R^7$ and $R^8$ to form a fused ring; and $R^{12}$ and $R^{13}$ are taken together with $R^9$ and $R^{10}$ to form a fused ring;
- Y is $=CR^bR^c$ or $=CR^bR^d$;
- Z is $-OR^c$, $-SR^c$, $-NR^bR^c$;
- $R^b$ is H, alkyl, or substituted alkyl;
- $R^c$ is alkyl or substituted alkyl; and
- $R^d$ is amino or substituted amino;
with the proviso that at least one of Y or Z is present, or a stereoisomer, tautomer, or salt thereof.

An embodiment of the invention provides a compound of Formula III:

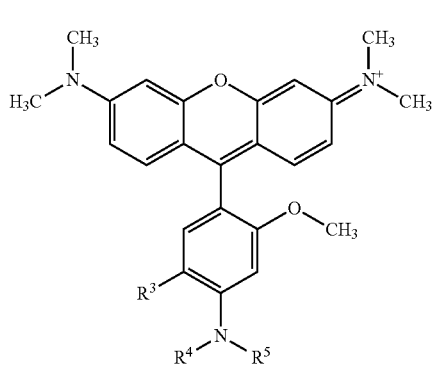

wherein,
- $R^3$ is an electron donating group (EDG); and
- $R^4$ and $R^5$ are each independently selected from the group consisting of H, alkyl, substituted alkyl, alkenyl, substituted alkenyl, acyl, $=CH(amino)$, $=CH(substituted amino)$, $=CH(alkyl)$, and $=CH(substituted alkyl)$.

Another embodiment of the invention provides a compound of Formula IV:

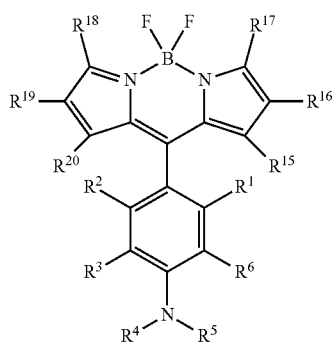

IV

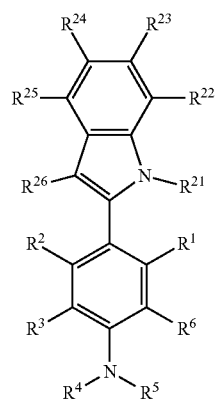

V wherein,

R¹, R², R³ and R⁶ are each independently H, Z, or an electron donating group (EDG);

R⁴ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R⁵ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R¹⁵, R¹⁶, R¹⁷, R¹⁸, R¹⁹ and R²⁰ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO₃H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is =CR$^b$R$^c$ or =CR$^b$R$^d$;

Z is —OR$^c$, —SR$^c$, —NR$^b$R$^c$;

R$^b$ is H, alkyl, or substituted alkyl;

R$^c$ is alkyl or substituted alkyl; and

R$^d$ is amino or substituted amino, or a stereoisomer, tautomer, or salt thereof.

Another embodiment of the invention provides a compound of Formula V:

wherein,

R¹, R², R³ and R⁶ are each independently H, Z, or an electron donating group (EDG);

R⁴ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R⁵ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R²¹ is selected from the group consisting of H, alkyl, substituted alkyl, aryl, substituted aryl, heteroaryl, substituted heteroaryl, cycloalkyl, substituted cycloalkyl, heterocyclyl, and substituted heterocyclyl; and R²², R²³, R²⁴, R²⁵ and R²⁶ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO₃H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is =CR$^b$R$^c$ or =CR$^b$R$^d$;

Z is —OR$^c$, —SR$^c$, —NR$^b$R$^c$;

R$^b$ is H, alkyl, or substituted alkyl;

R$^c$ is alkyl or substituted alkyl; and

R$^d$ is amino or substituted amino, or a stereoisomer, tautomer, or salt thereof.

Another aspect of the present invention provides a compound of Formula VI:

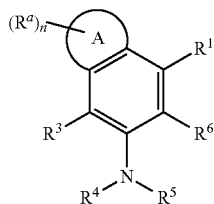

wherein, $R^1$, $R^3$ and $R^6$ are each independently H, Z, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

A is a five or six membered heteroaromatic ring;

Y is $=CR^bR^c$ or $=CR^bR^d$;

Z is $-OR^c$, $-SR^c$, $-NR^bR^c$;

$R^a$ is selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $-SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^b$ is H, alkyl, or substituted alkyl;

$R^c$ is alkyl or substituted alkyl;

$R^d$ is amino or substituted amino; and n is 0, 1, 2, or 3, or a stereoisomer, tautomer, or salt thereof.

An embodiment of the present invention provides a compound of Formula VII:

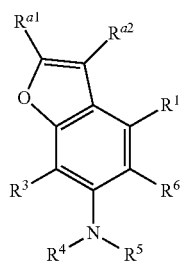

wherein, $R^1$, $R^3$ and $R^6$ are each independently H, Z, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

Y is $=CR^bR^c$ or $=CR^bR^d$;

Z is $-OR^c$, $-SR^c$, $-NR^bR^c$;

$R^{a1}$ and $R^{a2}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $-SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

$R^b$ is H, alkyl, or substituted alkyl;

$R^c$ is alkyl or substituted alkyl; and $R^d$ is amino or substituted amino;

or a stereoisomer, tautomer or salt thereof.

Another embodiment of the present invention provides a fluorescent pH sensitive dye of any one of the compounds of Formulas I, II, III, IV, V, VI, and VII.

Another embodiment of the present invention provides a method for determining the pH of a sample, the method comprising:

(a) contacting the sample with a compound of any of the previous embodiments, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to determine the pH of the sample.

Another embodiment of the present invention provides a method for monitoring the pH inside a live cell, the method comprising:

(a) contacting the cell with a compound of any of the previous embodiments to form a contacted cell;

(b) incubating the contacted cell for a sufficient amount of time for the compound to enter the cell to form a labeled cell;

(c) illuminating the labeled cell with an appropriate wavelength to form an illuminated cell; and (d) detecting fluorescent emissions from the illuminated cell;

wherein the fluorescent emissions are used to monitor the pH inside the cell.

Another embodiment of the present invention provides a method for detecting phagocytosis of a carrier molecule in solution, the method comprising:

(a) conjugating the carrier molecule to a compound to form a carrier conjugate;

(b) contacting the carrier conjugate with a cell to form a contacted cell;

(c) incubating the contacted cell to form an incubated solution;

(d) illuminating the incubated solution to form an illuminated solution; and
(e) detecting fluorescent emissions from the illuminated solution;
wherein fluorescent emissions indicate phagocytosis of the carrier molecule.

Another embodiment of the present invention provides a method for detecting a pH related intracellular process, the method comprising:
(a) contacting a compound of any one of the embodiments described herein with a cell to form a contacted cell;
(b) incubating the contacted cell to form an incubated solution;
(c) illuminating the incubated solution to form an illuminated solution; and
(d) detecting fluorescent emissions from the illuminated solution;
wherein increased fluorescent emissions indicates activation of the intracellular process.

Another embodiment of the present invention provides a method of synthesizing a compound of Formula II:

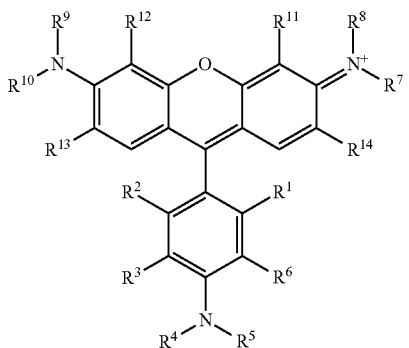

II wherein,
$R^1$, $R^2$, $R^3$ and $R^6$ are each independently H, Z, or an electron donating group (EDG);
$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;
$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;
$R^7$, $R^8$, $R^9$ and $R^{10}$ are each independently selected from the group consisting of alkyl, substituted alkyl, aryl, substituted aryl, heteroaryl, substituted heteroaryl, cycloalkyl, substituted cycloalkyl, heterocyclyl, and substituted heterocyclyl; and
$R^{11}$, $R^{12}$, $R^{13}$ and $R^{14}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminosulfonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or
$R^{11}$ and $R^{14}$ are taken together with $R^7$ and $R^8$ to form a fused ring; and $R^{12}$ and $R^{13}$ are taken together with $R^9$ and $R^{10}$ to form a fused ring;
Y is =CR$^b$R$^c$ or =CR$^b$R$^d$;
Z is —OR$^c$, —SR$^c$, —NR$^b$R$^c$;
$R^b$ is H, alkyl, or substituted alkyl;
$R^c$ is alkyl or substituted alkyl; and
$R^d$ is amino or substituted amino;
or a stereoisomer, tautomer, or salt thereof;
with the proviso that at least one of Y or Z is present;
the method comprising:
(a) contacting a compound of Formula IIA:

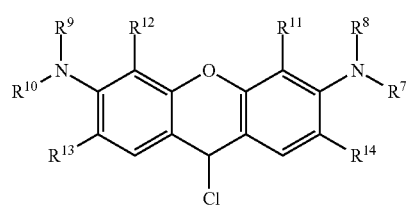

IIA with a compound of Formula IIC:

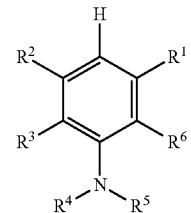

IIC to form a compound of Formula II.

Another embodiment of the present invention provides a method of synthesizing a compound of Formula IV:

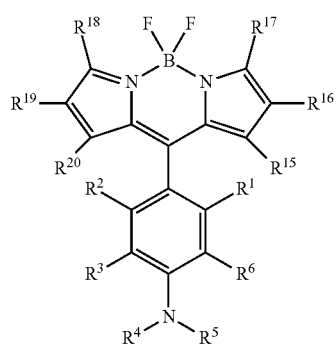

IV wherein,
$R^1$, $R^2$, $R^3$ and $R^6$ are each independently H, Z, or an electron donating group (EDG);
$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^{15}$, $R^{16}$, $R^{17}$, $R^{18}$, $R^{19}$ and $R^{20}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is =CR$^b$R$^c$ or =CR$^b$R$^d$;

Z is —OR$^c$, —SR$^c$, —NR$^b$R$^c$;

$R^b$ is H, alkyl, or substituted alkyl;

$R^c$ is alkyl or substituted alkyl; and $R^d$ is amino or substituted amino;

or a stereoisomer, tautomer, or salt thereof;

the method comprising:

(a) contacting a compound of Formula IVA:

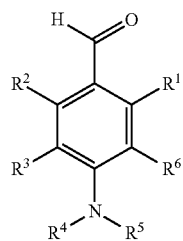

IVA with a compound of Formula IVB and/or IVC:

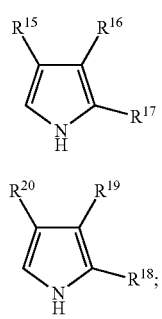

IVB

IVC and 2,3,5,6-tetrachlorocyclohexa-2,5-diene-1,4-dione (cloranil);

and BF$_3$.Et$_2$O;

to form a compound of Formula IV.

Another embodiment of the present invention provides a method of synthesizing a compound of Formula V:

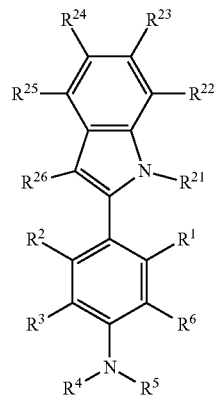

V wherein, $R^1$, $R^2$, $R^3$ and $R^6$ are each independently H, Z, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^{21}$ is selected from the group consisting of H, alkyl, substituted alkyl, aryl, substituted aryl, heteroaryl, substituted heteroaryl, cycloalkyl, substituted cycloalkyl, heterocyclyl, and substituted heterocyclyl; and $R^{22}$, $R^{23}$, $R^{24}$, $R^{25}$ and $R^{26}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is =CR$^b$R$^c$ or =CR$^b$R$^d$;

Z is —OR$^c$, —SR$^c$, —NR$^b$R$^c$;

$R^b$ is H, alkyl, or substituted alkyl;

$R^c$ is alkyl or substituted alkyl; and $R^d$ is amino or substituted amino;

or a stereoisomer, tautomer, or salt thereof;

the method comprising:
(a) contacting a compound of Formula VA:

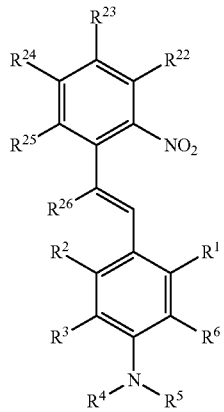

VA with P(OEt)₃, to form the compound of Formula V.

Another embodiment of the invention provides a composition comprising:
(a) a compound of any one of the embodiments provided herein; and
(b) an analyte.

Another embodiment of the invention provides a composition comprising:
(a) a compound of any one of the embodiments provided herein; and
(b) a carrier molecule.

Another embodiment of the invention provides a kit for determining the pH of a sample comprising:
(a) a compound of any one of the embodiments provided herein; and
(b) instructions for determining the pH of the sample.

Aspects and embodiments of the invention are disclosed in the claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 5A corresponds to no Bioparticle Negative Control; FIG. 5B corresponds to On Ice Negative Control; and FIG. 5C corresponds to Maximal Response.

FIG. 6A shows the staining found with a pH sensitive dye (compound 129). In FIG. 6B TMR labeled E. coli were used, wherein the smaller dots of the E. coli that have not been engulfed.

In FIG. 11A the extracellular pH is 5.47, FIG. 11B the pH is 6.8, FIG. 11C the pH is 7.57 and FIG. 11D the pH is 8.04. In each chart, the bar on the right is with nigericin and the left bar is without.

FIGS. 12A and 12B show Murine Macrophage (J774) cells that were incubated with Compound 129-Beta Amyloid overnight in Optimem. The cell in the middle indicates a specific signal from the uptake of the beta amyloid-conjugated to Compound 129.

DETAILED DESCRIPTION OF THE INVENTION

Introduction

Figure 1:
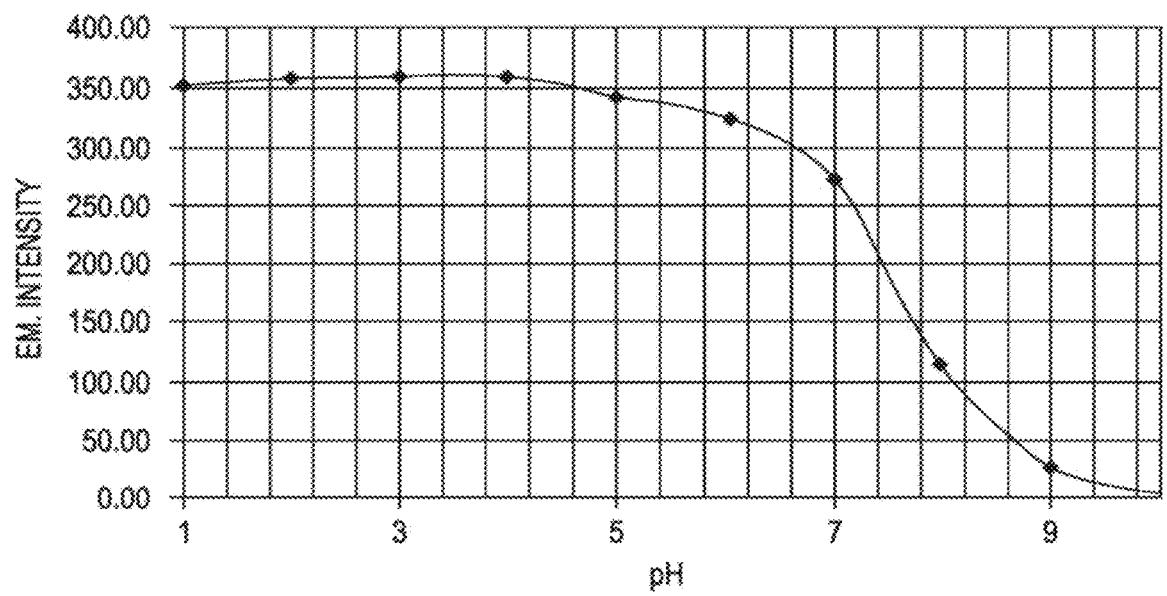
FIG. 1 shows the titration curve of a pH sensor (compound 127), which displays a significant increase in fluorescence upon protonation.

A family of rhodamine-based pH sensors (G. A. Smith, et. al; WO 2005/098437) display pH-dependency similar to amine PET indicators. According to Smith et al., the mechanism of the fluorescence quenching differs from other PET sensors. In particular, the origin of quenching is stipulated to be due to the PET property of the anion, which forms upon ionization of the indicator hydroxyl or thiol group and thus the X substituent (in part) is believed to be responsible for the pH response of the dye, as illustrated in scheme 1:

Scheme 1

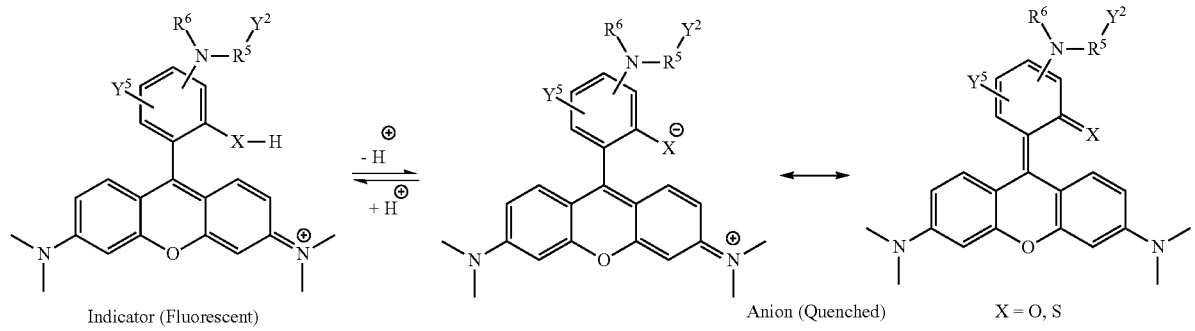

Indicator (Fluorescent)     Anion (Quenched)     X = O, S

However, we have found alkoxy substitutions at the corresponding X position are still capable of demonstrating a modulated fluorescence in response to a change in pH. Thus, while not wishing to be bound by a theory, we postulate that it is the protonation of the nitrogen at the 4 position on the aryl ring that modulates fluorescence. In any event, the present invention is predicated on the insight that the hitherto indispensable hydroxy or thiol group X may be dispensed with provided that a substituent nitrogen is retained.

Further, we have seen that the dyes described by Smith et al. are not stable in solution, most likely as a result of oxidation. Strong electron withdrawing properties of the reporter tetramethylrhodamine moiety significantly decrease the pKa of the indicator group, thus shifting sensors' working range towards acidic pH values.

In some embodiments, therefore, the invention provides pH-sensitive dyes having an aniline moiety (of which the amino group may be substituted or modified as disclosed herein) wherein the benzene ring of the aniline is free from hydroxy and thiol substituents ortho to the fluorophore or, in embodiments, free from hydroxy and thiol at all positions. In particular, these compounds may have, in place of the hydroxy or thiol substituent required by G. A. Smith et al, a moiety wherein the oxygen or sulfur of the hydroxy or thiol group has been incorporated into an ether or thioether linkage, for example as part of an alkoxy group or furan moiety, or their sulfur analogs. Viewed alternatively, those compounds which retain the oxygen or sulfur in etherified form are compounds which provide increased electronic density of the molecule through strategic introduction of electron donating groups to the benzene ring resulting in an electron rich aniline, thereby moving pKa closer to physiological region. Accordingly, the benzene ring may be substituted one or more times (1, 2, 3 or 4 times) by an electron donating group, the electron donating groups being the same or different. In one class of compounds the etherified O or S is replaced by another electron donating group; irrespective of whether the etherified O or S is replaced by another EDG, supplementary electron donating groups may be provided on the benzene ring to further increase the pKa. In one class of compounds, two electron donating groups in total are provided on the benzene ring, in particular two electron donating groups of the type having a lone pair available immediately next to the benzene ring (e.g. alkoxy or dialkylamino, optionally substituted as described herein). Additionally, modifications may be made to increase quantum yield of the molecule. Thus, the pH sensors of the present invention have significant advantages over other PET-based dyes and advantageously provide the benefit of having improved stability and/or pKa in the range of physiological applications.

Also included in the invention are embodiments in which the pKa of the aniline's amino group is increased by modifying the amino group into a more basic nitrogen functional group, in particular amidine or the like. This feature may usefully be adopted as an alternative to replacing the omitted hydroxy or thiol group with another electron donating group; alternatively, modification of the amino group into a more basic group may be combined with substitution of the benzene ring by at least one electron donating group other than a hydroxy or thiol group.

Particular features targeted by the invention include one or more of: (1) dissociation constant pKa inside the physiological range; (2) greater stability (considered to be towards oxidation); (3) flexible synthetic methods allowing introduction of pKa-enhancing substituents along with reactive groups; (4) possibility to introduce different fluorophore reporter moieties in order to make indicators with different spectral properties. As explained, the invention in particular provides compounds, desirably of enhanced stability by dispensing with the previously indispensable hydroxy or thiol at X; the hydroxy or thiol group is advantageously replaced by another electron donating group at the same position. Additionally or alternatively, such other electron donating groups may be substituted at other positions on the benzene ring.

In order to achieve these goals a novel class of the pH-sensitive compounds was designed, synthesized and tested in analytical and biological applications. The structures of the preferred compounds include Formulas I, II, III, IV, V, VI and VII.

Electron Donating/Withdrawing Groups and Aromatic Systems

The topic of electron donating groups and electron withdrawing groups will be familiar to every undergraduate chemistry student but a brief discussion may be appropriate.

Substituents on an aromatic ring may either donate electrons to the aromatic ring or withdraw electrons from the aromatic ring as compared to a hydrogen atom attached to the ring. Substituents may therefore be classified as electron donating groups or electron withdrawing groups.

Many electron donating groups have lone pairs of electrons on the atom adjacent to the pi system of the aromatic ring. Alkyl, aromatic and alkenyl groups are further examples of electron donating groups. Electron withdrawing groups are generally those where the atom adjacent to the aromatic pi system has a formal positive charge, or has a b positive charge (for example, due to being connected to more electronegative atoms). Electron donating groups have an activating effect with respect to further substitution of the ring system and tend to direct further substitution ortho/para, while electron withdrawing groups are deactivating and tend to direct meta. The exception to this is halogen substituents, which, while overall electron withdrawing and deactivating, tend to direct ortho/para due to resonance (lone pair) donation. Table X indicates the relative electron withdrawing and donating character of some common substituents.

TABLE X

Relative electron donating/withdrawing character of different aromatic ring substituents, ranked from most electon donating to most electron withdrawing

| Substituent | Character relative to H | Activating/deactivating | Directing |
| --- | --- | --- | --- |
| —O$^-$ | electron donating | strongly activate | ortho/para |
| —NR$_2$ | electron donating | strongly activate | ortho/para |
| —NH$_2$ | electron donating | strongly activate | ortho/para |
| —OH | electron donating | strongly activate | ortho/para |
| —OR | electron donating | strongly activate | ortho/para |
| —NHC(O)R | electron donating | moderately activate | ortho/para |
| —OC(O)R | electron donating | moderately activate | ortho/para |
| —R | electron donating | weakly activate | ortho/para |
| —Ph | electron donating | weakly activate | ortho/para |
| —CH=CR$_2$ | electron donating | weakly activate | ortho/para |
| —H | reference | neutral | ortho/para |
| —X (X = halo) | electron withdrawing | weakly deactivate | ortho/para |
| —C(O)H | electron withdrawing | moderately deactivate | meta |
| —C(O)R | electron withdrawing | moderately deactivate | meta |
| —C(O)OR | electron withdrawing | moderately deactivate | meta |
| —C(O)OH | electron withdrawing | moderately deactivate | meta |
| —CF$_3$ | electron withdrawing | strongly deactivate | meta |
| —CN | electron withdrawing | strongly deactivate | meta |
| —S(O)$_2$OH | electron withdrawing | strongly deactivate | meta |
| —N$^{(+)}$H$_3$ | electron withdrawing | strongly deactivate | meta |

TABLE X-continued

Relative electron donating/withdrawing character of different aromatic ring substituents, ranked from most electon donating to most electron withdrawing

| Substituent | Character relative to H | Activating/deactivating | Directing |
| --- | --- | --- | --- |
| —N$^{(+)}$R$_3$ | electron withdrawing | strongly deactivate | meta |
| —N$^{(+)}$(O)O$^{(-)}$ | electron withdrawing | strongly deactivate | meta |

The symbol R in the above table in particular stands for alkyl, though it may be substituted in any reasonable way which does not transform the electronic effect of alkyl from donating to withdrawing or vice-versa. This specification further describes suitable electron donating groups for phenylic substitution of the aniline or aniline-like ring described in the specification.

Definitions

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a fluorescent pH sensitive dye" includes a plurality of dyes and reference to "a cell" includes a plurality of cells and the like.

Unless defined otherwise, all technical and scientific terms used herein have the same meaning as commonly understood by one of ordinary skill in the art to which this invention is related. The following terms are defined for purposes of the invention as described herein.

"Alkyl" refers to monovalent saturated aliphatic hydrocarbyl groups having from 1 to 10 carbon atoms and preferably 1 to 6 carbon atoms, e.g. 1, 2, 3, 4, 5 or 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein. Particular substituted alkyl groups comprise a reactive group for direct or indirect linking to a carrier molecule or solid support; as examples may be mentioned alkyl substituted by carboxyl or a carboxyl ester (e.g. an activated ester such as an N-hydroxysuccinimide ester) and alkyl substituted by aminocarbonyl —CONHR$^a$ where R$^a$ is an organic moiety as defined below with reference to the term "aminocarbonyl", e.g. a $C_1$-$C_{10}$ (e.g. $C_1$-$C_6$) alkyl terminally substituted by a reactive group such as, e.g. carboxyl, carboxylester, maleimide.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$— cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

Aminosulfonylamino" refers to the group —NR—SO$_2$NR'R" where R is hydrogen or alkyl and $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O—).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

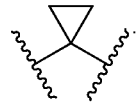 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$— substituted alkenyl, —SO$_2$-cycloalkyl, —SO$_2$-substituted cycloalkyl, —SO$_2$-cycloalkenyl, —SO$_2$— substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$— substituted alkenyl, —OSO$_2$-cycloalkyl, —OSO$_2$-substituted cycloalkyl, —OSO$_2$-cycloalkenyl, —OSO$_2$— substituted cycloalkenyl, —OSO$_2$-aryl, —OSO$_2$-substituted aryl, —OSO$_2$-heteroaryl, —OSO$_2$— substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

A dashed line projecting from a substituent, such as:

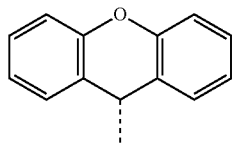

indicates the point of attachment to the base molecule. For a fused ring, dashed lines indicate portions of the base molecule where the fused ring is attached, such as:

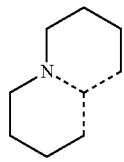

wherein the full molecule could have the structure:

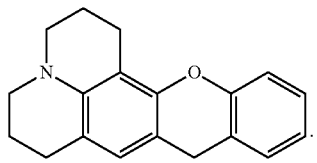 [SMILES: c1ccc2c(c1)Cc1cc3c4c(c1O2)CCCN4CCC3]

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The term "carrier molecule" as used herein refers to a biological or a non-biological component that is or becomes covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. Included is one embodiment in which carrier molecules comprise an organic moiety having at least 4 plural valent atoms and often more than 10 plural valent atoms (i.e. atoms other than hydrogen and halo), e.g. at least 15 such atoms, as in the case of moieties having at least 20 such atoms.

The term "conjugated substance" or "$S_c$" refers to a carrier molecule or solid support.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

"Electron donating group" or "EDG" refers to a substituent with lone pairs that is adjacent to an aromatic ring, such as phenyl, and increases electron density on the ring through a resonance donating effect. Electron donating groups of the present invention include, for example, alkoxy, substituted alkoxy, amino, substituted amino, thiol, alkylthio, hydroxy, acylamino, and (carboxyl ester)oxy. Alkoxy is a particular EDG. Substituted alkoxy is another particular EDG. Also to be mentioned is dialkylamino. A further example is dialkylamino having a substituted alkyl group. Preferred EDGs are —OCH$_3$, —OH, —NH$_2$, —NHCH$_3$, and —N(CH$_3$)$_2$, particularly —OCH$_3$, —NH$_2$, —NHCH$_3$, and —N(CH$_3$)$_2$. Also to be mentioned are alkoxy, alkylthio and dialkylamino, in any of those instances having an alkyl substituent in which the alkyl part is substituted by a moiety -L-Rx or -L$_R$-Sc. The specification also discloses specific compounds or compound classes which include other EDGs than those with a lone pair of electrons adjacent an aromatic ring.

"Fluorescent pH sensitive dye" refers to a compound whose fluorescent spectrum or intensity is affected by pH.

The term "fluorophore" or "fluorogenic" as used herein refers to a composition that is inherently fluorescent or demonstrates a change in fluorescence upon protonation, or binding to a biological compound or metal ion, or metabolism by an enzyme. Preferred fluorophores of the present invention include fluorescent dyes having a high quantum yield in aqueous media. Exemplary fluorophores include xanthene, indole, borapolyazaindacene, furan, and benzofuran, among others. The fluorophores of the present invention may be substituted to alter the solubility, spectral properties or physical properties of the fluorophore.

The term "Linker" or "L", as used herein, refers to a single covalent bond or a moiety comprising series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups (or both). Examples of such pendant moieties are hydrophilicity modifiers, for example solubilising groups like, e.g. sulfo (—$SO_3H$ or —$SO_3$—). In one embodiment, L is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety that includes —C(O)NH—, —C(O)O—, —NH—, —S—, —O—, and the like. Linkers may by way of example consist of a combination of moieties selected from alkyl, —C(O)NH—, —C(O)O—, —NH—, —S—, —O—, —C(O)—, —$S(O)_n$— where n is 0, 1 or 2, —O—, 5- or 6-membered monocyclic rings and optional pendant functional groups, for example sulfo, hydroxy and carboxy. The moiety formed by linker bonded to a reactive group may be designated -L-$R_x$. The reactive group may be reacted with a substance reactive therewith, whereby the linker becomes bonded to a conjugated substance ($S_c$); in this case, the linker typically contains a residue of a reactive group (e.g. the carbonyl group of an ester) and may be designated "-$L_R$". A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The invention includes a class of compounds in which -L- is of the formula -L1-(L2)$_p$-(L3)$_r$- wherein:

p is 0 or 1;
q is 0 or 1;
L1 is a bond, —CONH—, —COO—, or a moiety comprising at least two amino acids,
L2 is —($CH_2$)—, —$CH_2CH_2O$—($CH_2CH_2O$)—$CH_2CH_2O)_s$—$CH_2CH_2$—,
or alkylene having from 1 to 30 carbon atoms and unsubstituted or substituted by at least one $R^a$, e.g. 1, 2, 3, 4, 5 or 6 $R^a$;
L3 is —CONH—($CH_2$)$_t$—, —COO—($CH_2$)$_t$— or a moiety comprising at least two amino acids,
wherein:
r is from 1 to 30, e.g. 1 to 20 as in the case of 1 to 10, such as 1, 2, 3, 4, 5 or 6, for example;
s is 0, 1, 2, 3, 4, 5, 6, 7, 8, 9 or 10, e.g. 1 to 7;
t is from 1 to 30, e.g. 1 to 20 as in the case of 1 to 10, such as 1, 2, 3, 4, 5 or 6, for example;
$R^a$ is sulfo (—$SO_3H$ and/or —$SO_3$), hydroxy, carboxy or amino, particularly sulfo.

Normally, the total number of carbon atoms comprised in alkylene moieties in L is no more than 40, e.g. up to 35, 30, 25, 20, 15 or 10. Normally, there is only a single one of L1 and L3 which comprises a moiety comprising at least two amino acids.

In one class of linkers, p and r are both 0.
In a further class of linkers, p is 1 and r is 0.
In a class of linkers, p and r are both 1.
In embodiments, L1 is a bond, —CONH— or —COO—. In certain compounds L1 is a bond. In certain others, L1 is —CONH—.

L2 in one class of compounds is —($CH_2$)$_u$—, where u is from 1 to 10, e.g. 1, 2, 3, 4, 5 or 6. In another class of compounds L2 is —$CH_2CH_2O$—($CH_2CH_2O$)$_s$—$CH_2CH_2$— where s is often from 1 to 7. In a different class of compounds, L2 is alkylene having from 1 to 10 carbon atoms, e.g. 1, 2, 3, 4, 5 or 6 carbon atoms, and which is unsubstituted or substituted by 1, 2, 3, 4, 5 or 6 sulfo groups, e.g. 1 to 4 sulfo groups. For all L2 moieties mentioned in this paragraph, L1 is —CONH— in a particular class of compounds. For all L2 moieties mentioned in this paragraph and all -L1-L2- combinations mentioned in this paragraph, r is 0 in one class of compounds.

In embodiments, (r+t) is from 1 to 30, e.g. 1 to 20 as in the case of 1 to 10, such as 1, 2, 3, 4, 5 or 6, for example.

As exemplary linkers may be mentioned: a single covalent bond (for example between alkyl and a carboxy group or ester of a carboxy group, or other reactive group); aminocarbonyl (for example linking an alkyl group to a conjugated lipophilic moiety, as illustrated in example 107); a PEG-NH—CO— moiety (for example linking an alkyl group to an NHS-ester or other reactive group, as illustrated in Example 108); an alkylaminocarbonyl group (for example linking an alkyl group to an NHS-ester, amine or other reactive group, as illustrated in Example 109 or 110); an alkylaminocarbonyl group having a pendant group comprising sulfo—e.g. a pendant sulfoalkyl group (for example linking an alkyl group to NHS-ester or other reactive group or to a lipophilic group, as illustrated in Example 123); or a single covalent bond linking an alkyl group to a reactive group such as a carboxy group or ester thereof (as illustrated in Example 126, where a carboxy group is reacted with AcOHC$_2$Br to form a linker—$L_R$ comprising a residue of the carboxy group bonded to a residue of the AcOCH$_2$Br).

"Patient," "subject" or "individual" refers to mammals and includes humans and non-human mammals, such as monkeys, dogs, cats, pocket pets, horses, cows, pigs or rats.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" (or "$R_x$") as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The term "sample" as used herein refers to any material that may contain an analyte of interest or cells. Typically, the sample is a live cell or a biological fluid that comprises endogenous host cells. Alternatively, the sample may be a buffer solution or an environmental sample for which pH determination is needed. The sample may be in an aqueous solution, a viable cell culture or immobilized on a solid or semi solid surface such as a polyacrylamide gel, membrane blot or on a microarray.

The term "solid support" as used here refers to a matrix or medium that is substantially insoluble in liquid phases and capable of binding a molecule or particle of interest. Solid supports of the current invention include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

The Compounds

In general, for ease of understanding the present invention, the pH-sensitive compounds and corresponding substituents will first be described in detail, followed by the many and varied methods in which the compounds find uses, which is followed by exemplified methods of use and synthesis of certain novel compounds that are particularly advantageous for use with the methods of the present invention.

The present compounds find utility in monitoring pH in a sample. For example, we have found that by introducing an electron donating group (EDG) into the 4-amino-2-hydroxyphenyl ring of a fluorogenic pH sensitive compound that we were able to tune the fluorescent properties of the compound (See Formula I). In particular we were able to tune the pKa value and obtain a pH sensitive compound with a pKa value compatible with live cell intracellular applications. We also found that replacing the hydroxyl with an alkoxy moiety not only increased the stability of the compound in an aqueous environment but also resulted in a compound that was pH sensitive, an unexpected advantage in view of the teaching by Smith et al. (supra).

Preferably the pKa value is about 6-7. The pKa of the amino group of the aniline moiety of the compound of Formula I and the like depends on the ability of the aromatic system to share a lone electron pair on the oxygen atom. This ability is affected by additional functional groups introduced into the aromatic system and thus, the pKa is tuned by adding EDG groups to pH sensitive dyes comprising an electron rich aniline moiety.

The sample includes live cells or a biological fluid that comprises endogenous host cell proteins, buffer solutions and environmental samples. Therefore, the present compounds, when comprising a fluorophore, find utility in monitoring pH changes and those events directly and indirectly associated with a change in pH. Monitoring of the pH can also be accomplished in live cells wherein the present compounds are internalized by live cells through a number of different mechanisms, including both passive and cell mediated mechanisms. For example, the present pH-sensitive compounds can comprise a lipophilic group such as an AM (acetoxymethoxy) or acetate ester that allows for entry across the live cell membrane. Once inside the cells nonspecific esterases cleave the AM or acetate ester resulting in a charged molecule that is well retained in the cell. Alternatively, the present compounds can be conjugated to a carrier molecule that allows the compound to be taken up by live cells. Examples include internalization during phagocytosis, wherein the compounds are conjugated to bacterial particles or other proteins (or peptides) that induce phagocytosis by macrophages or monocytes; or up-take through receptor internalization when the present compounds are conjugated to a carrier molecule that binds a receptor and thus induces internalization.

Aniline Moiety

The pH sensing or electron rich aniline moiety of the compounds of the present invention is any moiety that, when protonated, results in the compound being fluorescent, whilst the compound is quenched when the aniline moiety is not in the protonated state. The aniline moiety often has a pKa value in the range of about 2-10, e.g. 3-10. In particular aspects, the pKa of the compound is about 5 to about 8. In another embodiment the pKa of the compound is about 6 to about 8. In another embodiment the pKa of the compound is about 6 to about 7. In another embodiment the pKa of the compound is about 6.5. In another embodiment the pKa of the compound is about 3 to about 10. Preferably the pKa of the present compound is about 6-7.

To tune the pKa to about 6-7, electron donating groups (EDG) were introduced into the aniline moiety on the aryl group. This combined with the presence of an alkoxy or other like substituents on the aryl when a —OH or —SH were not present, unexpectedly resulted in pH sensitive dyes that were stable in an aqueous environment and provide a pKa in the desired range. As disclosed in and with reference to the formulae herein, the amino group of the aniline moiety may be substituted or replaced by another basic moiety of higher pka.

Thus, one embodiment of the present invention provides a compound of Formula A:

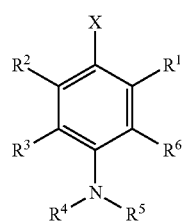

A wherein,
$R^1$-$R^6$ are hydrogen or substituents other than electron withdrawing groups; and
X is a fluorophore;
or $R^1$ and $R^3$-$R^6$ are hydrogen or substituents other than electron withdrawing groups and X and $R^2$ together form a moiety comprising a 5- or 6-membered heterocyclic ring fused to the benzene ring of formula A between positions X and $R^2$,
characterised in that $R^1$ and $R^2$ are not hydroxy, thiol or a deprotonated form of either.

The exact identities of $R^1$-$R^6$ are not critical. Suitably, they may be selected from H and electron donating groups. The skilled person will, of course, use practical good sense to select moieties which are compatible with the desired use of the compound.

In embodiments, none of $R^1$, $R^2$, $R^3$ and $R^6$ is hydroxyl, thiol or a deprotonated form of either.

In one class of compounds, $R^1$-$R^6$ are selected from:
hydrogen;
hydrocarbyl, or hydrocarbyl interrupted by one or more linkages selected from —O—, —S— or —NR$^b$—; or in the case of $R^1$, $R^2$, $R^3$ and $R^6$ hydrocarbyl linked to the benzene ring of Formula A through an —O—, —S— or —NR$^b$— linkage and optionally interrupted by one or more linkages selected from —O—, —S— or —NR$^b$—, wherein hydrocarbyl is unsubstituted or is substituted by -L-$R_x$ or -$L_R$-$S_c$, and wherein:
hydrocarbyl has 1, 2, 3, 4, 5 or 6 carbon atoms;
$R^b$ is H, OH, $C_1$-$C_6$ hydrocarbyl or $C_1$-$C_6$ hydrocarbyl linked to the adjoining N through an —O— linkage and/or interrupted by one or more —O— linkages, wherein hydrocarbyl is unsubstituted or is substituted by -L-$R_x$ or -$L_R$-$S_c$;
L is a linker which is a single covalent bond or a moiety comprising a series of stable covalent bonds and incorporating plural valent atoms (e.g. 1-40 such atoms) selected from C, N, O, S and P;
—$R_x$ is a reactive group;
$L_R$ is a linker -L optionally additionally comprising a residue of a reactive group through which -L is bonded to $S_c$;
—$S_c$ is a conjugated substance.

As previously defined, a conjugated substance is a carrier molecule or solid support as described herein.

In a sub-class, at least one of $R^1$, $R^2$, $R^3$ and $R^6$ is not H, e.g. two of them are not H.

In particular embodiments hydrocarbyl of $R^1$, $R^2$, $R^3$ and $R^6$ is selected from alkyl and alkenyl; more particularly, hydrocarbyl is alkyl; it may be unsubstituted or substituted by -L-$R_x$ or -$L_R$-$S_c$. When $R^1$, $R^2$, $R^3$ or $R^6$ comprises hydrocarbyl, e.g. alkyl, it is in particular ethyl or methyl, especially methyl. When $R^1$, $R^2$, $R^3$ or $R^6$ comprises hydrocarbyl it is often alkoxy or dialkylamino, where alkyl is for example ethyl or methyl, particularly methyl; such groups may be unsubstituted but in certain embodiments at least one of them, and usually exactly one of them, is substituted by -L-$R_x$ or -$L_R$-$S_c$.

One class of compounds of the invention have a dialkylamino group, and the two alkyl moieties of the dialkylamino group may be the same or different, e.g. the same. In one of the sub-classes of this class of compounds, one alkyl moiety is substituted by -L-$R_x$ or -$L_R$-$S_c$.

In one embodiment $R^1$ and $R^3$ are hydrocarbyl-containing groups, e.g. as described in the preceding two paragraphs, whilst $R^2$ and $R^6$ are not hydrocarbyl-containing groups and in many embodiments are both hydrogen.

$R^b$ is typically selected from hydrocarbyl having 1, 2, 3, 4, 5 or 6 carbon atoms, particularly selected from alkyl and alkenyl, and most particularly being alkyl. In some embodiments, hydrocarbyl as $R^b$ is interrupted by an —O— linkage; in other embodiments it is not. $R^b$ is in particular alkyl, therefore. When $R^b$ is hydrocarbyl, e.g. alkyl, it may be unsubstituted; alternatively it may be substituted by -L-$R_x$ or -$L_R$-Sc.

$R^b$ is most often an alkyl group, e.g. methyl or ethyl, particularly methyl. The alkyl group is most often unsubstituted.

In particular embodiments, at least one of $R^1$ and $R^2$ is alkoxy or alkoxy substituted by -L-$R_x$ or -$L_R$-$S_c$, wherein alkoxy has 1, 2, 3, 4, 5 or 6 carbon atoms. Often $R^1$ is as described in the previous sentence but $R^2$ is not, for example $R^2$ is H or, less often, alkyl such as methyl or ethyl, for example.

Included is a class of compounds in which $R^1$ and one, two or three of $R^2$, $R^3$ and $R^6$ (e.g. one of them) are hydrocarbyl linked to the benzene through an —O— or —$NR^b$— linkage, the hydrocarbyl being uninterrupted or interrupted by one or more linkages selected from —O— and —$NR^b$— and being unsubstituted or substituted by -L-$R_x$ or -L-$S_c$, said ones of $R^1$, $R^2$, $R^3$ and $R^6$ being the same as or different from the other(s). In this class of compounds hydrocarbyl and $R^b$ are typically alkyl, e.g. methyl or ethyl, such as methyl. In some compounds at least one of $R^1$, $R^2$, $R^3$ and $R^6$, and usually exactly one of them, is substituted by an -L-$R_x$ or -$L_R$-$S_c$; usually, $R^b$ (if present) is hydrocarbyl and all hydrocarbyls are in particular alkyl, whilst a single one of the hydrocarbyls of $R^1$, $R^2$, $R^3$ and $R^6$ is substituted by an -L-$R_x$ or -$L_R$-Sc. In other compounds, none of $R^1$, $R^2$, $R^3$ and $R^6$ is substituted by -L-$R_x$ or -$L_R$-$S_c$; usually in these compounds $R^b$ (if present) is hydrocarbyl and all hydrocarbyls are in particular alkyl, e.g. methyl or ethyl, particularly methyl.

In one embodiment $R^1$ and $R^3$ are as defined in the preceding paragraph whilst $R^2$ and $R^6$ are not as defined the preceding paragraph and in many embodiments are both hydrogen.

$R^4$ and $R^5$ may be the same or different. Usually they are both hydrocarbyl which is unsubstituted or is substituted by an -L-$R_x$ or -$L_R$-Sc. Hydrocarbyl is typically selected from alkyl and alkenyl and most often is alkyl, e.g. methyl, ethyl or n-propyl. Hydrocarbyl may be interrupted by an —O— linkage, for example exactly one such linkage; more often, it is uninterrupted. In one class of compounds where $R^4$ and $R^5$ are hydrocarbyl, exactly one of $R^4$ and $R^5$ is substituted by an -L-$R_x$ or -$L_R$-Sc whilst the other is unsubstituted; in these compounds $R^4$ and $R^5$ are usually alkyl or alkenyl, e.g. alkyl, as previously mentioned in this paragraph.

The invention includes a class of compounds in which all said hydrocarbyl moieties are alkyl or alkenyl, particularly alkyl, having in either case 1, 2, 3, 4, 5 or 6 carbon atoms.

In one embodiment, the compounds of the invention have a single -L-$R_x$ or -$L_R$-S, group. In another embodiment, the compounds comprise a plurality of such groups, for example two or three of them, such groups may be the same as each other or different from each other. In one embodiment, the compounds have exactly one -L-$R_x$ group; in other embodiments they have exactly one -$L_R$-S, group. They may have two -L-$R_x$ groups or two -$L_R$-$S_c$, groups, or one of each.

In many compounds any -L-$R_x$ or -$L_R$-$S_c$, groups are comprised exclusively in $R^4$ and/or $R^5$; often exactly one of $R^4$ and $R^5$ comprises an -L-$R_x$ or -$L_R$-$S_c$. Sometimes both of $R^4$ and $R^5$ comprise an -L-$R_x$ or -$L_R$-$S_c$.

In some compounds, any -L-$R_x$ or -$L_R$-$S_c$, groups are comprised exclusively in $R^1$, $R^2$, $R^3$ and/or $R^6$; in this case, often exactly one of these groups comprises an -L-$R_x$ or -$L_R$-$S_c$, e.g. one of $R^3$ and $R^6$. For example, $R^1$ may be a moiety other than H (e.g. alkoxy or dialkylamine) and $R^3$ may comprise an -L-$R_x$ or -$L_R$-$S_c$, e.g. be alkyl substituted by such a group, whilst $R^2$ and $R^6$ are both H.

Included are compounds in which one or two of $R^4$ and $R^5$, e.g. exactly one of them, comprises an -L-$R_x$ or -$L_R$-$S_c$, and at least one of $R^1$, $R^2$, $R^3$ and $R^6$, e.g. exactly one of them such as, e.g. $R^3$, also comprises an -L-$R_x$ or -$L_R$-$S_c$.

The compounds of one embodiment comprise an X which is a xanthene, an indole or a borapolyazaindacine. The compounds of other embodiments have an X which is a fluorophore of the compounds of: Formula II; Formula III; Formula IV, Formula V; or Formula VI, e.g. of Formula II.

The invention also includes compounds of Formula (I):

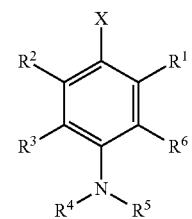

I wherein, $R^1$, $R^2$, $R^3$ and $R^6$ are each independently H, Z, a reactive group, a carrier molecule, a solid support, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, a solid support, heterocyclyl, and substituted heterocyclyl;

X is a fluorophore;

Y is $=CR^bR^c$ or $=CR^bR^d$;

Z is —$OR^c$, —$SR^c$, —$NR^bR^c$;

$R^b$ is H, alkyl, or substituted alkyl;

$R^c$ is alkyl or substituted alkyl; and $R^d$ is amino or substituted amino, or a stereoisomer, tautomer, or salt thereof.

In embodiments, more particularly at least one of Y or Z is present. More particularly still, $R^1$ is not hydroxy or thiol. The absence of hydroxyl or thiol (and their charged species) at $R^1$ increases stability of the compounds of the present invention, particularly when replaced with alkoxy groups.

In another embodiment, $R^1$-$R^5$ can be a lipophilic group, such as an AM (acetoxymethoxy) ester.

The present invention is based, in part, on the addition of an EDG to the aniline group; in certain embodiments constituting this part of the invention, at least one of $R^1$, $R^2$, $R^3$ and $R^6$ needs to be an EDG and at least one of the remaining $R^1$, $R^2$, $R^3$ and $R^6$ needs to be Z. Preferably Z is ortho to the fluorophore, it is not permitted to be hydroxyl or thiol. The absence of hydroxy or thiol (and their charged species) at $R^1$ increases stability of the compounds of the present invention, particularly when replaced with alkoxy groups. Preferred Z groups are —O($C_1$-$C_6$ alkyl) or —N($C_1$-$C_6$ alkyl)$_2$ wherein the alkyl portion can be further substituted by amino, alkyl, aryl, heteroaryl, alkoxy, alkylthio, hydroxy, acylamino, and (carboxyl ester)oxy or halogen.

The functioning of a particular class of molecules of the invention as a pH indicator is illustrated below in Scheme 2:

Scheme 2

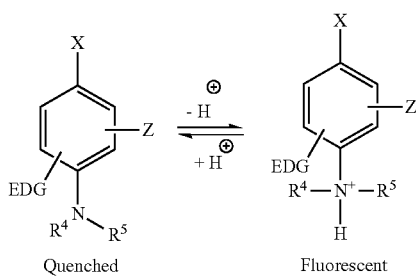

Quenched ⇌ Fluorescent

The EDG is typically at $R^3$, but can be located at any position on the aryl group. Electron donating groups of the present invention include, for example, alkoxy, substituted alkoxy, amino, substituted amino, thiol, alkylthio, hydroxy, acylamino, and (carboxyl ester)oxy. Preferred EDGs are —OCH$_3$, —OH, —NH$_2$, —NHCH$_3$, and —N(CH$_3$)$_2$.

In a more particular embodiment thereof Z is O-alkyl.

In a more particular embodiment thereof Z is N. More particular still $R^b$ is H. More particularly $R^c$ is alkyl.

In a more particular embodiment thereof $R^1$ is —OCH$_3$.

In a more particular embodiment thereof $R^2$ and $R^6$ are H.

In another more particular embodiment the EDG is selected from the group consisting of alkoxy, substituted alkoxy, amino, substituted amino, thiol, alkylthio, hydroxy, acylamino, and (carboxyl ester)oxy. In a sub-class, EDG is not hydroxy or thiol.

In particular embodiments, there is a Z at $R^1$ and at least one further EDG.

One class of compounds have an $R^1$ substitutent which is alkoxy. In some other compounds, $R^1$ is substituted alkoxy.

In another more particular embodiment $R^1$ and $R^3$ are —OCH$_3$ or —N(CH$_3$)$_2$.

In another more particular embodiment the EDG is selected from the group consisting of alkyl, substituted alkyl, alkenyl, substituted alkenyl, aryl, substituted aryl, cycloalkyl, substituted alkyl, heterocyclyl, substituted heterocyclyl, heteroaryl, and substituted heteroaryl.

In another more particular embodiment $R^4$ and $R^5$ are alkyl or substituted alkyl. In a more particular embodiment thereof, $R^5$ is —(CH$_2$)$_n$—CO$_2$(CH$_2$)$_m$H, wherein n is 0, 1, 2, 3, 4 or 5; and m is 0, 1, 2 or 3. More particular still, $R^5$ is —(CH$_2$)$_3$—CO$_2$CH$_3$.

In another embodiment thereof $R^4$ is ethyl.

In another embodiment $R^4$ is H or absent. In another embodiment thereof $R^5$ is Z. More particularly, Z is =CH (substituted amino). More particularly Z is =CH—N(CH$_3$)$_2$.

In another embodiment $R^5$ is —C(=NH)—NH$_2$, —C(=NH)—NH(alkyl), —C(=NH)—NH(substituted alkyl), or —C(=NH)—N(alkyl)$_2$. The amidine (or related guanidine) group, which are known to be strong organic bases (Oszczapowicz, J.; Jaroszewska-Manaj, J.; Golimowska, K. *J. Chem. Soc., Perkin Trans.* 2, 2000, 2343-2346) provides the advantage of not requiring presence of additional pKa enhancing groups when pka is to be increased.

In another more particular embodiment of any of the previous embodiments, the pKa of the compound is about 5 to about 8. In another embodiment the pKa of the compound is about 6 to about 8. In another embodiment the pKa of the compound is about 6 to about 7. In another embodiment the pKa of the compound is about 6.5. In another embodiment the pKa of the compound is about 3 to about 10.

The 4-position nitrogen of the aniline or aniline-like ring of the compounds of the invention does of course always have a permissible valency.

In an alternative embodiment of the present invention the aniline moiety is a compound of Formula VI, wherein the aniline moiety is also the fluorophore X:

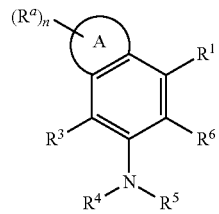

wherein,

A is a five or six membered heteroaromatic ring;

$R^a$ is selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and n is 0, 1, 2, or 3; or a stereoisomer, tautomer, or salt thereof.

In a more particular embodiment A is five membered ring selected from the group consisting of furanyl, pyrrolyl, imidazolyl, oxazolyl, thiazolyl, thiophenyl, pyrazolyl, and isoxazolyl. More particular still, A is furanyl.

In another more particular embodiment A is a six membered ring selected from the group consisting of, pyridinyl, pyrimidinyl, pyrazinyl and pyridazinyl.

In another more particular embodiment, A is furanyl, n is 1 and $R^a$ is a substituted heteroaryl group. In a more particular embodiment thereof, the substituted heteroaryl group is an oxazole. More particular still, the oxazole is substituted with a carboxyl group.

Fluorophores

The fluorophore of the present invention functions as a reporter molecule to confer a detectable signal, directly or indirectly, to the sample as a result of a change in pH. This results in the ability to measure and monitor pH changes in a sample to directly and indirectly detect specific events associated with a change in pH.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon protonation is a change in fluorescence intensity that is greater than approximately 150% relative to the same compound wherein the aniline moiety is not protonated on the nitrogen, more preferably greater than 5-fold, and most preferably more that 10-fold.

The present fluorophores can be any fluorophore known to one skilled in the art. A wide variety of fluorophores that may be suitable for incorporation into the pH sensitive compounds of the invention are already known in the art (RICHARD P. HAUGLAND, MOLECULAR PROBES HANDBOOK OF FLUORESCENT PROBES AND RESEARCH PRODUCTS (2002)). Preferably, the fluorophore is quenched, or substantially non-fluorescent, until the nitrogen on the aniline moiety is protonated.

A fluorescent dye of the present invention is any chemical moiety that exhibits an absorption maximum beyond 280 nm, and when covalently linked to the electron rich aniline moiety of the present invention, forms a present fluorogenic pH-sensitive compound. Dyes of the present invention include, without limitation; a pyrene, an anthracene, a naphthalene, an acridine, a stilbene, an indole or benzoindole, an oxazole or benzoxazole, a thiazole or benzothiazole, a 4-amino-7-nitrobenz-2-oxa-1, 3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (Int. Publ. No. WO 97/39064 and U.S. Pat. No. 6,162,931).

Preferred dyes of the invention include xanthene, borapolyazaindacene, and indoles and derivatives thereof. Preferred xanthenes are fluorescein, rhodamine and derivatives thereof.

In one aspect the fluorophore contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art. In one aspect the fluorophore is a xanthene that comprises one or more julolidine rings.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group, solid support and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, borapolyazaindacene, indole and derivatives thereof. The choice of the fluorophore attached to the aniline moiety will determine the pH-sensitive compound's absorption and fluorescence emission properties as well as its live cell properties, i.e. ability to localize within a cell.

Selected sulfonated reporter moieties also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

In one embodiment, the fluorophore is attached to the aniline moiety via a present linker. The fluorophore (and reactive group, carrier molecules, and solid support) comprise a linker that is used to covalently attach the substituents to the aniline moiety present compounds. The fluorophore (and solid support, carrier molecule or reactive group) may be directly attached (where Linker is a single bond) to the moieties or attached through a series of stable bonds. Preferrably the fluorophore is directly attached by a single covalent bond to the aniline moiety, but can also be attached via a linker as described below for reactive group, carrier molecules, and solid support. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, or arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

Any combination of linkers may be used to attach the carrier molecule, solid support or reactive group and the present compounds together. The linker may also be substituted to alter the physical properties of the fluorophore or aniline moiety, such as spectral properties of the dye.

Another important feature of the linker is to provide an adequate space between the carrier molecule, reactive group or solid support and the aniline moiety or fluorophore so as to prevent steric hinderance. Therefore, the linker of the present compound is important for (1) attaching the carrier molecule, reactive group or solid support to the compound and attaching the fluorophore to the aniline moiety, (2) providing an adequate space between the carrier molecule, reactive group or solid support and the compound so as not to sterically hinder the action of the compound and (3) for altering the physical properties of the present compounds.

In an embodiment the fluorophore is selected from the group consisting of a xanthene, an indole and a borapolyazaindacine, wherein these fluorophores have a high quantum yield in aqueous media.

In one particular aspect the fluorophore X is:

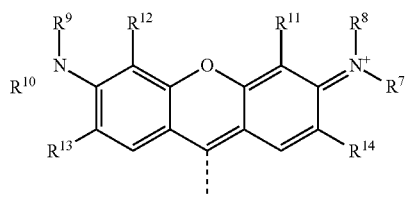

wherein, $R^7$, $R^8$, $R^9$ and $R^{10}$ are each independently selected from the group consisting of alkyl, substituted alkyl, aryl, substituted aryl, heteroaryl, substituted heteroaryl, cycloalkyl, substituted cycloalkyl, heterocyclyl, and substituted heterocyclyl; and $R^{10}$ and $R^{11}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^{11}$ and $R^{14}$ are taken together with $R^7$ and $R^8$ to form a fused ring; and/or $R^{12}$ and $R^{13}$ are taken together with $R^9$ and $R^{10}$ to form a fused ring.

In a more particular embodiment thereof $R^7$, $R^8$, $R^9$ and $R^{10}$ are alkyl. More particular still, $R^7$, $R^8$, $R^9$ and $R^{10}$ are methyl.

In a more particular embodiment thereof $R^{11}$, $R^{12}$, $R^{13}$ and $R^{14}$ are H.

In a more particular embodiment thereof $R^1$ and $R^{14}$ are taken together with $R^7$ and $R^8$ to form a fused ring; and $R^{12}$ and $R^{13}$ are taken together with $R^9$ and $R^{10}$ to form a fused ring; wherein the fused ring has the following structure:

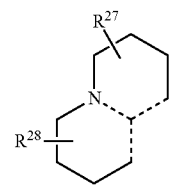

wherein, $R^{27}$ and $R^{28}$ are each independently selected from the group consisting of H, alkyl, substituted alkyl, alkoxy, substituted alkoxy, alkenyl, substituted alkenyl, alkynyl, substituted alkynyl, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In another embodiment the fluorophore X is:

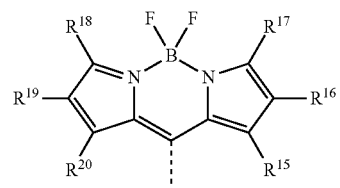

$R^{15}$, $R^{16}$, $R^{17}$, $R^{18}$, $R^{19}$ and $R^{20}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In a more particular embodiment thereof $R^{16}$ and $R^{19}$ are H.

In a more particular embodiment thereof $R^{15}$, $R^{17}$, $R^{18}$ and $R^{20}$ are methyl.

In another embodiment the fluorophore X is:

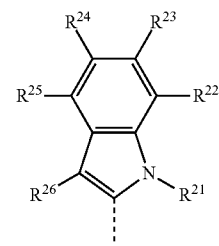

$R^{21}$ is selected from the group consisting of H, alkyl, substituted alkyl, aryl, substituted aryl, heteroaryl, substituted heteroaryl, cycloalkyl, substituted cycloalkyl, heterocyclyl, and substituted heterocyclyl; and $R^{22}$, $R^{23}$, $R^{24}$, $R^{25}$ and $R^{26}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl.

In a more particular embodiment thereof $R^{21}$, $R^{22}$, $R^{24}$, $R^{25}$ and $R^{26}$ are H.

In a more particular embodiment thereof $R^{23}$ is carboxyl ester.

In a more particular embodiment thereof $R^{23}$ is —CO$_2$CH$_3$.

In a particular embodiment of the invention the pH sensitive compounds have the Formula II:

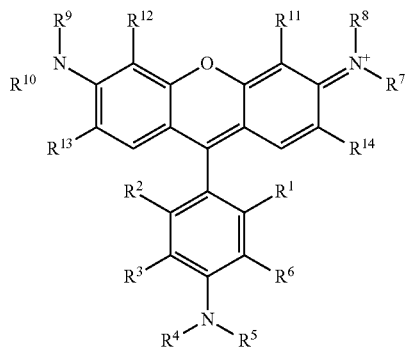

wherein, $R^1$-$R^{14}$ are as described above or a stereoisomer, tautomer, or salt thereof.

In particular embodiments $R^7$, $R^8$, $R^9$ and $R^{10}$ are alkyl $R^1$, $R^{12}$, $R^{13}$ and $R^{14}$ are H, Z is O-alkyl. $R^1$ is —OCH$_3$, $R^2$ and $R^6$ are H and $R^4$ and $R^5$ are alkyl or substituted alkyl. In a more particular embodiment thereof, $R^5$ is —(CH$_2$)$_n$—CO$_2$(CH$_2$)$_m$H, wherein n is 0, 1, 2, 3, 4 or 5; and m is 0, 1, 2 or 3. More particular still, $R^5$ is —(CH$_2$)$_3$—CO$_2$CH$_3$.

In another embodiment $R^4$ is H or absent. In another embodiment thereof $R^5$ is Z. More particularly, Z is =CH(substituted amino). More particularly Z is =CH—N(CH$_3$)$_2$.

In another embodiment $R^5$ is —C(=NH)—NH$_2$, —C(=NH)—NH(alkyl), —C(=NH)—NH(substituted alkyl), or —C(=NH)—N(alkyl)$_2$.

Another embodiment of the invention provides a compound of Formula III:

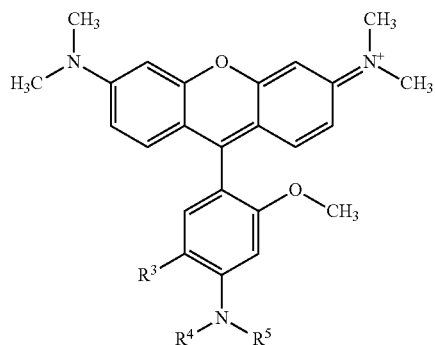

wherein, $R^3$ is an electron donating group (EDG); and $R^4$ and $R^5$ are each independently selected from the group consisting of H, alkyl, substituted alkyl, alkenyl, substituted alkenyl, acyl, =CH(amino), =CH(substituted amino), =CH(alkyl), and =CH(substituted alkyl), provided that the attached nitrogen has a permissible valency.

In another separate embodiment of structure of Formula III, $R^3$ is H, Z or an electron donating group (EDG); $R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl; $R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl; Y is =CR$^b$R$^c$ or =CR$^b$R$^d$; Z is —OR$^c$, —SR$^c$, —NR$^b$R$^c$; R$^b$ is H, alkyl, or substituted alkyl; R$^c$ is alkyl or substituted alkyl; and R$^d$ is amino or substituted amino.

In another more particular embodiment the EDG is selected from the group consisting of alkoxy, substituted alkoxy, amino, substituted amino, thiol, alkylthio, hydroxy, acylamino, and (carboxyl ester)oxy.

In another more particular embodiment $R^3$ is —OCH$_3$ or —N(CH$_3$)$_2$.

In another more particular embodiment the EDG is selected from the group consisting of alkyl, substituted alkyl, alkenyl, substituted alkenyl, aryl, substituted aryl, cycloalkyl, substituted alkyl, heterocyclyl, substituted heterocyclyl, heteroaryl, and substituted heteroaryl.

In another more particular embodiment $R^4$ and $R^5$ are alkyl or substituted alkyl. In a more particular embodiment thereof, $R^5$ is —(CH$_2$)$_n$—CO$_2$(CH$_2$)$_m$H, wherein n is 0, 1, 2, 3, 4 or 5; and m is 0, 1, 2 or 3. More particular still, $R^5$ is —(CH$_2$)$_3$—CO$_2$CH$_3$.

In another embodiment thereof $R^4$ is ethyl.

In another embodiment $R^5$ is =CH(amino), =CH(substituted amino), =CH(alkyl), or =CH(substituted alkyl).

In another embodiment $R^5$ is —C(=NH)—NH$_2$, —C(=NH)—NH(alkyl), —C(=NH)—NH(substituted alkyl), or —C(=NH)—N(alkyl)$_2$.

Another embodiment of the invention provides a compound of Formula IV:

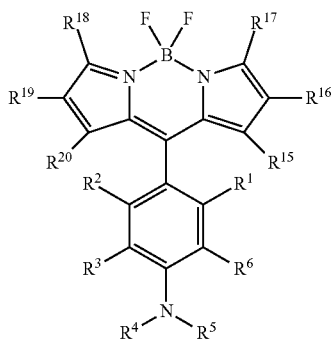

wherein,

R¹-R⁶ and R¹⁵-R²⁰ are as described above.

Another embodiment of the invention provides a compound of Formula V:

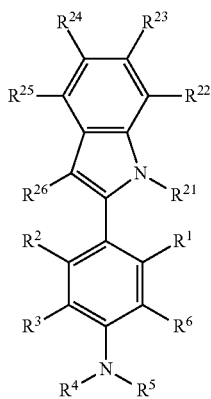

wherein,

R¹-R⁶ and R²¹-R²⁶ are as described above.

Another embodiment of the present invention provides a compound of Formula VII:

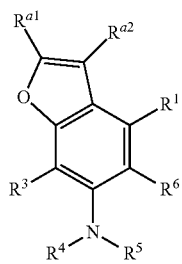

wherein,

R¹, R³ and R⁶ are each independently H, Z, or an electron donating group (EDG);

R⁴ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R⁵ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

Y is =CR$^b$R$^c$ or =CR$^b$R$^d$;

Z is —OR$^c$, —SR$^c$, —NR$^b$R$^c$;

R$^{a1}$ and R$^{a2}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO₃H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

R$^b$ is H, alkyl, or substituted alkyl;

R$^c$ is alkyl or substituted alkyl; and

R$^d$ is amino or substituted amino;

or a stereoisomer, tautomer or salt thereof.

In another more particular embodiment, R$^{a2}$ is a substituted heteroaryl group. In a more particular embodiment thereof, the substituted heteroaryl group is an oxazole. More particular still, the oxazole is substituted with a carboxyl group.

In another more particular embodiment, R$^{a1}$ is H.

In another embodiment of any of the foregoing, the compound (particularly the compound of Formula I, II, III, IV, V, VI, or VII) is a fluorogenic pH sensitive dye.

Reactive Groups

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the aniline moiety, linker, fluorophore, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In exemplary embodiment, at least one member selected from R¹, R², R³, R⁴, R⁵, and R⁶ is a reactive group. Preferably, at least one of R³, R⁴, R⁵, and R⁶ is a reactive group, most preferred is at least one of R⁴ or R⁵. Alternatively, if the present compound comprises a carrier molecule or solid support a reactive group may be covalently attached independently to those substituents, allowing for further conjugation to a fluorophore, carrier molecule or solid support.

These reactive groups are synthesized during the formation of the present compound and carrier molecule and solid support containing compounds to provide chemically reactive pH sensitive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |

TABLE 1-continued

Examples of some routes to useful covalent linkages

| Electrophilic Group | Nucleophilic Group | Resulting Covalent Linkage |
|---|---|---|
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —OCNR$^x$NHR$^y$, where R$^x$ and R$^y$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

Carrier Molecules

In an exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, polymers and bacterial particles. In exemplary embodiment, at least one member selected from $R^1$, $R^2$, $R^3$, $R^4$, $R^5$, and $R^6$ is a carrier molecule. Preferably, at least one of $R^3$, $R^4$, $R^5$, and $R^6$ is a carrier molecule, most preferred is at least one of $R^4$, or $R^5$.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

Carrier molecules may comprise a label or a fluorescent dye or quencher.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, a growth factor, bacterial particle or a binding partner for a cell receptor.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 2.

TABLE 2

Representative Specific Binding Pairs

| antigen | antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization Solid Supports In an exemplary embodiment, the present compounds of the invention are covalently bonded to a solid support. The solid support may be attached to the compound either through the aniline moiety, fluorophore, or through a reactive group, if present, or through a carrier molecule, if present. Even if a reactive group and/or a carrier molecule are present, the solid support may be attached through the aniline moiety or fluorophore. In an exemplary embodiment, at least one member selected from $R^1$, $R^2$, $R^3$, $R^4$, $R^5$, and $R^6$ is a solid support. Preferably, at least one of $R^3$, $R^4$, $R^5$, and $R^6$ is a solid support, most preferred is at least one of $R^4$, or $R^5$.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

Preparation of Conjugates

Conjugates of components (carrier molecules or solid supports), e.g., drugs, peptides, toxins, nucleotides, phospholipids, proteins and other organic molecules are prepared by organic synthesis methods using the reactive dyes of the invention, are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the fluorophore or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Synthesis

An embodiment of the present invention provides a method of synthesizing a compound of Formula II:

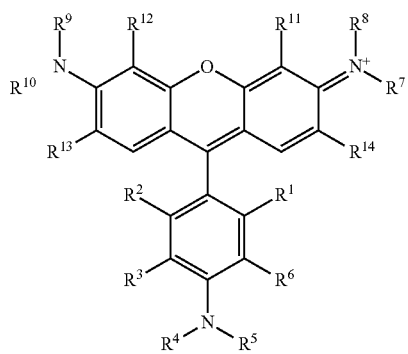

wherein, $R^1$, $R^2$, $R^3$ and $R^6$ are each independently H, Z, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^7$, $R^8$, $R^9$ and $R^{10}$ are each independently selected from the group consisting of alkyl, substituted alkyl, aryl, substituted aryl, heteroaryl, substituted heteroaryl, cycloalkyl, substituted cycloalkyl, heterocyclyl, and substituted heterocyclyl; and $R^{11}$, $R^{12}$, $R^{13}$ and $R^{14}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^{11}$ and $R^{14}$ are taken together with $R^7$ and $R^8$ to form a fused ring; and $R^{12}$ and $R^{13}$ are taken together with $R^9$ and $R^{10}$ to form a fused ring;

Y is =CR$^b$R$^c$ or =CR$^b$R$^d$;

Z is —OR$^c$, —SR$^c$, —NR$^b$R$^c$;

R$^b$ is H, alkyl, or substituted alkyl;

R$^c$ is alkyl or substituted alkyl; and

R$^d$ is amino or substituted amino;

or a stereoisomer, tautomer, or salt thereof;

with the proviso that at least one of Y or Z is present;

the method comprising:

(a) contacting a compound of Formula IIA:

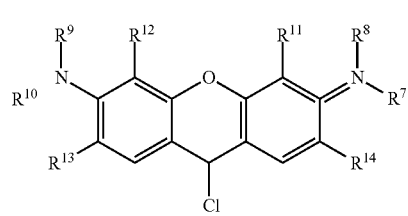

with a compound of Formula IIC:

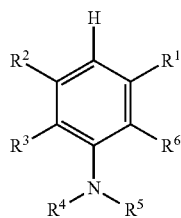

IIC to form a compound of Formula II.

Another more particular embodiment further comprises synthesizing the compound of Formula IIA, the method comprising:

(b) contacting a compound of Formula IIB

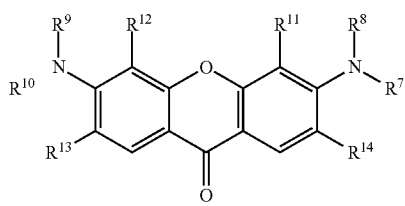

IIB with a chlorinating agent, to form a compound of Formula IIA.

In another embodiment the chlorinating agent is oxalyl chloride.

Another embodiment of the present invention provides a method of synthesizing a compound of Formula IV:

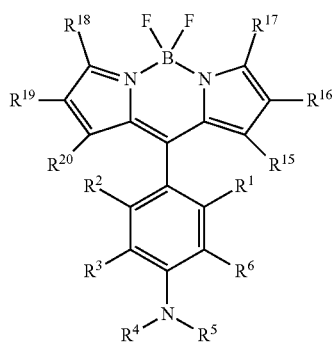

IV wherein, $R^1$, $R^2$, $R^3$ and $R^6$ are each independently H, Z, or an electron donating group (EDG);

$R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

$R^{15}$, $R^{16}$, $R^{17}$, $R^{18}$, $R^{19}$ and $R^{20}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is $=CR^bR^c$ or $=CR^bR^d$;

Z is —OR$^c$, —SR$^c$, —NR$^b$R$^c$;

$R^b$ is H, alkyl, or substituted alkyl;

$R^c$ is alkyl or substituted alkyl; and $R^d$ is amino or substituted amino;

or a stereoisomer, tautomer, or salt thereof;

the method comprising:

(a) contacting a compound of Formula IVA:

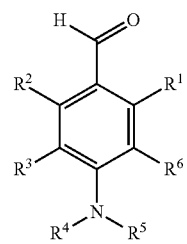

IVA with a compound of Formula IVB and/or IVC:

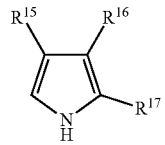

IVB

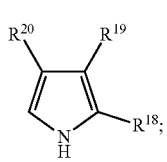

IVC and 2,3,5,6-tetrachlorocyclohexa-2,5-diene-1,4-dione (cloranil);

and BF$_3$.Et$_2$O;

to form a compound of Formula IV.

Another embodiment of the present invention provides a method of synthesizing a compound of Formula V:

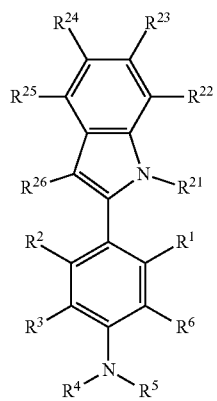

V wherein,

R[1], R[2], R[3] and R[6] are each independently H, Z, or an electron donating group (EDG);

R[4] is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R[5] is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;

R[21] is selected from the group consisting of H, alkyl, substituted alkyl, aryl, substituted aryl, heteroaryl, substituted heteroaryl, cycloalkyl, substituted cycloalkyl, heterocyclyl, and substituted heterocyclyl; and R[22], R[23], R[24], R[25] and R[26] are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, —SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;

Y is =CR$^b$R$^c$ or =CR$^b$R$^d$;

Z is —OR$^c$, —SR$^c$, —NR$^b$R$^c$;

R$^b$ is H, alkyl, or substituted alkyl;

R$^c$ is alkyl or substituted alkyl; and

R$^d$ is amino or substituted amino;

or a stereoisomer, tautomer, or salt thereof;

the method comprising:
(a) contacting a compound of Formula VA:

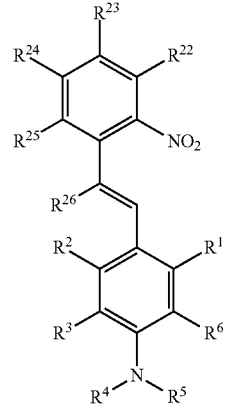

VA with P(OEt)$_3$, to form the compound of Formula V.

Another more particular embodiment further comprises synthesizing the compound of Formula VA, the method comprising:
(a) contacting a compound of Formula IVA:

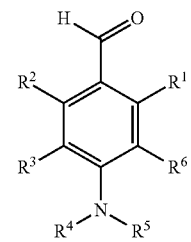

IVA with a compound of Formula VB:

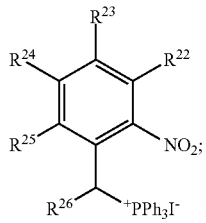

VB to form the compound of Formula VA.

Another more particular embodiment of any one of the above methods of synthesis further comprises a purifying step. In a more particular embodiment, said purifying step comprises at least one of: column chromatography, trituration, recrystallization, filtration, or aqueous separation.

Methods

The dyes and complexes of the present invention can be used to determine the pH of living cells or cell compartments, a change in pH to the local environment caused by a cell as well as directly and indirectly detect specific cellular events associated with a change in pH. One method of the present invention involves detecting contamination in cell culture or on agar plates. For sake of clarity, the sample also includes material other than live cells and cell compartments such as cell culture medium, biological fluids, diagnostic materials, and bacterial medium such as agar plates. By "a cell compartment" typically we mean one of the many organelles suspended in the cell cytoplasm. The pH of a cell or cell compartment can be measured by introducing a dye or dye conjugate into a cell or cell compartment, irradiating the dye or conjugate with a suitable light source, and observing the intensity of fluorescence of the dye or conjugate. The observed fluorescence intensity can then be used to determine pH by a variety of methods known in the field, selected according to the method of accumulation of the dye or conjugate. For instance, the observed fluorescence may be compared to a known standard, for example a calibration curve of fluorescence intensity versus pH, or to fluorescence intensity measurements indicative of the total dye or conjugate present. Any conventional fluorimetric equipment can be used to irradiate the sample, and to measure the resulting fluorescent response.

As stated above the sample comprises live cells, intracellular fluids, extracellular fluids, biological fluids, sera, biological fermentation media, environmental sample, industrial samples, proteins, peptides, buffer solutions, biological fluids or chemical reactors, blood cells, immune cells, cultured cells, muscle tissue, neurons, extracellular vesicles; vascular tissue, blood fluids, saliva, urine, water, soil, waste water, sea water; pharmaceuticals, foodstuffs or beverages. In one aspect the sample is immobilized on a polymeric membrane, within a polymeric gel, on a microparticle, on a microarray, on a silicon chip, on a glass slide, on a microwell plate, and on a microfluidic chip.

The compounds may therefore be used as pH sensors in relation to samples comprising or suspected of comprising a biological entity or biological substance. The compounds may be used in assays involving a biological entity or biological substance. The invention provides the use of the compounds in a biological assay for the purposes described herein, particularly as a pH sensor.

Thus, in one embodiment the methods of the present invention comprise determining the pH of a sample, wherein the method comprises
 (a) contacting the sample with a compound of any of the previous embodiments, to form a contacted sample;
 (b) incubating the contacted sample for an appropriate amount of time to form an incubated sample;
 (c) illuminating the incubated sample with an appropriate wavelength to form an illuminated sample; and
 (d) detecting fluorescent emissions from the illuminated sample;
wherein the fluorescent emissions are used to determine the pH of the sample.

[In another aspect of the invention, the compounds are used in cell culture for detection of contamination. In another aspect of the invention, the compounds are used in on agar plates for the detection of contamination.

In another particular embodiment a change in the pH inside the cell corresponds to a cellular process. In another more particular embodiment the compound is conjugated to a protein, nucleic acid or lipid. In another more particular embodiment the compound is conjugated to transferrin. In another more particular embodiment the compound is conjugated to a carrier molecule through a succinimidyl ester. In another more particular embodiment the compound is conjugated to EGF or EGFR. In another more particular embodiment the compound is non-fluorescent before entering the cell. More particularly, the compound becomes fluorescent after entering the cell. In another more particular embodiment the compound enters the cell through phagocytosis.

In another aspect, the present invention provides a method for monitoring the pH inside a live cell, the method comprising:
 (a) contacting the cell with a compound of any of the previous embodiments to form a contacted cell;
 (b) incubating the contacted cell for a sufficient amount of time for the compound to enter the cell to form a labeled cell;
 (c) illuminating the labeled cell with an appropriate wavelength to form an illuminated cell; and
 (d) detecting fluorescent emissions from the illuminated cell;
wherein the fluorescent emissions are used to monitor the pH inside the cell.

Typically, the dyes and/or conjugates are introduced into a living cell or cell compartment by mixing with a sample comprising a cell or cell compartment, and then leaving the mixture to incubate for a time interval adequate to allow entry of the dye or conjugate into the cell or cell compartment. During this time interval, the dye or conjugate either passively diffuses across the plasma membrane or is taken up by the call or cell compartment by a cell mediated mechanism.

In the case of conjugates, typically target molecules, including bacterial particles that induce phagocytosis and specific binding patterns that bind a cellular receptor and induce receptor internalization, are generally cell or cell compartment specific, hence a specific conjugate generally attaches to only one kind of cell or cell compartment. Once attached to a cell or cell compartment, the dye conjugate may diffuse through a membrane of that cell or cell compartment or be trafficked to a specific cell compartment by receptor-mediated endocytosis, hence exposing itself to the internal pH of the cell or cell compartment.

The dyes and conjugates of the present invention allow for a more accurate determination of pH as compared to existing dyes because the pKa's of the dyes and conjugates of the present invention can, by design, be adjusted by substitution to a variety of pKa values. This is accomplished by the addition of EDG groups on the aniline moiety and by substitution at one of the remaining R1-R6 with a group that is not —OH or —SH. Thus, some are tuned to the pH of the cell or cell compartment of interest, and consequently will be ideal for measuring the pH of a cell or cell compartment when accumulated by receptor-mediated endocytosis or any non-passive accumulation mechanism as well as by passive accumulation. Others will have a pKa far from the pH of the cell media or extracellular matrix. The dyes of the present invention are tuned to match the sample of choice with the understanding that the compounds become fluorescent when the pH of the sample drops below the pKa of the present compound.

Accumulation will occur passively when one form of the dye or conjugate with respect to pH (the uncharged form) freely penetrates the cell or cell compartment of interest and the other form (a charged form) is non-penetrating. Fluorescence will approach its equilibrium position provided the form of the dye accumulated is the fluorescent form and that accumulation to equilibrium has occurred. The observed fluorescence intensity can then be used to determine pH according to any of the known methods, for instance by reference to calibration data, or by comparing the observed fluorescence intensity to the fluorescence intensity observed on acidifying the test sample so that all the dye or conjugate fluoresces, the ratio of the two fluorescence intensities coupled with the known pKa allowing determination of pH. Passive accumulation can be achieved by use of a dye that is not attached to a carrier molecule or solid support or a dye that is attached to a small, relatively hydrophobic target molecule capable of diffusing through the cell membrane, such as one or more AM ester groups. However, we have found that dyes comprising a reactive group, such as succinimidyl ester, also appear to passively accumulate in cells.

We have observed that the pH sensitive-dyes of the present invention preferentially detect neurons when using passive accumulation. Without wishing to be bound by a theory, it appears that the neurons have a more acidic pH than the surrounding media or cells resulting in a fluorescent response of the accumulated dye in the neurons. We have shown that when the surrounding media or extracellular matrix is acidified there is a fluorescent response of dye that has not accumulated in the neurons, further supporting the passive accumulation of the dye into an acidic environment and providing a method for selectively labeling neurons. See Example 307.

One preferred embodiment of this invention provides methods of identifying a first neuron or plurality of neurons in a neural tissue slice, or a neuronal cell is a heterogeneous mixture comprising neuronal and non-neuronal cell types. This invention also provides a method of detecting the effect of a neuromodulator on a connection between neurons or a plurality of neurons forming a circuit; methods of identifying an inhibitory connection between or on neurons; and a method of identifying neurons in vivo or in vitro.

In a particular embodiment, healthy neurons are identified in mixed cultures of living cells or preparations of cells, such as tissue slices or whole mount. In vivo identification of neurons or other metabolically active cells such as cardiac and skeletal myocytes are particularly preferred methods employing the compounds of the present invention.

Another embodiment of the invention provides a method for identifying a target cell within a population of cells whereby the target cell is differentially labeled relative to neighboring cells within the population, the method comprising:
  contacting a compound as described herein with the population of cells to form a contacted cell population;
  incubating the contacted cell population for a period of time sufficient for the compound to enter the target cell, thereby forming an incubated cell population; and
  illuminating the incubated cell population, wherein the target cell is identified by a differential label relative to neighboring cells within the population.

In a more particular embodiment, the target cell is a neuronal cell. More particular still, the neuronal cell is identified by increased fluorescence as compared with neighboring cells. In another embodiment, the population of cells is part of a tissue. More particularly, the tissue is selected from the group consisting of tumor tissue, epidermal tissue, muscle tissue, bone marrow tissue, neural tissue, brain tissue, organ tissue, and human biopsy tissue.

Figure 6A:
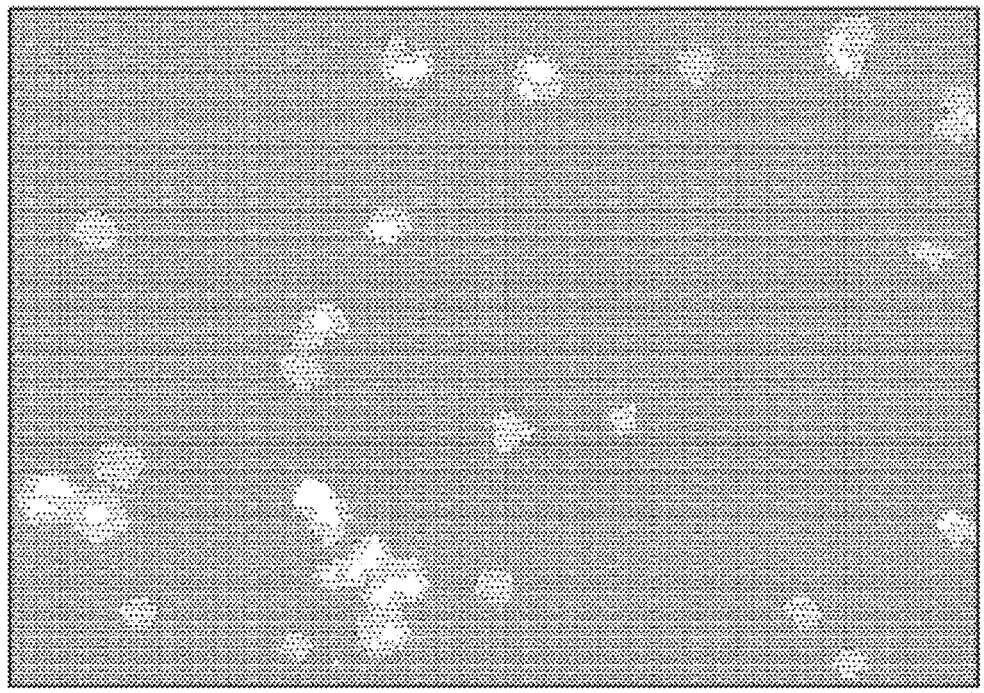
FIGS. 6A and 6B show the bright vesicular staining of the phagosomes filled with the engulfed E. coli within the cells.
Figure 6B:
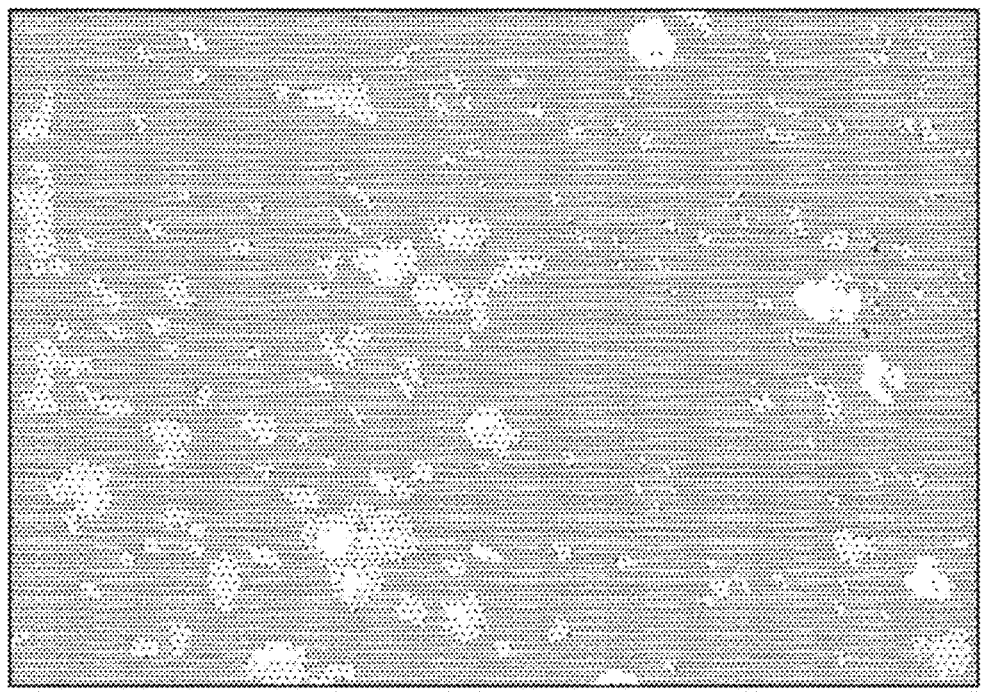

Non-passive accumulation occurs through cell mediated mechanism such as phagocytosis and endocytosis, typically when the present compound comprises a carrier molecule or solid support that is bound by a cellular receptor. In this instance, whenever the present compound is accumulated in the cell or cell compartment by a mechanism that does not rely solely on passive accumulation, the accuracy of a pH measurement will be highest when the pKa of the dye is close to the pH to be measured. The increased accuracy available with the present compounds of the invention in this situation arises from the fact that the pKa is the pH of the aqueous medium containing a species when it is 50% protonated and that at this pH a change in proton intensity will have greatest effect on the properties of the species. Hence, the greatest change in fluorescence intensity occurs at the pKa of the dye, and measurements of absolute fluorescence intensity at this pH so that the present compounds used to analyze a particular cell or cell compartment embraces the pH of that cell or cell compartment is generally sufficient. The compounds of the present invention have been shown to display bright vesicular staining of the phagosomes with engulfed E-coli within the cells (FIGS. 6A and 6B).

Another embodiment of the present invention provides a method for detecting a pH related intracellular process, the method comprising:
  (a) contacting a compound of any one of embodiments described herein with a cell to form a contacted cell;
  (b) incubating the contacted cell to form an incubated solution;
  (c) illuminating the incubated solution to form an illuminated solution; and
  (d) detecting fluorescent emissions from the illuminated solution;
  wherein increased fluorescent emissions indicates activation of the intracellular process.

In a more particular embodiment, the intracellular process is opening of an ion channel. More particular still, the ion channel is calcium.

In another more particular embodiment, the compound is internalized after being incubated to the cytosol of the cell.

Additional embodiments of the present invention provide a no-wash no-quench assay for phagocytosis based on fluorogenic bioparticles made with a novel pH sensitive dye. Current protocols for measuring phagocytosis that use fluorescent bioparticles necessitate a trypan blue quenching step with several washes. These steps can introduce significant variability in the assay. To address this issue, the present invention describes a no-wash phagocytosis kit, using E. coli bioparticles conjugated to a pH sensitive, fluorogenic dye as described herein. These bioparticle conjugates are weakly fluorescent at extracellular pH. However, when added to phagocytic J774.2 murine macrophages, they become ingested into acidic compartments and fluoresce from within the cells, giving specific signals that meet or exceed the brightness of our popular Vybrant™ Phagocytosis Assay Kit. Quantitation of the phagocytic index with these conjugates requires no wash or quenching steps, and uptake of the bioparticles is potently inhibited by cytochalaisin D, a known blocker of phagocytosis. The pH sensitive bioparticles described herein can be used in plate based, as well as imaging and flow cytometry assays of phagocytosis. This dye will also available in an amine reactive form that can be used to label a variety of target molecules in order to follow internalization.

Accordingly, another embodiment of the present invention provides a method for detecting phagocytosis of a carrier molecule in solution, the method comprising:
  (a) conjugating the carrier molecule to a fluorescent pH sensitive dye to form a carrier conjugate;
  (b) contacting the carrier conjugate with a cell to form a contacted cell;
  (c) incubating the contacted cell to form an incubated solution;
  (d) illuminating the incubated solution to form an illuminated solution; and (e) detecting fluorescent emissions from the illuminated solution;

wherein fluorescent emissions indicate phagocytosis of the carrier molecule.

In a more particular embodiment thereof, the fluorescent pH sensitive dye is a compound of Formula I, II, III, IV, V, VI, or VII.

In a more particular embodiment, the carrier molecule is an E. coli bioparticle.

In one particular embodiment, the carrier molecule is beta-amyloid. Researchers have shown that monocytes/macrophages from patients with Alzheimer's Disease have decreased ability to phagocytosis beta amyloid compared to normal patient samples (Fiala et al., Journal of Alzheimer's Disease 7 (2005) 221-232; Zhang et al Journal of Alzheimer's Disease 10 (2006) 1-71 IOS Press). We have shown that beta amyloid conjugated to a pH sensitive dye of the present invention is phagocytosed and can be image by flow cytometry and by microscopy. Thus, a embodiment of the present invention is the detection of phagocytosed beta amyloid, and the subsequent monocytes/macrophages. A particularly important aspect is a blood based diagnostic assay for the detection of Alzheimer's Disease wherein monocytes show a decreased ability to phagocytose beta amyloid conjugated to a present pH sensitive dye compared to normal monocytes. An important control demonstrating that the monocytes are no demonstrating an overall impairment of their phagocytosis function is the E. coli or other bioparticle conjugates of the present pH sensitive dyes. The present dyes are particularly suited for this application because the conjugates are phagocytosed, without binding and fluorescing on the cell surface, and they are easily detected using flow cytometry methods.

Thus, another embodiment of the present invention comprises diagnosing or detecting a disease in a subject, wherein the method comprises (a) contacting a sample obtained from a subject suspected of having the disease with a compound of any of the previous embodiments, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to diagnose or detect the disease.

In a more particular embodiment, the disease is associated with the central nervous system. In another embodiment, the disease is Alzheimer's Disease (AD). In a more particular embodiment, the compound is conjugated to a carrier molecule associated with the disease. In a more particular embodiment, the compound is conjugated to 3-amyloid or a fragment or thereof.

Accordingly, the present invention further provides a blood based assay for Alzheimer's disease, based on the phagocytosis of the present compounds conjugated to beta amyloid protein.

The invention further provides a method for detecting a target molecule capable of modulating a cellular process that effects the pH or directly effects the pH of a cell. In a particular embodiment the target molecule is a small molecule. In another embodiment, the cell is a neuronal cell.

Another embodiment of the present invention provides a method of detecting any one of the following with a compound as described herein: an antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, neuronal cells, noncellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor comprising detecting a compound of claim 4 bound to said antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, noncellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor.

Another embodiment of the invention provides a method for detecting acidic or basic conditions comprising contacting a compound as described herein with a composition suspected of being acidic or basic and detecting the fluorescence of said compound as an indicator of said acidic or basic conditions. In a more particular embodiment, said composition comprises an intracellular environment.

Accuracy for the general means of measuring pH can be further increased by using a plurality of present compounds having different fluorescent responses. For instance, two or more dyes according to the invention may be used, optionally bonded to identical carrier molecules or solid supports, or a dye according to the invention and another dye. In one embodiment, the second fluorescent dye has a positive fluorescence response with increasing pH (by this we mean that the intensity of fluorescence exhibited by the dye or complex increases with increasing pH). It is preferable that the two or more dyes have overlapping titration ranges, and more preferably the different dyes or conjugates have pKa values within about 1 unit of each other. The intensity of fluorescence of each dye or conjugate is then measured, and pH determined by calculating the ratio: fluorescence intensity of the first compound fluorescence intensity of the second compound and comparing the value obtained to a calibration curve.

According to another embodiment of the present invention, the present compounds can be used to analyze the kinetics of migration of a species into or through a cell or cell compartment. This is done by monitoring the intensity of fluorescence of a present compound over a time interval. Where pH is known, the compound should be selected so as to have a pKa in the range between the pH at the starting point and the pH at the end point of the pathway to be analyzed. In some cases it may be desirable to use a plurality of compounds having a variety of pKa values, with each dye or complex tuned to a different portion of the pathway to be analyzed.

Further provided is use of a compound as described herein or a conjugate of a component comprising the same for analysis or detection. More particularly, said detection is by optical means.

Additional aspects of the invention include combinations of any of the embodiments described herein.

Various ancillary materials will frequently be employed in an assay in accordance with the present invention. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In another exemplary embodiment, the kit further comprises molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In another exemplary embodiment, the kit further comprises a member selected from a fixing solution, a detection reagent, a standard, a wash solution, and combinations thereof.

Another embodiment of the invention provides a composition comprising:
(a) a compound of any one the embodiments provided herein; and
(b) an analyte.

In a more particular embodiment the analyte is a cell and the compound is located inside the cell.

In a more particular embodiment the analyte is a protein, lipid or nucleic acid.

In a more particular embodiment the compound is conjugated to a carrier molecule.

Further methods are described in the appended claims.

Illumination

The sample or medium in which the pH sensitive dye is present is illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The dyes of the invention may, at any time after or during an assay, be illuminated with a wavelength of light that results in a detectable optical response, and observed with a means for detecting the optical response. Upon illumination, such as by an ultraviolet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds of the invention includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device. In another embodiment, the illumination source is used to form a covalent bond between the present dye and an analyte of interest. In this instance the dye comprises a photoactivatable reactive group, such as those discussed above.

Kits

Another embodiment of the invention provides a kit for determining the pH of a sample comprising:
(a) a compound of any one of the embodiments provided herein; and
(b) instructions for determining the pH of the sample.

Another embodiment further comprises one or more of the following: a buffering agent, a purification medium, a vial comprising the sample, or an organic solvent.

A detailed description of the invention having been provided above, the following examples are given for the purpose of illustrating the invention and shall not be construed as being a limitation on the scope of the invention or claims.

EXAMPLES

Referring to the examples that follow, compounds of the present invention were synthesized using the methods described herein, or other methods, which are known in the art.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Example 101

Synthesis of pH sensor 104 having the methoxy pKa-enhancing group (Scheme 101).

Scheme 101

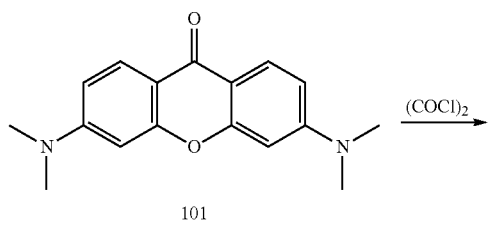

101

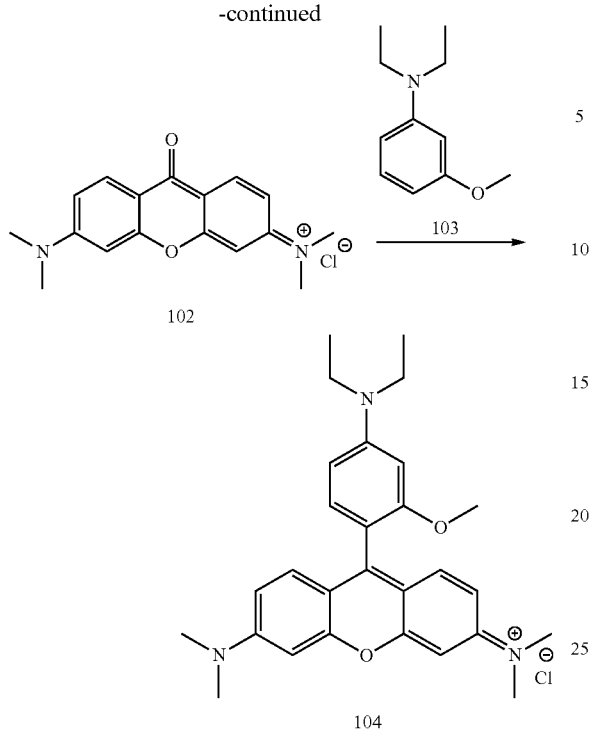

Compound 104.

To a stirred suspension of ketone 101 (94 mg, 0.333 mmol) in dry chloroform (10 mL), oxalyl chloride (30 μL, 0.33 mmol) was added upon cooling to 0-5° C. The resulted red solution was stirred for 1 h, then N,N-diethyl-m-anisidine (60 mg, 0.33 mmol) was added. The reaction was allowed to warm to rt, stirred for 16 h and diluted with CHCl$_3$ (60 mL). Chloroform solution was shaken with sat. NaHCO$_3$ (40 mL) until water layer turned almost colorless. The organic layer was washed with sat. NaHCO$_3$ (20 mL) and extracted with 10% HCl (2×30 mL). The combined acid extract was washed with CHCl$_3$ (2×15 mL; discarded), the aqueous solution was saturated with sodium acetate and extracted with CHCl$_3$ (4×30 mL). The extract was washed with brine (30 mL), and evaporated. The crude product was purified by chromatography on silica gel column (2×40 cm bed, packed with 10% MeOH and 1% AcOH in CHCl$_3$) eluant: 10% MeOH and 1% AcOH in CHCl$_3$ to give the product 104 (3 mg, 2%) as a purple wax.

Example 102

Synthesis of pH sensor 109 having two methoxy pKa-enhancing groups and compound 111 with a labeling succinimidyl ester moiety (Scheme 102).

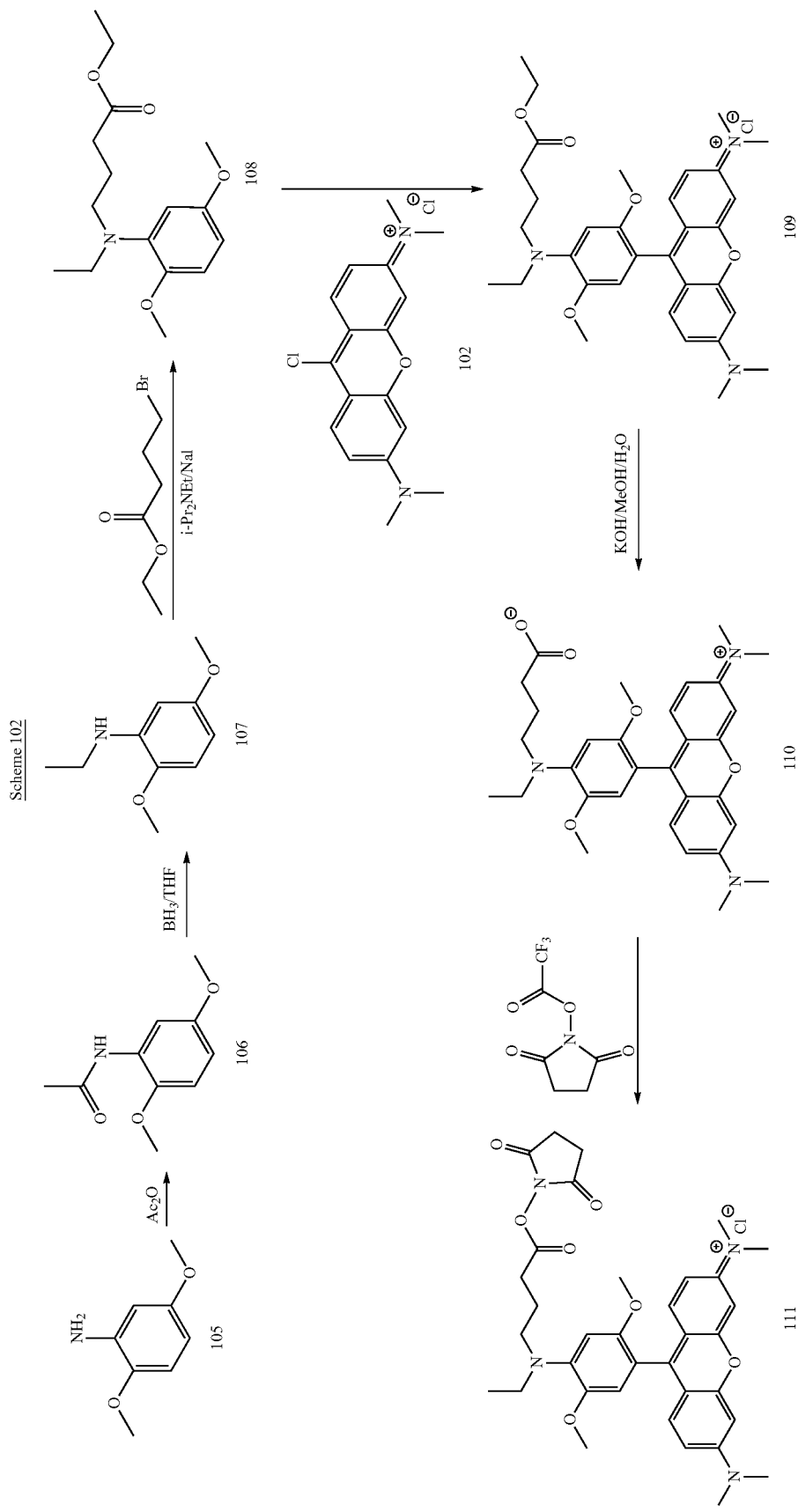

(2,5-Dimethoxyphenyl)acetamide (106)

To a stirred solution of 2,5-dimethoxyaniline (105) (1.00 g, 6.52 mmol) and DIEA (1.71 mL, 9.80 mmol) in CHCl$_3$ (20 mL) was added acetic anhydride (0.93 mL, 9.8 mmol). The reaction mixture was stirred for 1.5 h, washed with water (50 mL), 5% 5 HCl (50 mL), brine (50 mL), dried over Na$_2$SO$_4$, and evaporated to give acetate 106 (1.33 g, 100%) as a dark oil.

2,5-Dimethoxy-N-ethylaniline (107)

To the solution of acetamide 106 (1.27 g, 6.5 mmol) in dry THF (10 mL) a borane-THF complex (1M in THF, 58.5 mL, 58.5 mmol) was added upon ice-water cooling. The mixture was allowed to warm to rt and stirred under reflux for 16 h. The mixture was cooled to 0° C. and carefully decomposed with MeOH (40 mL), and then the mixture was heated to reflux and stirred for 1 h. Upon cooling, the solution was concentrated and the residue was co-evaporated with MeOH (3×20 mL) to give amine 107 (1.22 g, 100%) as a dark oil.

Ethyl 4-((2,5-dimethoxyphenyl)(ethyl)amino)butanoate (108)

2,5-Dimethoxy-N-ethylaniline (107) (1.22 g, 6.73 mmol), DIEA (3.5 mL, 20 mmol), ethyl 4-bromobutyrate (4.86 mL, 33.6 mmol), and sodium iodide (0.504 g, 3.34 mmol, catalyst) in DMF (10 mL) were stirred at 70° C. for 16 h. The reaction mixture was cooled to rt, diluted with EtOAc (50 mL), washed with water (4×50 mL), brine (50 mL), dried over Na$_2$SO$_4$ and evaporated. The residue was purified by chromatography on a silica gel column (2.5×40 cm bed, packed with EtOAc/Hexanes (1:4)), eluant: EtOAc/hexanes (1:4) to provide compound 108 (1.39 g, 70%) as a yellowish oil.

Compound 109.

To a stirred suspension of ketone 102 (0.600 g, 2.13 mmol) in dry CHCl$_3$ (10 mL), oxalyl chloride (0.19 mL, 2.13 mmol) was added upon cooling to 0-5° C. The resulted red solution was stirred for 0.5 h, then ester 108 (0.629 g, 2.13 mmol) was added. The reaction was allowed to heat to rt, stirred for 16 h and diluted with CHCl$_3$ (300 mL). Chloroform solution was shaken with sat. NaHCO$_3$ (250 mL) until water layer turns almost colorless. The organic layer was extracted with 10% HCl (4×150 mL). The combined acid extract was saturated with sodium acetate and extracted with CHCl$_3$ (10×100 mL). The extract was washed with brine (300 mL), dried over Na$_2$SO$_4$ and evaporated. The crude product was purified by chromatography on silica gel column (5×50 cm bed, packed with MeCN/H$_2$O/AcOH (8:2:2.5)) eluant: MeCN/H$_2$O/AcOH (8:2:2.5) to give the product 109 (0.419 g, 33%) as a purple solid.

Acid 110.

The solution of ester 109 (0.400 g, 0.710 mmol) and 1M KOH (35 mL, 35 mmol) in 45 mL of MeOH was stirred for 1 h, then acetic acid (8 mL) was added and the mixture was diluted with 100 mL of brine. The product was extracted with CHCl$_3$ (3×50 mL). The combined extract was evaporated, the residue was co-evaporated with MeOH/toluene and dried in vacuum to give acid 110 (0.079 g, 21%) as a purple solid.

Succinimidyl Ester 111.

To the solution of acid 110 (79 mg, 0.15 mmol) and DIEA (78 µL, 0.45 mmol) in DMF (2 mL) was added N-hydroxysuccinimide trifluoroacetate (94 mg, 0.44 mmol) and the reaction mixture was stirred for 30 min at rt, diluted with CHCl$_3$ (120 mL) and washed with water (5×40 mL), and brine (20 mL). The solution was evaporated and residue was co-evaporated with CHCl$_3$/toluene mixture. The residue was dissolved in CHCl$_3$ (10 mL); 1 mL of acetic acid and 5 mL of toluene were added and mixture was evaporated. The residue was re-dissolved in chloroform (20 mL), the solution was filtered and concentrated to 1 mL. The ether (20 mL) was added, and purple precipitate was filtered and dried in vacuum to give ester 111 (72 mg, 73%).

Example 103

Synthesis of pH sensor 118 having methoxy pKa-enhancing group and compound 120 with a labeling succinimidyl ester moiety (Scheme 103).

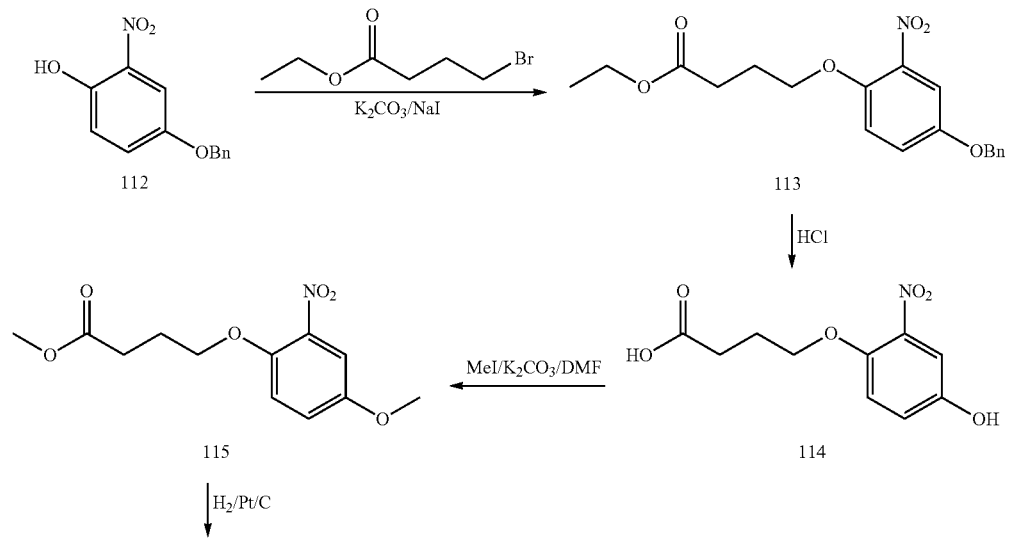

Scheme 103

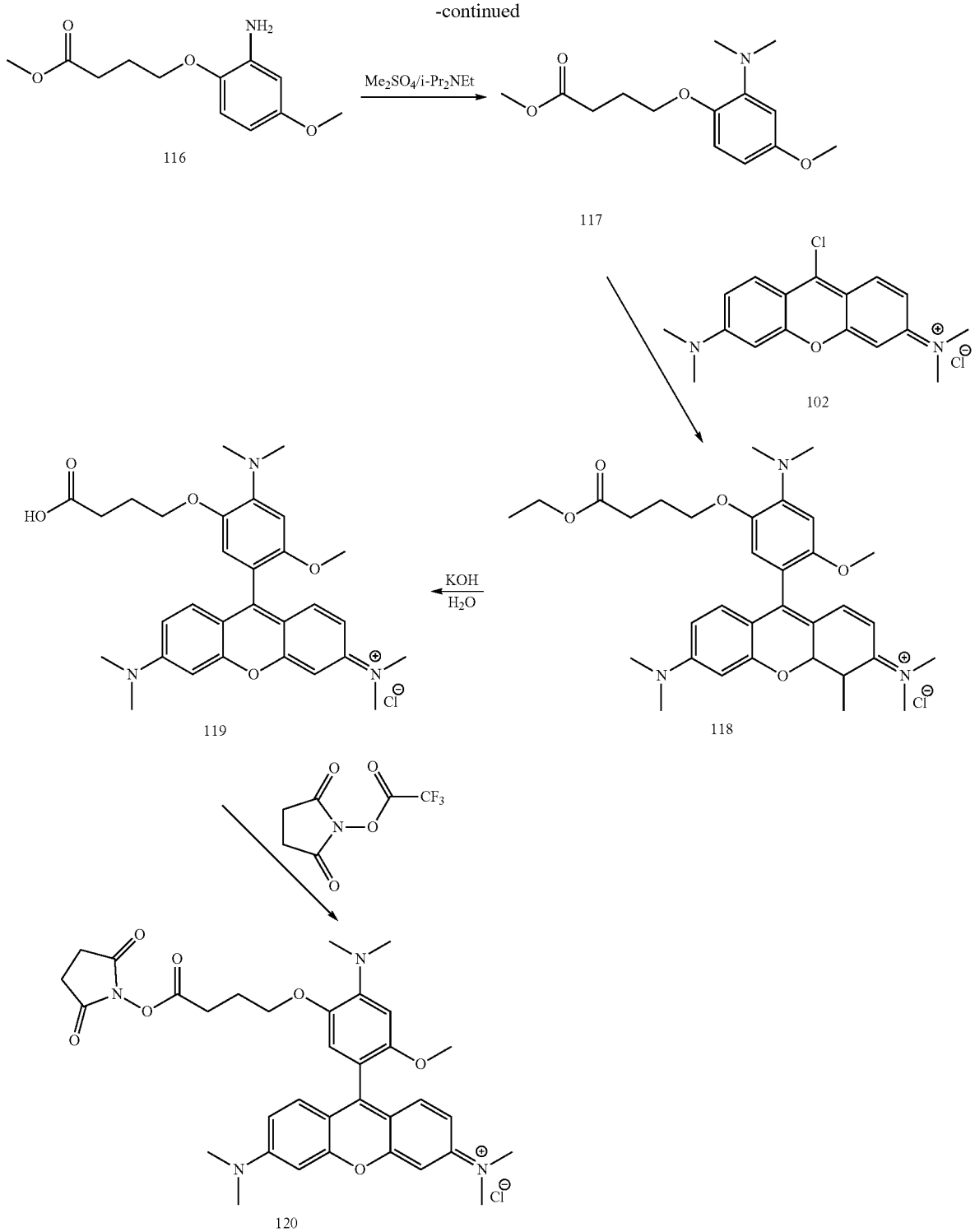

Ethyl 4-(4-benzyloxy-2-nitrophenyloxy)butanoate (113)

4-(Benzyloxy)-2-nitrophenol (112) (2.00 g, 9.39 mmol), K₂CO₃ (1.30 g, 9.42 mmol), NaI (0.70 g, 4.7 mmol) and ethyl 4-bromobutyrate (2.70 mL, 18.7 mmol) in DMF (10 mL) were stirred for 3 hrs at 70° C. The reaction mixture was cooled to rt, diluted with EtOAc (100 mL), washed with water (4×40 mL), 5% HCl (3×40 mL), brine (30 mL), dried over Na₂SO₄ and evaporated to give ester 113 (2.10 g, 62%) as a brown oil.

4-(4-Hydroxy-2-nitrophenyloxy)butanoic Acid (114)

Ester 113 (1.50 g, 4.17 mmol) was stirred under reflux with 30 mL of water and 30 mL of conc HCl for 1.5 hrs.

Upon cooling the mixture was diluted with water (150 mL) and extracted with EtOAc (3×40 mL). The extract was washed with brine (50 mL), dried over $Na_2SO_4$ and evaporated. The crude product was dissolved in 1M KOH (30 mL), extracted with EtOAc (3×30 mL; discarded), acidified with 10% HCl to pH 4 and extracted with EtOAc (4×40 mL). The extract was washed with brine (40 mL), dried over $Na_2SO_4$ and evaporated to give acid 114 (1.30 g) as a brown solid.

Methyl 4-(4-methoxy-2-nitrophenyloxy)butanoate (115)

To a solution of acid 114 (1.30 g, 5.4 mmol) in DMF (10 mL) a powdered $K_2CO_3$ (1.50 g, 10.9 mmol) was added followed by the addition of MeI (1.4 mL, 27 mmol). The resulting mixture was stirred for 2.5 h, diluted with of water (100 mL) extracted with EtOAc (3×40 mL). The extract was washed with water (4×40 mL), 1M KOH (50 mL), water (2×40 mL), 10 HCL (2×30 mL), water (2×40 mL), brine (40 mL). The solution was dried over $Na_2SO_4$ and evaporated to give ester 115 (1.36 g) as brown oil.

Methyl 4-(2-amino-4-methoxyphenyloxy)butanoate (116)

Compound 115 (1.36 g, 5.05 mmol) was hydrogenated for 16 h in Parr apparatus in $CH_2Cl_2$ (20 mL) over 10% Pt/C (20 mg, catalyst) at 50 psi hydrogen pressure. The catalyst was filtered off and the solution was evaporated. The residue was purified by chromatography on silica gel column (2×30 cm bed, packed with EtOAc/hexanes (1:2)), eluant: EtOAc/hexanes (1:2) to give aniline 116 (1.07 g, 100% from ester 113) as a yellow oil.

Methyl 4-(2-dimethylamino-4-methoxyphenyloxy)butanoate (117)

To a solution of aniline 116 (0.617 g, 2.31 mmol) in MeCN (15 mL) was added DIEA (1.61 mL, 9.24 mmol) followed by dimethyl sulfate (DMS) (1.75 mL, 18.5 mmol), and the mixture was stirred for 5 h. The excess of DMS was quenched by stirring with ammonium hydroxide (5 mL) for 16 h. The resulting mixture was diluted with water (100 mL) and the product was extracted with EtOAc (3×40 mL). The extract was washed with water (2×30 mL), brine (30 mL), dried over $Na_2SO_4$ and evaporated. The residue was purified by chromatography on silica gel column (2×35 cm bed, packed with EtOAc/hexanes (1:3)), eluant: EtOAc/hexanes (1:3) to give N,N-dimethylaniline derivative 117 (0.189 g, 31%) as a clear oil.

Compound 118.

To a stirred suspension of ketone 101 (0.200 g, 0.709 mmol) in dry $CHCl_3$ (30 mL), oxalyl chloride (60 μL, 0.71 mmol) was added upon cooling to 0-5° C. The resulted red solution was stirred for 0.5 h, then ester 117 (0.189 g, 0.708 mmol) was added. The reaction was allowed to heat to rt, stirred for 72 h and diluted with $CHCl_3$ (80 mL). Chloroform solution was shaken with sat. $NaHCO_3$ (100 mL) until aqueous layer turns almost colorless. The organic layer was washed with brine (50 mL), filtered through paper filter and evaporated. The crude product was purified by chromatography on silica gel column (2×40 cm bed, packed with $MeCN/H_2O/AcOH$ (8:2:2.5)) eluant: $MeCN/H_2O/AcOH$ (8:2:2.5) to give the compound 118 (0.137 g, 33%) as a purple solid.

Acid 119.

The solution of ester 118 (0.137 g, 0.235 mmol) and 1M KOH (12 mL, 12 mmol) in 20 mL of MeOH was stirred for 0.5 h, then acetic acid (4 mL) was added and the mixture was diluted with 100 mL of brine. The product was extracted with $CHCl_3$ (4×40 mL). The combined extracts were washed with brine (100 mL), filtered through paper filter and evaporated; the residue was co-evaporated with $CHCl_3$/toluene and dried in vacuum to give acid 119 (28 mg, 23%) as a purple solid.

Succinimidyl Ester 120.

To the solution of acid 119 (28 mg, 0.051 mmol) and DIEA (28 μL, 0.149 mmol) in DMF (1 mL) was added N-hydroxysuccinimide trifluoroacetate (32 mg, 0.15 mmol) and the reaction was stirred for 0.5 h, diluted with $CHCl_3$ (80 mL) and washed with water (5×30 mL), and brine (30 mL). The solution was evaporated and residue was co-evaporated with $CHCl_3$/toluene mixture. The residue was re-dissolved in of $CHCl_3$ (5 mL); 0.5 mL AcOH and 3 mL of toluene were added and mixture was evaporated. The residue was re-dissolved in chloroform (20 mL), the solution was filtered and concentrated to 1 mL. The ether (20 mL) was added, and purple precipitate was filtered and dried in vacuum to give ester 120 (25 mg, 75%) as a dark purple solid.

Example 104

Synthesis of pH sensor 127 having methoxy- and dimethylamino pKa-enhancing groups and compound 129 with a labeling succinimidyl ester moiety (Scheme 104).

Scheme 104

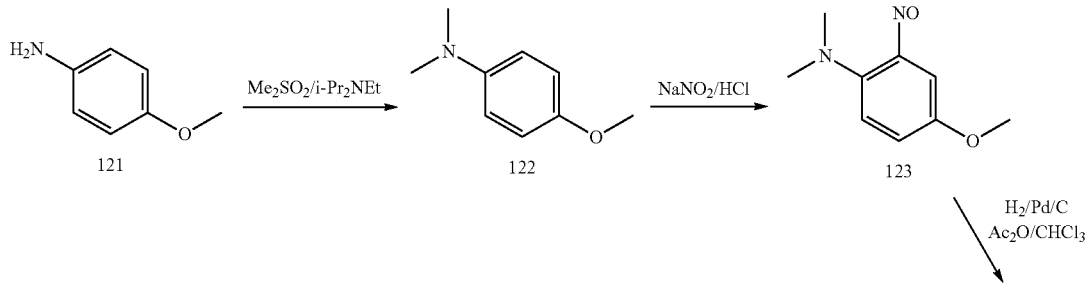

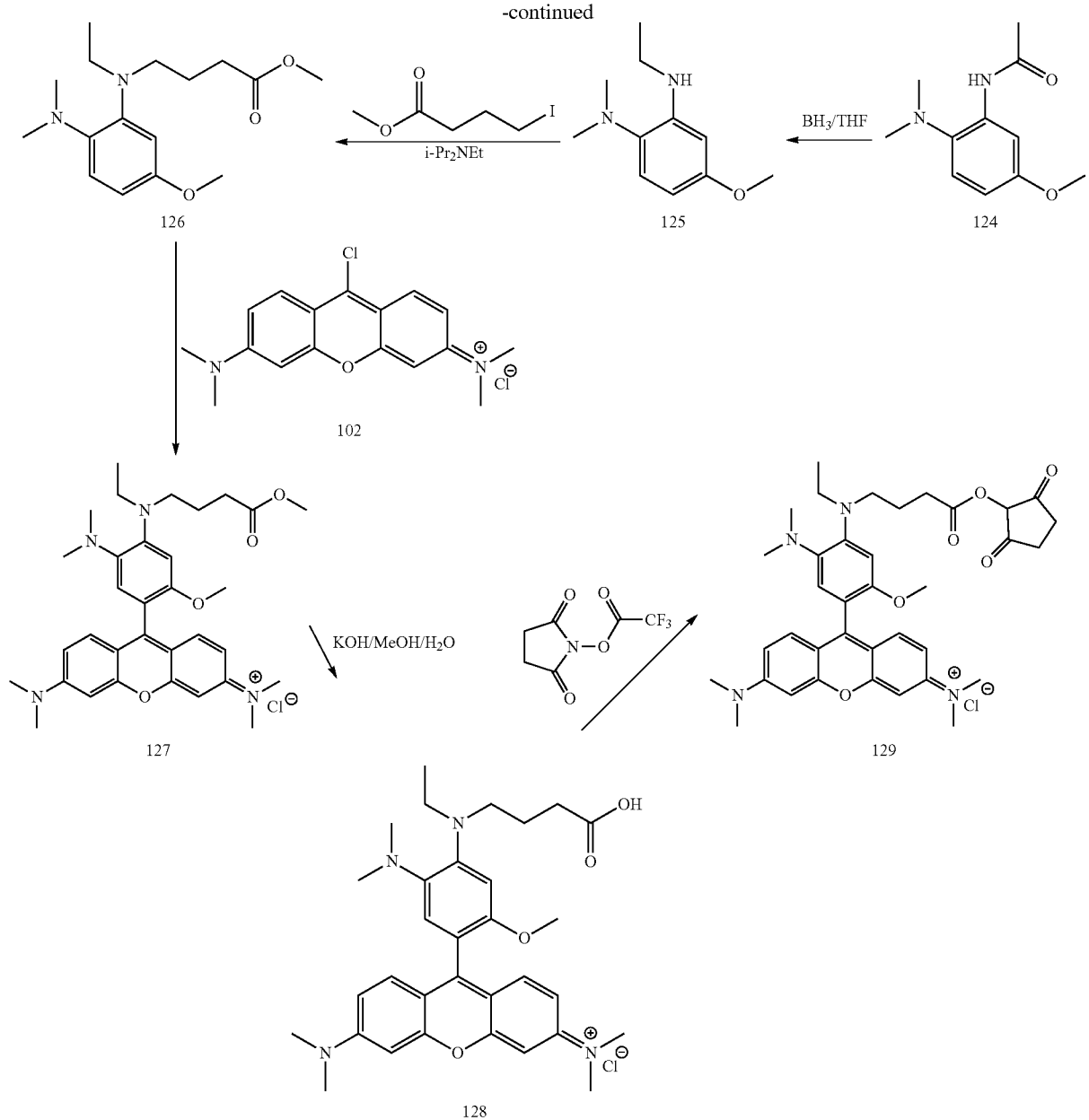

N,N-Dimethylanisdine (122).

To the stirred solution of p-anisidine 121 (20.0 g, 162 mmol) and DIEA (113 mL, 650 mmol) in CH$_3$CN (600 mL), DMS (31 mL, 325 mmol) was added upon ice/water bath cooling. After stirring for 2 h another portion of DMS (31 mL, 325 mmol) was introduced, and the reaction was continued for more 0.5 h. The mixture was extracted with hexanes (6×500 mL). The combined hexanes extract was evaporated and the residue was purified by chromatography on silica gel column (6×50 cm bed, packed in CHCl$_3$/EtOAc (10:1)), eluant: CHCl$_3$/EtOAc (10:1) to give N,N-dimethylanisidine 122 (4.54 g, 19%) as a brown solid.

4-(N,N-dimethylamino)-3-nitrosoanisole (123)

To a stirred solution of N,N-dimethylanisidine 122 (3.09 g, 20.4 mmol) in 5% HCl (30 mL), NaNO$_2$ (1.94 g, 28.2 mmol) in 10 mL water was added dropwise upon ice/water bath cooling, and reaction was stirred for 15 min. The mixture was poured in 200 mL of 3N NaOAc (200 mL) and extracted with EtOAc (3×150 mL). The combined extract was washed with sat. NaHCO$_3$ (200 mL), brine (200 mL), dried over Na$_2$SO$_4$ and evaporated to give nitroso derivative 123 (3.68 g, 100%) as brown solid.

N-(2-Dimethylamino-5-methoxyphenyl)acetamide (124)

Nitroso derivative 123 (1.36 g, 5.05 mmol) was hydrogenated for 2 h in Parr apparatus in CHCl$_3$ (20 mL) over 10% Pt/C (360 mg, catalyst) at 45 psi hydrogen pressure. The hydrogenation flask was disconnected from apparatus and the stirring bar was inserted. The flask was cooled in ice/water bath, K$_2$CO$_3$ (8.45 g, 61.3 mmol) was introduced followed by the addition of acetyl chloride (2.9 mL, 40.8 mmol). The mixture was stirred for 0.5 h, MeOH (5 mL) was added, the solids were filtered off and the filtrate was evaporated. The residue was purified by chromatography on silica gel column (2×30 cm bed, packed with EtOAc/hexanes (3:2)), eluant: EtOAc/hexanes (3:2) to give amide 124 (3.08 g, 72%) as a glassy foam.

2-Dimethylamino-5-methoxy-N-ethylaniline (125)

To a stirred solution of N-(2-dimethylamino-5-methoxyphenyl)acetamide (124) (3.70 g, 17.80 mmol) in THF (20 mL), the $BH_3$-THF complex (1N, 89 mL, 89 mmol) was added, and the reaction was refluxed under stirring for 16 h. Upon cooled to 60° C., it was carefully decomposed by slow addition of methanol (100 mL), and heated again to a gentle reflux (70° C.). The mixture was refluxed for 1 h to destroy the amine-borane complexes, cooled to rt, evaporated and co-evaporated with methanol (2×100 mL).

The residue was dissolved in ethyl acetate (200 mL), and washed with sodium bicarbonate solution (3×200 mL), brine (200 mL), dried over $MgSO_4$, and evaporated to get the compound 125 (3.30 g, 96%) as a tan oil.

Methyl 4-((2-dimethylamino)-5-methoxyphenyl)
(ethyl)amino)butanoate (126)

2-Dimethylamino-5-methoxy-N-ethylaniline (125) (1.70 g, 8.80 mmol), DIEA (3.1 mL, 17 mmol), and methyl 4-iodobutyrate (2.4 mL, 17 mmol) in DMF (10 mL) were stirred at 70° C. for 24 h. The reaction mixture was cooled to rt, diluted with EtOAc (60 mL), washed with water (4×50 mL), brine (75 mL), dried over $Na_2SO_4$ and evaporated. The residue was purified by chromatography on a silica gel column (2.5×30 cm bed, packed with $CHCl_3$), eluant: 5% MeOH in $CHCl_3$ to get compound 126 (2.24 g, 86%) as a dark amber oil.

Methyl 4-((2-dimethylamino)-5-methoxyphenyl-4-tetramethylrhodaminyl)(ethyl)amino) Butanoate (127)

To a stirred suspension of tetramethylrhodamine ketone 101 (0.96 g, 3.4 mmol) in 50 mL of dry chloroform was added oxalyl chloride (0.30 mL, 3.4 mmol) upon cooling to 0-5° C. The resulting red solution was stirred for 0.5 h at 5° C., and the solution of compound 126 (1.00 g, 3.40 mmol) in dry chloroform (5 mL) was introduced. The reaction was allowed to heat to rt, stirred for 72 h, diluted with $CHCl_3$ (50 mL), and stirred for 30 min with sat. $NaHCO_3$ (300 mL) and solid $NaHCO_3$ (10 g). The organic layer was extracted with 10% HCl (3×50 mL). The combined acid extract was washed with $CHCl_3$ (3×50 mL; discarded), saturated with sodium acetate and extracted with $CHCl_3$ (5×50 mL). The extract was washed with brine (300 mL), dried over $Na_2SO_4$ and evaporated. The crude product was purified by chromatography chromatography on silica gel column (2×50 cm bed, packed with $CHCl_3$/MeOH/AcOH/$H_2O$ (100:20:5:1)), eluant: $CHCl_3$/MeOH/AcOH/$H_2O$ (100:20:5:1) to give the product 127 (0.76 g, 37%) as a purple solid.

4-((2-Dimethylamino)-5-methoxyphenyl-4-tetramethylrhodaminyl)(ethyl)amino) Butanoic Acid (128)

To the solution of the methyl ester 132 (75 mg, 0.277 mmol) in 25 mL of methanol was added 20 ml (20 mmol) of 1M KOH. The reaction was stirred 30 min and the acetic acid (10 mL) was added. The mixture was extracted with $CHCl_3$ (3×30 mL), and combined extract was washed with brine (20 mL), filtered through the paper filter and evaporated. The residue was co-evaporated with MeOH/toluene mixture to give the compound 128 (19 mg, 13%) as a purple solid.

Succinimidyl 4-((2-Dimethylamino)-5-methoxyphenyl-4-tetramethylrhodaminyl)(ethyl)amino) Butanoate (129)

To a solution of the acid 128 (60 mg, 0.11 mmol) in DMF (2 mL) and DIEA (58 µL, 0.33 mmol) was added N-hydroxysuccinimide trifluoroacetate (70 mg, 0.33 mmol). The reaction mixture was stirred for 30 min, diluted with chloroform (100 mL) and washed with water (5×50 mL), brine (50 mL), filtered through paper and concentrated in vacuum. The crude product was purified by precipitation from $CHCl_3$ solution (5 mL) with ether (20 mL) to give compound 129 (60 mg, 83%) as a purple powder.

Example 105

Synthesis of pH sensor 133 having methoxy- and dimethylamino pKa-enhancing groups and compound 129 with a labeling succinimidyl ester moiety (Scheme 105).

Scheme 105

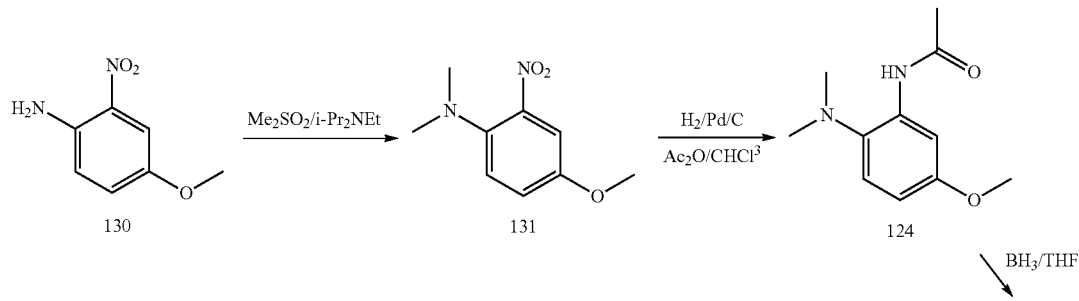

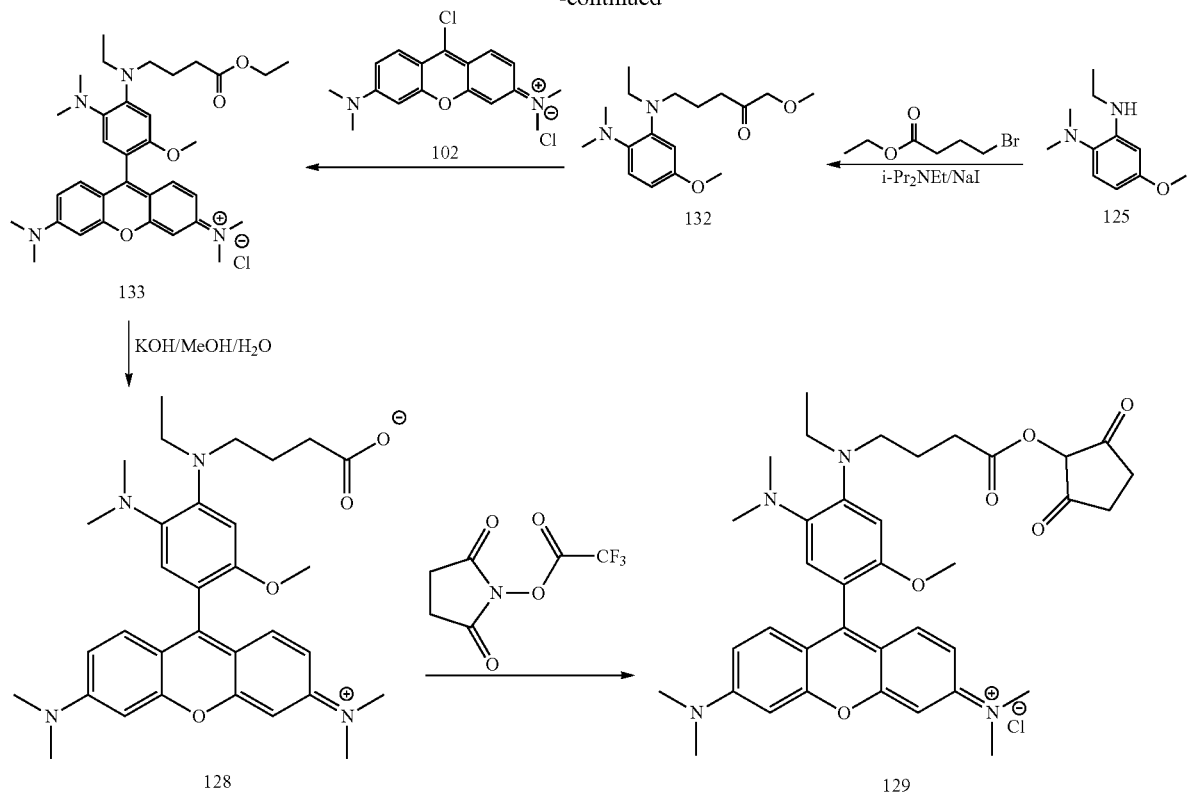

4-Methoxy-2-nitro-N,N-dimethylaniline (131)

4-Methoxy-2-nitroaniline 130 (8.41 g, 50.0 mmol), DIEA (17.5 mL, 100 mmol), and DMS (28.5 mL, 300 mmol) in MeCN (100 mL) were stirring under reflux for 6 h. After cooling to rt, conc. ammonium hydroxide solution (100 mL) was added and the reaction mixture was stirred for 2 h to destroy the excess of DMS. The mixture was evaporated to give an oily residue, which was partitioned between CHCl$_3$ (200 mL) and water (200 mL). The aqueous phase was extracted with CHCl$_3$ (5×50 mL), the combined chloroform solution was washed with brine, dried over MgSO$_4$ and evaporated to give the compound 131 (6.20 g, 63%) as a red oil, solidified upon standing.

N-(2-Dimethylamino-5-methoxyphenyl)acetamide (124)

4-Methoxy-2-nitro-N,N-dimethylaniline (131) (8.00 g, 40.8 mmol) was hydrogenated for 20 h in Parr apparatus in CHCl$_3$ (100 mL) and acetic anhydride (50 mL) over 10% Pd/C catalyst (1.8 g) at 40-45 psi hydrogen pressure. The catalyst was filtered off, and the filtrate was rotoevaporated using 20 mm to 5 mm Hg vacuum. The crude product was purified by chromatography on a silica gel column (12×60 cm bed, packed with EtOAc/Hexanes (2:3)), eluant: EtOAc/hexanes (1:1) to get compound 124 (5.05 g, 60%) as a yellowish oil

2-Dimethylamino-5-methoxy-N-ethylaniline (125)

was prepared from N-(2-dimethylamino-5-methoxyphenyl)acetamide (124) as it is described in the example 104.

Ethyl 4-((2-dimethylamino)-5-methoxyphenyl)(ethyl)amino)butanoate (132)

2-Dimethylamino-5-methoxy-N-ethylaniline (125) (4.13 g, 21.3 mmol), DIEA (12.0 mL, 68.4 mmol), ethyl 4-bromobutyrate (16.5 mL, 114 mmol), and sodium iodide (1.71 g, 1.14 mmol, catalyst) in DMF (25 mL) were stirred at 70° C. for 24 h. The reaction mixture was cooled to rt, diluted with EtOAc (150 mL), washed with water (4×150 mL), brine (150 mL) and evaporated.

The residue was purified by chromatography on a silica gel column (4.5×40 cm bed, packed with EtOAc/Hexanes (1:4)), eluant: EtOAc/hexanes (1:4) to get compound 132 (5.50 g, 76%) as a yellowish oil.

Ethyl 4-((2-dimethylamino)-5-methoxyphenyl-4-tetramethylrhodaminyl)(ethyl)amino) Butanoate (133)

To a stirred suspension of tetramethylrhodamine ketone 101 (0.96 g, 3.40 mmol) in 50 mL of dry chloroform was added oxalyl chloride (0.30 mL, 3.4 mmol) upon cooling to 0-5° C. The mixture was stirred for 1 h at 5° C., and the solution of compound 132 (1.00 g, 3.40 mmol) in dry chloroform (5 mL) was introduced. The reaction mixture was allowed to heat to rt, stirred for 72 h, diluted with CHCl$_3$ (50 mL), and stirred for 30 min with sat. NaHCO$_3$ (300 mL) and solid NaHCO$_3$ (10 g).

The organic layer was separated, washed with water (50 mL), brine (50 mL), filtered through paper filter and evaporated. The crude product was purified by chromatography on a silica gel column (2.5×40 cm bed, packed with CHCl$_3$/

MeOH/AcOH/H₂O (800:80:40:5), and using the same mixture as eluant to get compound 133 (0.169 g, 8%) as a dark purple-red oil.

4-((2-Dimethylamino)-5-methoxyphenyl-4-tetramethylrhodaminyl)(ethyl)amino) Butanoic Acid (128)

To the solution of the ethyl ester 133 (0.151 g, 0.277 mmol) in 20 mL of methanol was added 14 ml (14 mmol) of 1M KOH. The reaction was stirred 30 min and the acetic acid (5 mL) was added, followed by brine (80 mL). The mixture was extracted with CHCl₃ (5×40 mL), and combined extract was washed with brine (50 mL), filtered through the paper filter and evaporated get the compound 128 (0.116 g, 77%) as a purple solid.

Succinimidyl 4-((2-Dimethylamino)-5-methoxyphenyl-4-tetramethylrhodaminyl)(ethyl)amino) Butanoate (129)

was prepared from the acid 128 as it is described in example 104.

Example 106

Synthesis of pH sensor 134 having maleimide labeling moiety (Scheme 106).

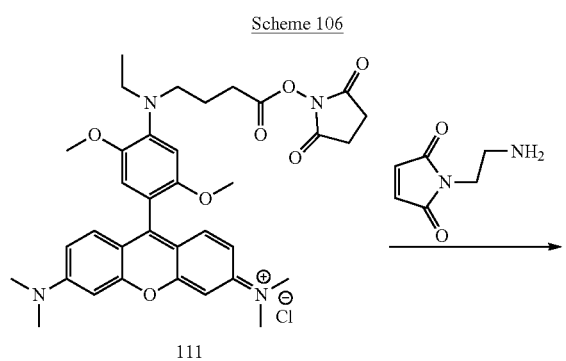

Scheme 106

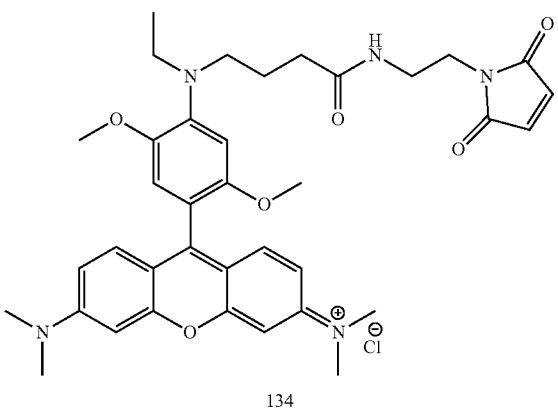

134

Maleimide Derivative 134.

To a solution of succinimidyl ester 111 (5 mg, 0.007 mmol) and DIEA (5 μL, 0.028 mmol) in of DMF (1 mL) was added 1-(2-aminoethyl)-1H-pyrrole-2,5-dione trifluoroacetate (3 mg, 0.012 mmol). The reaction solution was stirred for 40 min, then evaporated to dryness. The residue was purified by preparative reverse-phase TLC using (H₂O/2-PrOH (1:1)+0.4% TFA) mixture as eluant to give compound 134 (5 mg, 95%) as a purple solid.

Example 107

Synthesis of pH sensor 135 having hydrocarbon lipophilic moiety (Scheme 107).

Scheme 107

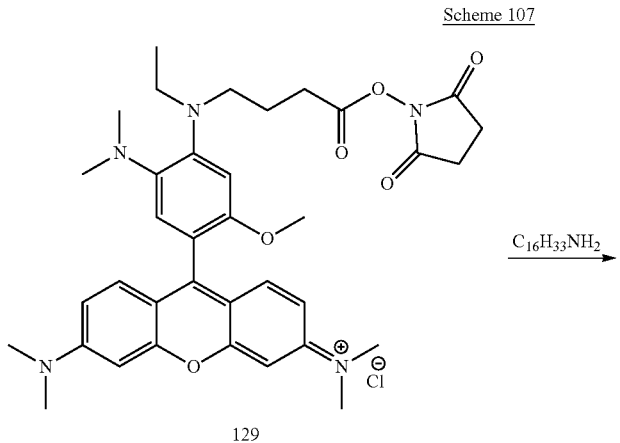

129

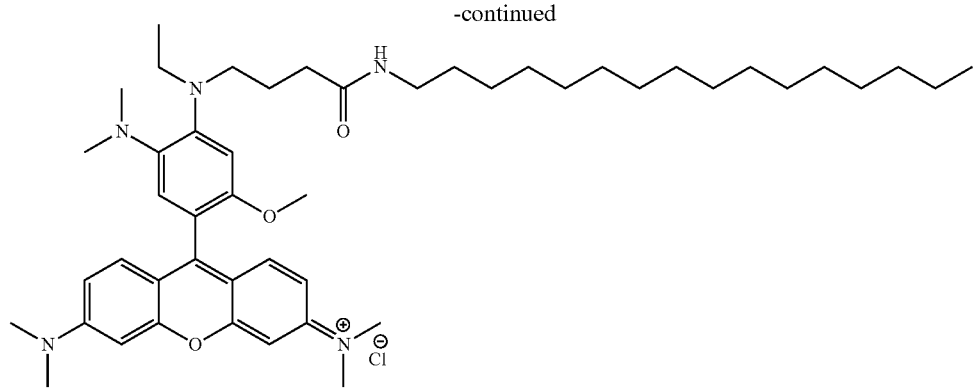

135

Compound 135.

The mixture of succinimidyl ester 129 (4.6 mg, 0.0068 mmol), DIEA (24 μL, 0.0138 mmol) and 1-hexadecylamine (21 mg, 0.0087 mmol) in DMF (1 mL) and CHCl₃ (2 mL) was stirred for 30 min, then diluted with chloroform (80 mL), washed with water (4×40 mL), brine 40 (mL), filtered through paper filter and evaporated. The residue was purified by chromatography on silica gel column (0.5×8 cm, packed with CHCl₃/MeOH/AcOH/H₂O (20:5:5:1)), eluant: CHCl₃/MeOH/AcOH/H₂O (20:5:5:1) to give amide 135 (4 mg, 73%) as a purple gum.

Example 108

Synthesis of pH sensor 136 having PEG linker and compound 137 with a labeling succinimidyl ester moiety. (Scheme 108).

Scheme 108

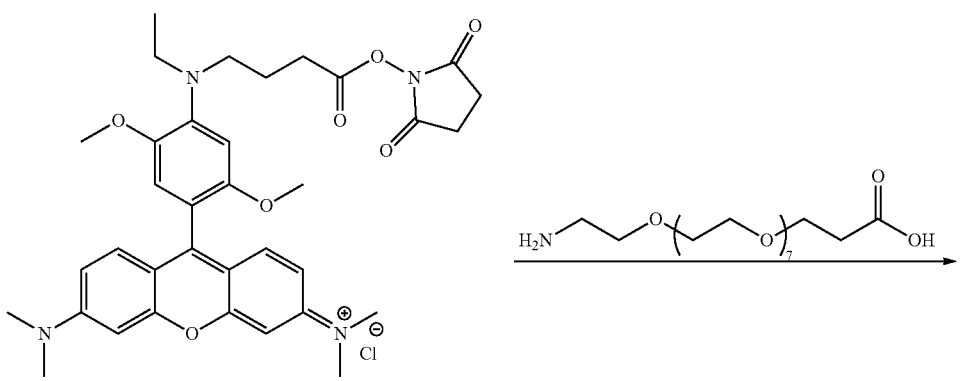

111

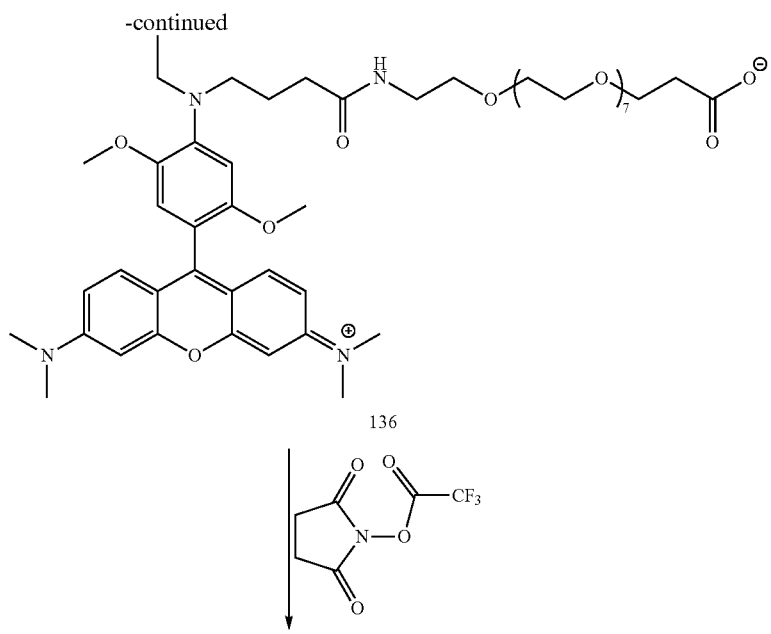

136

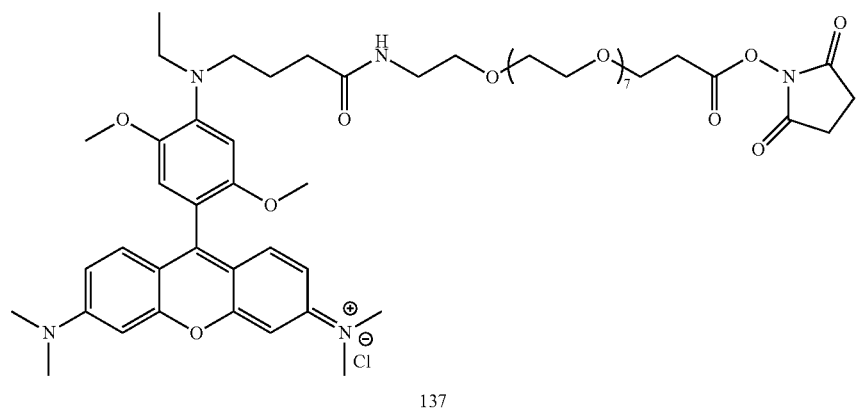

137

PEG-Carboxylate 136.

The mixture of succinimidyl ester 111 (5 mg, 0.007 mmol), amino-dPEG$_8$-acid (5 mg, 0.011 mmol), and DIEA (4 µL, 0.023 mmol) in 1 mL of DMF was stirred for 0.5 h and evaporated do dryness. The residue was dissolved in water (50 mL) and extracted with chloroform (3×50 mL). The combined extract was washed with brine (50 mL), filtered through paper filter and evaporated to give compound 136 (6 mg, 86%) as a purple powder.

Succinimidyl Ester 137.

Compound 136 (6 mg, 0.007 mmol) was stirred with DIEA (4 µL, 0.023 mmol) and N-hydroxysuccinimidyl trifluoroacetate (0.0044 g, 0.021 mmol) in DMF (1 mL) for 20 min. The reaction mixture was diluted with chloroform (100 mL), washed with water (6×40 mL), brine (40 mL) and evaporated. The residue was co-evaporated with chloroform/toluene, re-dissolved in CHCl$_3$ (10 mL) and AcOH (1 mL), diluted with toluene (5 mL) and evaporated. The residue was washed with ether and dried to give compound 137 (6 mg, 79%) as a purple gum.

Example 109

Synthesis of pH sensor 138 having C$_5$-amide linker and compound 139 with a labeling succinimidyl ester moiety. (Scheme 109).

Scheme 109

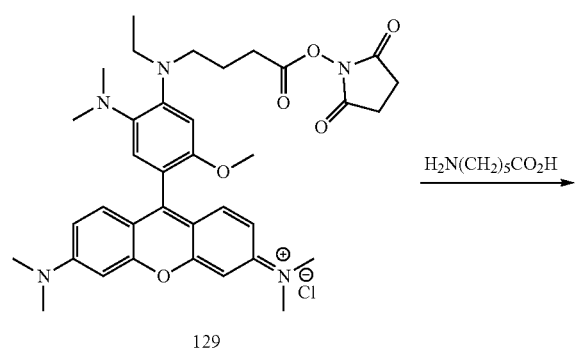

129

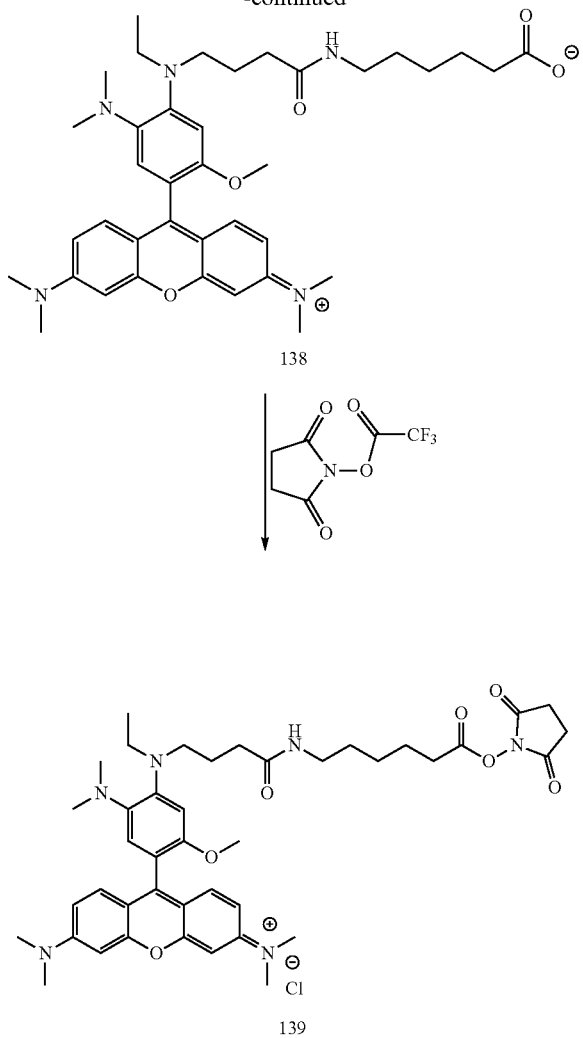

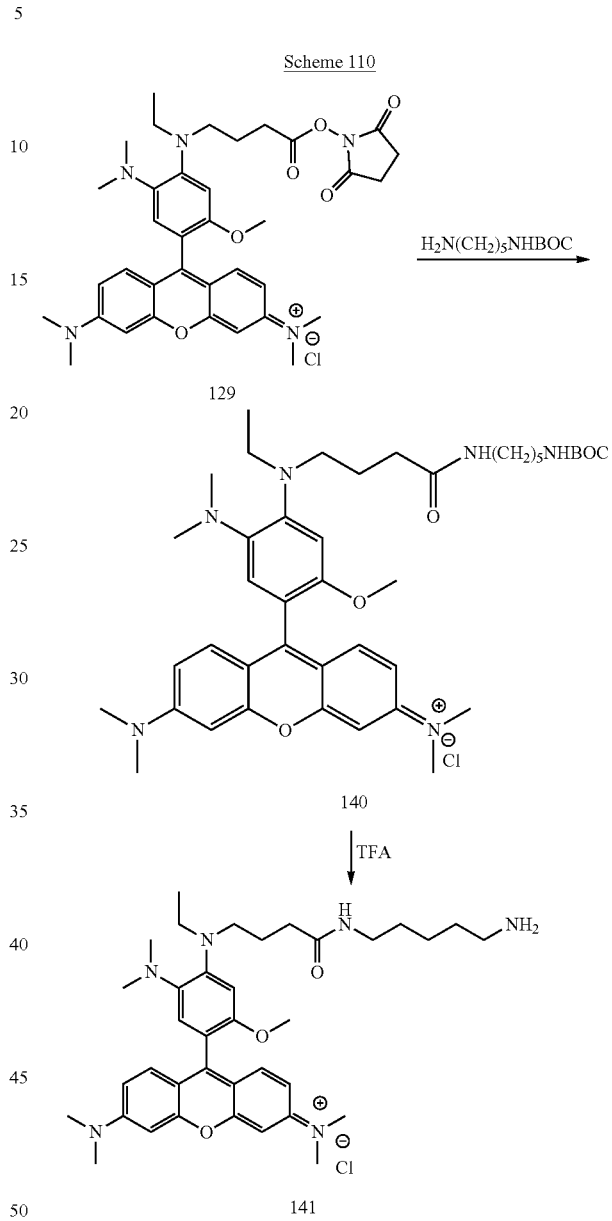

Example 110

Synthesis of pH sensor 141 having aliphatic amino group (Scheme 110).

Scheme 110

Carboxylate 138.

To a stirred solution of succinimidyl ester 129 (5 mg, 0.007 mmol) and DIEA (4 µL, 0.023 mmol) in DMF (1 mL) was added 6-aminocaproic acid (15 mg, 0.011 mmol) in water (0.2 mL). The reaction mixture was stirred for 20 min, diluted with brine (50 mL) and was extracted with chloroform (4×30 mL). The combined extract was washed with brine (30 mL), filtered through paper filter and evaporated. The residue was co-evaporated with chloroform/toluene to give compound 138 (4 mg, 82%) as a purple solid.

Succinimidyl Ester 139.

Compound 138 (5 mg, 0.0073 mmol) was stirred with DIEA (4 µL, 0.023 mmol) and N-hydroxysuccinimidyl trifluoroacetate (0.0046 g, 0.022 mmol) in DMF (1 mL) for 30 min. The reaction mixture was diluted with chloroform (80 mL), washed with water (5×45 mL), brine (45 mL), filtered through paper and evaporated. The residue was co-evaporated with chloroform/toluene, re-dissolved in CHCl$_3$ (10 mL) and AcOH (1 mL), diluted with toluene (5 mL) and evaporated. The crude product was re-dissolved in chloroform (25 mL), filtered and concentrated in vacuum. The residue was treated with ether (20 mL) upon sonication, centrifuged and supernatant was removed. The pellet was dried in vacuum to give ester 139 (5 mg, 86%) as a purple solid).

N-[4-((2-Dimethylamino)-5-methoxyphenyl-4-tetramethylrhodaminyl)(ethyl)amino) butanoyl]diaminopentane (141)

A mixture of N-hydroxysuccinimide ester 129 (18 mg, 0.026 mmol), DIEA (25 µL, 0.13 mmol) and BOC-diaminopentane (20 µL, 0.040 mmol) in DMF (0.5 mL) was stirred for 1 h, diluted with CHCl$_3$ (50 mL), washed with H$_2$O (2×20 mL), brine (50 mL), filtered through paper filter and evaporated to give compound 140. This crude material was stirred in CHCl$_3$ (5 mL), and TFA (2 mL) for 1 h. Upon evaporation of the volatiles the product was purified by preparative reverse-phase TLC using (H$_2$O/2-PrOH (1:1)+ 0.2% TFA) mixture as eluant to give compound 141 (7 mg, 40%) as a dark purple-red solid.

Example 111

Synthesis of pH sensors 151 and 152 having methoxy pKa-enhancing group and FURA fluorophore moiety (Scheme 111).

N-(5-Benzyloxy-2-methoxyphenyl)acetamide (145)

Aniline 144 (0.835 g, 3.65 mmol) and DIEA (0.95 mL, 5.4 mmol) were stirred with acetic anhydride (0.52 mL, 5.5 mmol) for 1 h in CHCl₃ (10 mL). The reaction mixture was Scheme 111

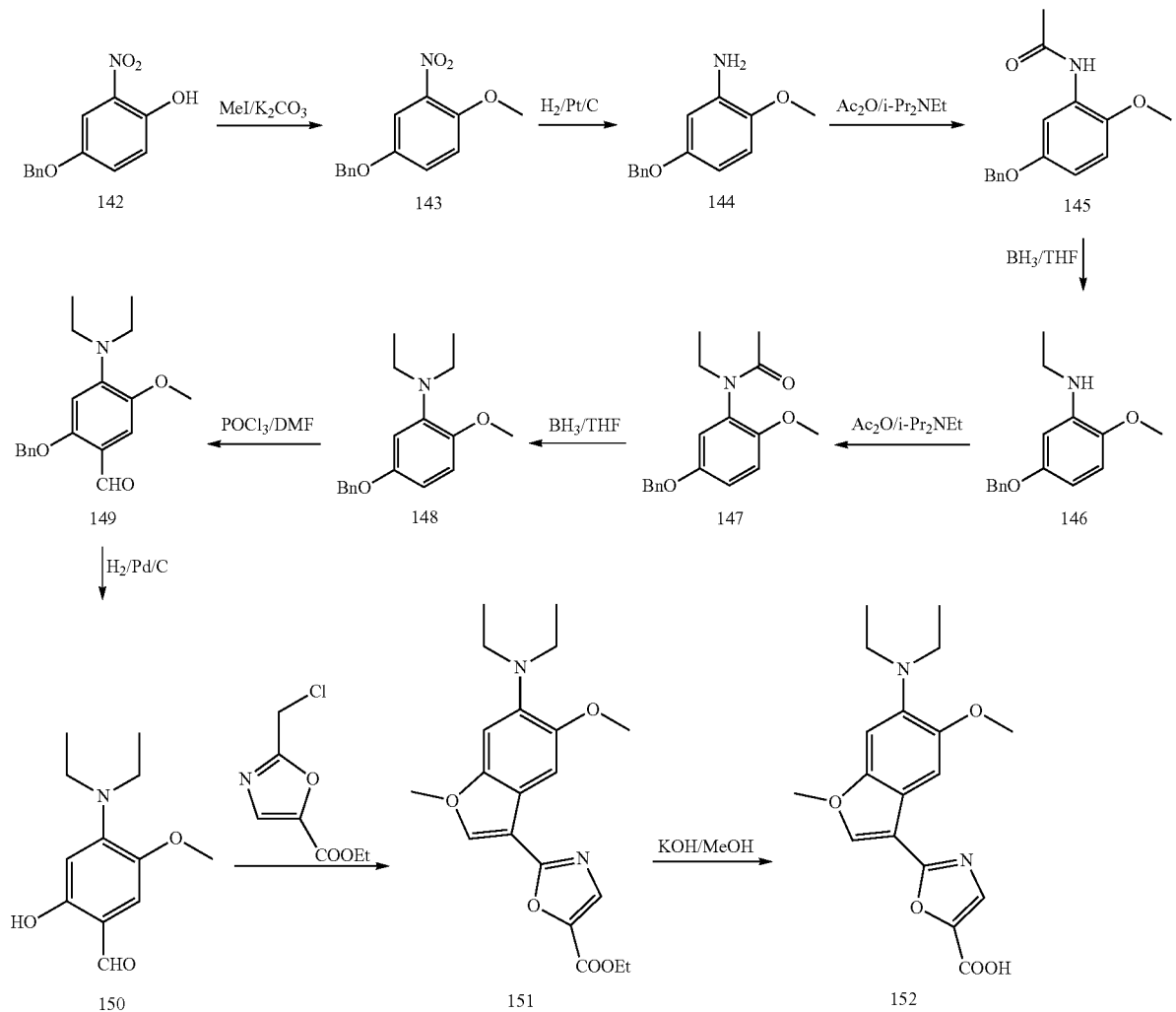

4-Benzyloxy-2-nitroanisole (143)

4-Benzyloxy-2-nitrophenol (142) (2.0 g, 8.2 mmol), powdered K₂CO₃ (1.69 g, 12.2 mmol) and MeI (0.83 mL, 16 mmol) were stirred in DMF (10 mL) for 1.5 hrs at 80° C. The reaction mixture was cooled to rt, diluted with water (100 mL) and extracted with EtOAc (3×50 mL). The combined extract was washed with water (50 mL), 1% HCl (8×50 mL), brine (30 mL), dried over Na₂SO₄ and evaporated to give methyl ether 143 (2.1 g, 99%) as a brown oil.

5-Benzyloxy-2-methoxyaniline (144)

4-Benzyloxy-2-nitroanisole (143) (2.1 g, 8.1 mmol) was hydrogenated for 2 h in Parr apparatus in CH₂Cl₂ (30 mL) over 10% Pd/C catalyst (0.10 g) at 40-45 psi hydrogen pressure. The catalyst was filtered off, and the filtrate was evaporated to give compound 144 (1.85 g, 100%) as a brown oil.

diluted with CHCl₃ (80 mL) and washed with 5% HCl (30 mL), brine (30 mL), dried over Na₂SO₄ and evaporated to give acetamide 145 (0.958 g, 99%) as a brown solid.

5-Benzyloxy-2-methoxy-N-ethylaniline (146)

To a stirred solution of N-(2-dimethylamino-5-methoxyphenyl)acetamide (145) (0.958 g, 3.55 mmol) in THF (10 mL), the BH₃-THF complex (1N, 32 mL, 32 mmol) was added, and the reaction was refluxed under stirring for 16 h. Upon cooling to rt it was carefully decomposed by slow addition of methanol (20 mL), and heated again to a gentle reflux (70° C.). The mixture was refluxed for 1 h to destroy the amine-borane complexes, cooled to rt, evaporated and co-evaporated with methanol (3×50 mL) to give the compound 146 (0.91 g, 100%) as a brown oil.

N-(5-Benzyloxy-2-methoxyphenyl)-N-ethylacetamide (147)

Amine 146 (1.0 g, 3.8 mmol) and DIEA (0.95 mL, 5.45 mmol) were stirred with acetic anhydride (0.52 mL, 5.5 mmol) for 1 h in CHCl₃ (10 mL). The reaction mixture was diluted with CHCl₃ (100 mL), washed with 5% HCl (3×30 mL), brine (30 mL), dried over Na$_2$SO$_4$ and evaporated to give acetamide 147 (1.0 g, 88%) as a brown oil.

5-Benzyloxy-2-methoxy-N,N-diethylaniline (148)

To a stirred solution of N-(5-Benzyloxy-2-methoxyphenyl)-N-ethylacetamide (147) (1.0 g, 3.34 mmol) in THF (10 mL), the BH$_3$-THF complex (1N, 32 mL, 32 mmol) was added, and the reaction was refluxed under stirring for 16 h. Upon cooling to rt it was carefully decomposed by slow addition of methanol (20 mL), and heated again to a gentle reflux (70° C.). The mixture was refluxed for 1 h to destroy the amine-borane complexes, cooled to rt, evaporated and co-evaporated with methanol (3×50 mL). The crude product was purified on a silica gel column (3×40 cm bed, packed with EtOAc/hexanes (1:5)), eluant: EtOAc/hexanes (1:5) to give compound 148 (0.317 g, 33%) as a colorless oil.

5-Benzyloxy-4-formyl-2-methoxy-N,N-diethylaniline (148)

Compound 148 (0.317 g, 1.23 mmol) was added to the solution of Vilsmeier reagent prepared from POCl$_3$ (0.56 mL, 6.12 mmol) and DMF (5 mL) and the reaction was stirred overnight at 45° C. The was cooled to rt, diluted with sat. NaHCO$_3$ (100 mL) and extracted with EtOAc (3×40 mL). The combined extract was washed with water ((3×30 mL), brine (30 mL), dried over Na$_2$SO$_4$ and evaporated to give aldehyde 149 (0.304 g, 79%) as a yellow oil.

4-Formyl-5-hydroxy-2-methoxy-N,N-diethylaniline (148)

Aldehyde 149 (0.30 g, 0.96 mmol) was hydrogenated in Parr apparatus over 10% Pd/C (0.05 g) in CH$_2$Cl$_2$ (20 mL) and AcOH (10 mL) for 16 h at 50 psi hydrogen pressure. The catalyst was filtered off and filtrate was evaporated. The residue was purified by chromatography on silica gel column (2×20 cm bed, packed with EtOAc/hexanes (1:5)), eluant: EtOAc/hexanes (1:5) to give compound 150 (0.106 g, 49%) as a colorless viscous oil.

Ethyl Ester 151.

Phenol 150 (0.123 g, 0.551 mmol), ethyl 2-(chloromethyl)oxazole-5-carboxylate (0.125 g, 0.661 mmol) and K$_2$CO$_3$ (0.152 g, 1.10 mmol) were stirred for 2.5 h in DMF (10 mL) at 120° C. The mixture was cooled down to rt, diluted with of brine (80 mL) and extracted with EtOAc (6×50 mL). The combined extract was washed with water (6×50 mL), brine (80 mL), dried over Na$_2$SO$_4$ and evaporated to give ester 151 (0.150 g, 76%) as a brown solid.

Acid 152.

Ester 151 (0.05 g, 0.14 mmol) was stirred for 16 h in MeOH (8 mL) with 1M KOH (0.7 mL, 0.7 mmol). The reaction mixture was evaporated, and the residue was dissolved in water (50 mL) and extracted with EtOAc (2×30 mL; discarded). The aqueous solution was acidified with acetic acid (3 mL) and extracted with EtOAc (10×30 mL). The combined extract was washed with brine (50 mL), dried over Na$_2$SO$_4$ and evaporated to give acid 152 (0.01 g, 22%) as a yellow foam.

Example 112

Synthesis of pH sensor 155 having two methoxy pKa-enhancing groups and X-rhodamine fluorophore (Scheme 112).

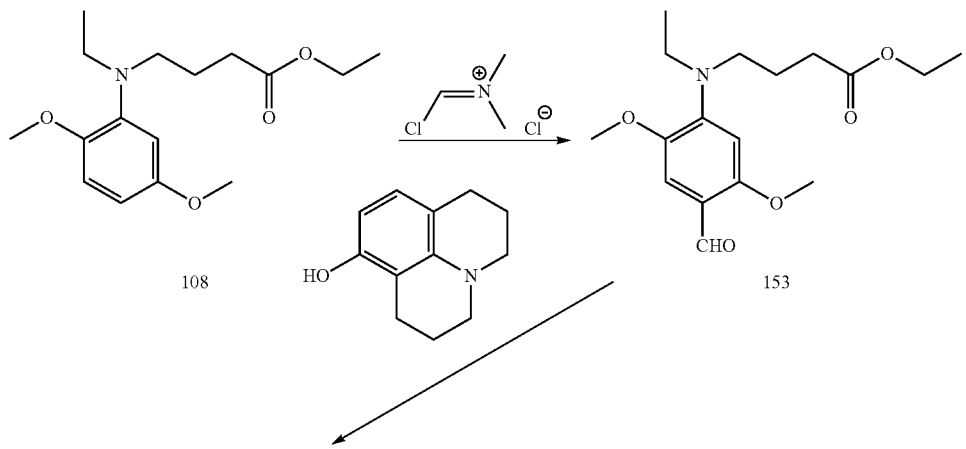

Scheme 112

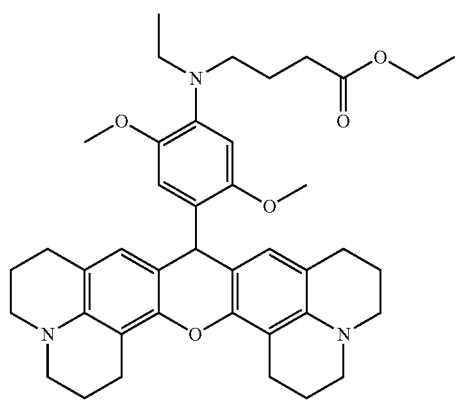
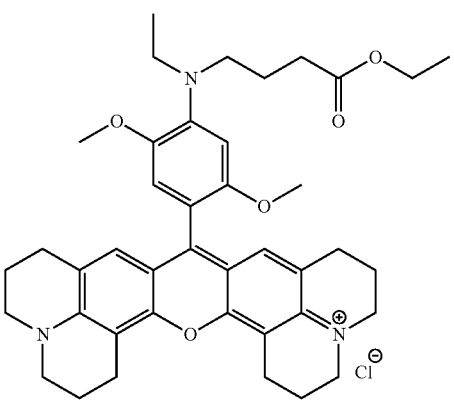

154 → (O₂, hv, Rose Bengal) → 155

Ethyl 4-(((2,5-dimethoxy)-4-formylphenyl)(ethyl)amino)butanoate (153)

Ethyl 4-((2,5-dimethoxyphenyl)(ethyl)amino)butanoate (108) (0.72 g, 2.44 mmol) and (chloromethylene)dimethyl-imminium chloride (2.50 g, 19.5 mmol) in DMF (20 mL) were stirred at 45° C. for 18 h, then cooled to rt and poured into 1:1 mixture sat. K₂CO₃— ice (300 mL). The mixture was extracted with CHCl₃ (5×50 mL), extract was washed with brine, filtered through paper filter and evaporated. The residue was purified by chromatography on a silica gel column (3×50 cm bed, packed with EtOAc/hexanes (1:3)), eluant: EtOAc/hexanes (1:3) to get compound 132 (0.680 g, 86%) as a orange oil, solidified upon standing.

X-Rhodamine pH-Sensor 155.

Aldehyde 153 (65 mg, 0.2 mmol), 8-hydroxyjullolidine (83 mg, 0.44 mmol), and 10-Camphorsulfonic acid (5 mg, catalyst) were stirred for 18 h at 65-70° C. in propionic acid (2 mL), cooled to rt and poured into aqueous 3N NaOAc (100 mL) and sat. NaHCO₃ (20 mL). The mixture was extracted with CHCl₃ (5×25 mL), extract was washed with brine (100 mL), filtered through paper filter, and evaporated to give a crude dihydro derivative 154. It was dissolved in CHCl₃ (50 mL), Bengal Rose (50 mg, catalyst) was added and the mixture was vigorously stirred in an open beaker under the sunlamp illumination for 18 h. Upon evaporation the residue was purified by preparative TLC on two silica gel plates using MeCN/H₂O (9:1) as eluant to give compound 155 (20 mg, 14%) as a dark red solid.

Example 113

Synthesis of pH sensor 157 having two methoxy pKa-enhancing groups and INDO fluorophore (Scheme 113).

Scheme 113

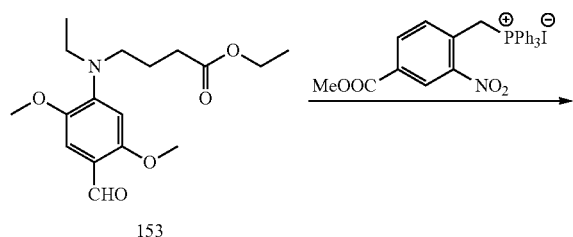

153 + [4-methoxycarbonyl-2-nitrobenzyl triphenylphosphonium iodide] →

156 —P(OEt)₃→ 157

Stilbene Derivative 156.

Aldehyde 153 (0.235 g, 0.73 mmol), 4-methoxycarbonyl-2-nitro methylenetriphenylphosphonium bromide (0.587 g, 1.09 mmol), and K₂CO₃ (0.252 g, 1.83 mmol) in DMF (5 mL) were stirred at 95-100° C. for 20 h, cooled to rt and poured into 200 mL H₂O. An aqueous 1N HCl was added to pH 3.0, and the mixture was extracted with CHCl₃ (7×25 mL). Extract was washed with brine, filtered through paper filter, and evaporated. The residue was purified by chromatography on a silica gel column (2×40 cm bed, packed with CHCl$_3$), eluant: CHCl$_3$ to get compound 156 (0.290 g, 79%) as a yellow oil, solidified upon standing.

INDO pH-Sensor 157.

Stilbene 156 (0.280 g, 0.56 mmol) was heated with P(OEt)$_3$ at 130° C. for 4 h, cooled to rt, and evaporated at 3 mm Hg vacuum. The residue was purified by chromatography on a silica gel column (2×40 cm bed, packed with EtOAc/hexanes (1:2)), eluant: EtOAc/hexanes (1:2) to get compound 157 (0.160 g, 61%) as a greenish-yellow oil.

Example 114

Synthesis of pH sensor 158 having two methoxy pKa-enhancing groups and BODIPY-Fl fluorophore (Scheme 114).

successively with 1% Me$_4$NOH (2×50 m), water (50 m), brine (50 mL), filtered through paper filter, evaporated and co-evaporated with toluene (2×30 mL). The residue was dissolved in toluene (25 mL) and stirred with chloranil (0.295 g, 1.2 mmol) for 2 h, then DIEA (1.74 mmol, 10 mmol) was added, followed by Et$_2$OBF$_3$ (1.0 mL, 8 mmol). The mixture was stirred for 4 h, evaporated, and the residue was purified on a silica gel column (4×50 cm bed, packed with 3% MeOH and 1% AcOH in CHCl$_3$), eluant: 3% MeOH and 1% AcOH in CHCl$_3$. The fractions containing the compound were evaporated, and co-evaporated with toluene (3×20 m). The residue was dissolved in CHCl$_3$ (200 m), allowed to stand for 2 h, filtered from precipitating silicates and evaporated to get compound 158 (0.210 g, 39%) as an orange oil.

Scheme 114

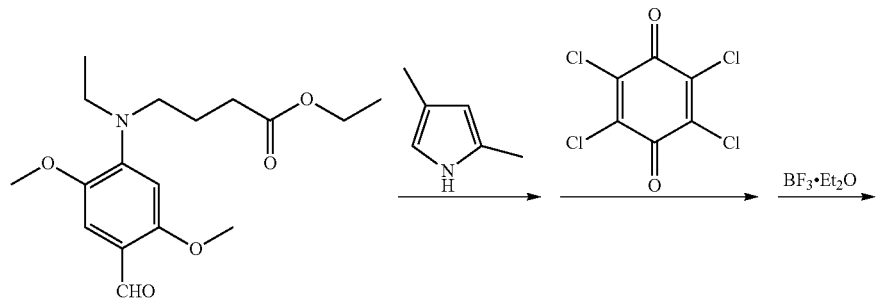

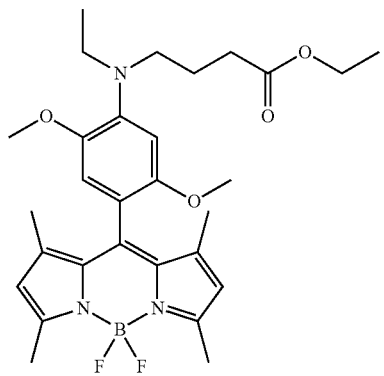

BODIPY pH-Sensor 158.

To a solution of aldehyde 153 (0.323 g, 1 mmol) in CH$_2$C$_2$ (50 mL) 2,4-dimethylpyrrole (0.25 mL, 2.4 mmol) was added, followed by TFA (0.09 mL, 1.2 mmol). The reaction was stirred for 16 h, diluted with CHCl$_3$ (200 mL), washed Example 115

Synthesis of pH sensor 133 having methoxy and dimethylamino pKa—enhancing groups and tetramethylrhodamine fluorophore (Scheme 115).

Scheme 115

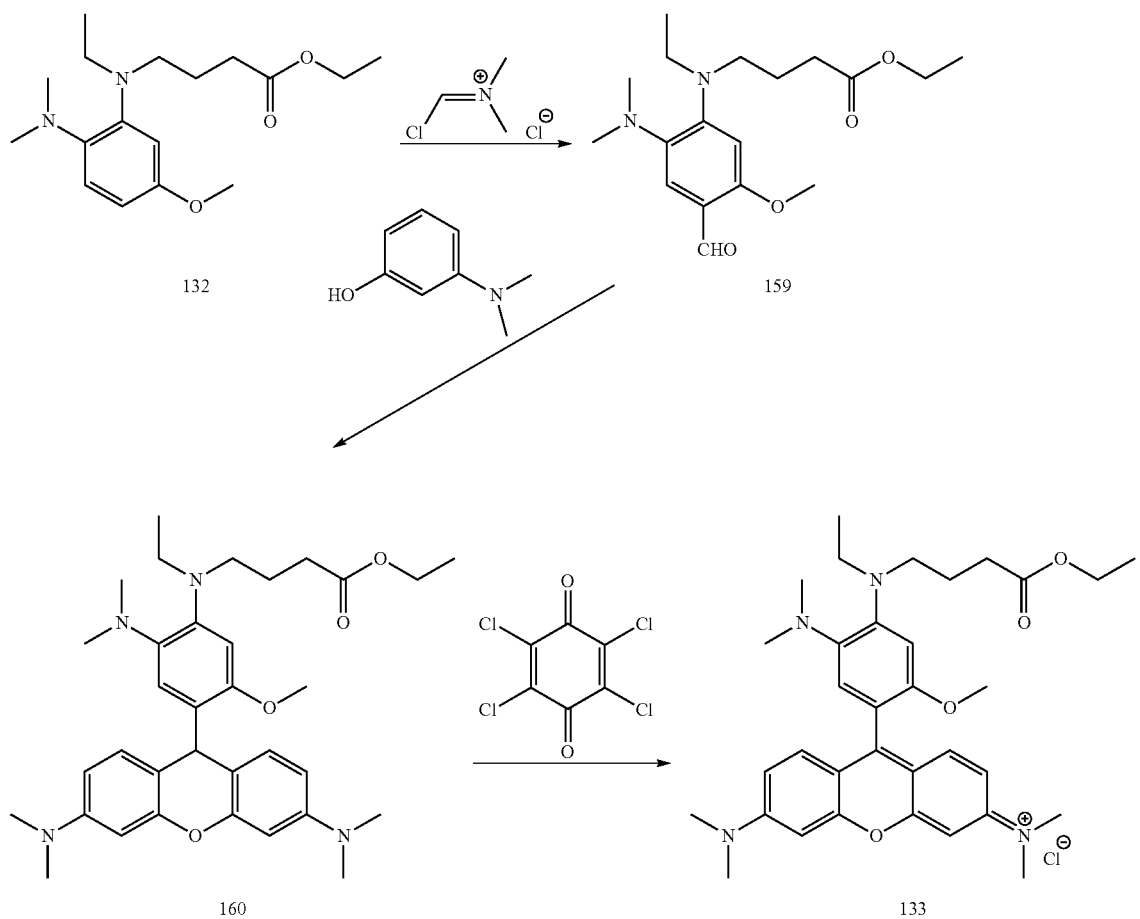

Ethyl 4-(((2-dimethylamino)-4-formyl-5-methoxyphenyl)(ethyl)amino)butanoate (159)

Ethyl 4-((2-dimethylamino)-5-methoxyphenyl)(ethyl)amino)butanoate (132) (1.74 g, 5.65 mmol) and (chloromethylene)dimethylimminium chloride (5.78 g, 45.19 mmol) in DMF (50 mL) were stirred at 45° C. for 72 h, then cooled to rt and poured into 1:1 mixture sat. $K_2CO_3$/ice (400 mL). The mixture was extracted with $CHCl_3$ (6×80 mL), extract was washed with brine, filtered through paper and evaporated. The residue was purified by chromatography on a silica gel column (3×50 cm bed, packed with EtOAc/hexanes (3:7)), eluant: EtOAc/hexanes (3:7) to get compound 159 (1.210 g, 67%) as a orange oil, which solidified upon standing.

Ethyl 4-((2-dimethylamino)-5-methoxyphenyl-4-tetramethylrhodaminyl)(ethyl)amino) Butanoate (133)

Aldehyde 159 (0.500 g, 1.55 mmol), 2-dimethylamino phenol (0.510 g, 3.72 mmol), and 10-Camphorsulfonic acid (30 mg, catalyst) were stirred in propionic acid (15 mL) for 18 h at 65-70° C., cooled to rt and poured into aqueous 3N NaOAc (400 mL) and sat. $NaHCO_3$ (30 mL). The mixture was extracted with $CHCl_3$ (6×50 mL), extract was washed with brine (200 mL), filtered through paper filter, and evaporated to give a crude dihydro derivative 160. A portion of this product (30 mg, 0.054 mmol) was stirred for 2.5 h with chloranil (16 mg, 0.065 mmol) in 2 mL $CHCl_3$ and 2 mL MeOH. The solvent was evaporated, and the mixture was purified with preparative TLC on silica gel plate, using MeCN/AcOH/$H_2O$ (16:4:3) as eluant to give compound 132 (4 mg, 13%) as a dark purple oil.

Example 116

Synthesis of pH sensor 162 having methoxy- and dimethylamino pKa-enhancing groups and X-rhodamine fluorophore (Scheme 116).

Scheme 116

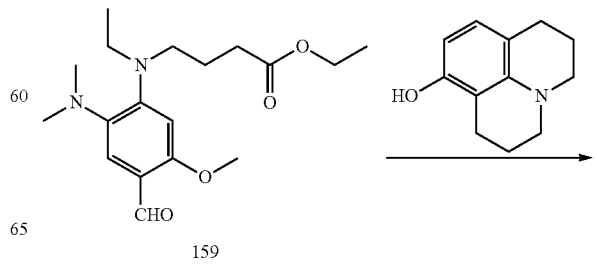

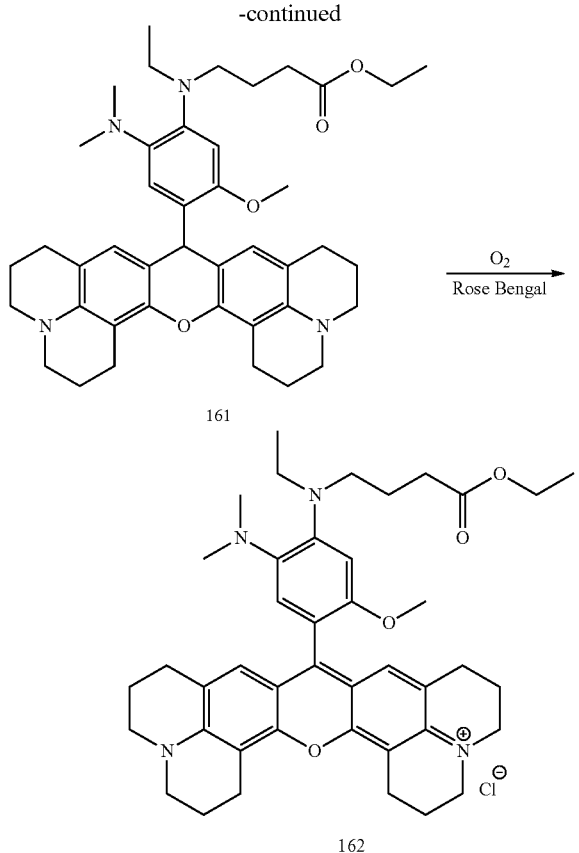

X-Rhodamine pH-Sensor 162.

Aldehyde 159 (0.336 g, 1.0 mmol), 8-hydroxyjullolidine (0.416 g, 2.2 mmol), and 10-camphorsulfonic acid (20 mg, catalyst) were stirred for 18 h in propionic acid (10 mL) at 65-70° C., cooled to rt and poured into aqueous 3N NaOAc (200 mL) and sat. $NaHCO_3$ (10 mL). The mixture was extracted with $CHCl_3$ (7×40 mL), extract was washed with brine (200 mL), filtered through paper filter, and evaporated to give a crude dihydro derivative 161. A sample of this compound (40 mg, 0.06 mmol) was vigorously stirred in $CHCl_3$ (50 mL) with Bengal Rose (10 mg, catalyst) in an open beaker under the sunlamp illumination for 18 h. After evaporation the residue was purified by preparative TLC on two silica gel plates using 7% $H_2O$ in MeCN as eluant to give compound 162 (11 mg, 24%) as a dark red solid.

Example 117

Synthesis of pH sensor 163 having methoxy- and dimethylamino pKa enhancing groups and BODIPY-Fl fluorophore (Scheme 117).

Scheme 117

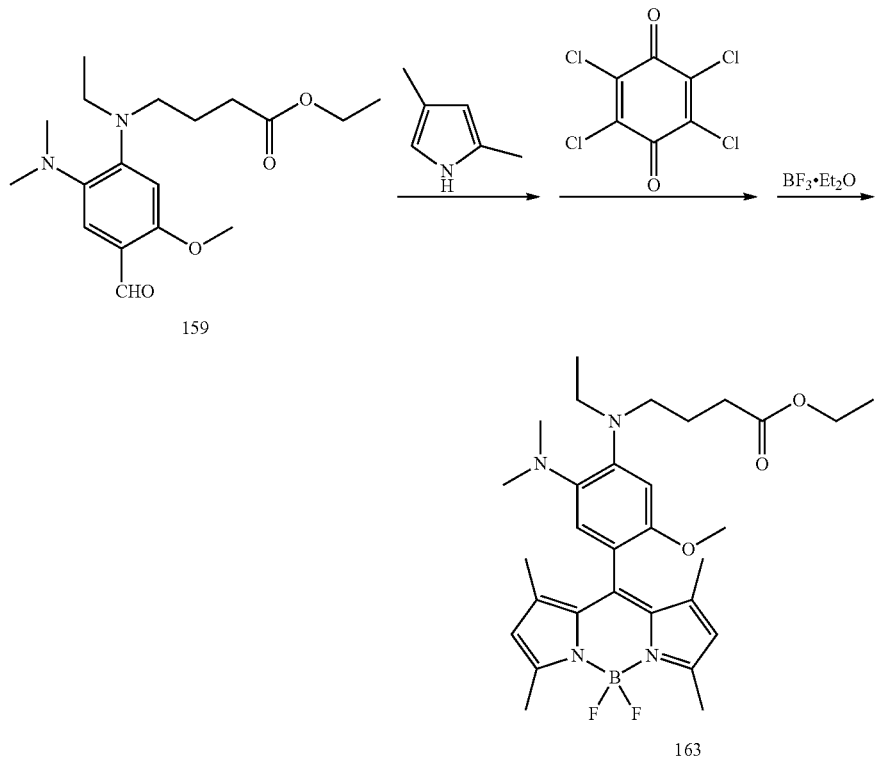

BODIPY pH-Sensor 163.

To a solution of aldehyde 159 (0.336 g, 1 mmol) in CH$_2$Cl$_2$ (50 mL) 2,4-dimethylpyrrole (0.25 mL, 2.4 mmol) was added, followed by TFA (0.09 mL, 1.2 mmol). The reaction was stirred for 16 h, diluted with CHCl$_3$ (200 mL) and washed successively with 1% Me$_4$NOH (2×50 mL), water (50 mL), brine (50 mL), filtered through paper filter, evaporated and co-evaporated with toluene (2×30 mL). The residue was dissolved in toluene (25 mL), stirred with chloranil (0.295 g, 1.2 mmol) for 2 h, then DIEA (1.74 mmol, 10 mmol) was added, followed by Et$_2$OBF$_3$ (1.0 mL, 8 mmol). The mixture was stirred for 4 h, evaporated, and the residue was purified on a silica gel column (3×45 cm bed, packed with 5% MeOH and 1% AcOH in CHCl$_3$), eluant: 5% MeOH and 1% AcOH in CHCl$_3$. The fractions containing the compound were evaporated, and chromatographed again on the second silica gel column (4×50 cm bed, packed in EtOAc/hexanes (1:1), eluant: EtOAc/hexanes (1:1) to get compound 163 (0.180 g, 32%) as an orange oil.

Example 118

Synthesis of pH sensor 166 having methoxy- and dimethylamino pKa enhancing groups and BODIPY-FI fluorophore, and compound 168 with a labeling succinimidyl ester moiety (Scheme 118).

4-((2-Dimethylamino)-4-formyl-5-methoxyphenyl)(ethyl)amino) Butanoic Acid (164)

A mixture of compound 159 (2.40 g, 7.1 mmol) and 1N KOH (71 ml, 71 mmol) in MeOH (70 mL) was stirred for 5 h, evaporated, and re-dissolved in water (100 mL). An aqueous 1N HCl was added to pH 5, and the mixture was extracted with CHCl$_3$ (10×40 mL). Extract was washed with brine (200 mL), dried over MgSO$_4$ and evaporated to give the acid 164 (2.20 g, 97%) as an orange solid.

Diphenylmethyl 4-((2-Dimethylamino)-4-formyl-5-methoxyphenyl)(ethyl)amino) Butanoate (165)

To a stirred solution of the acid 164 (0.308 g, 1 mmol) in acetone (5 mL) was added an acetone solution (5 mL) of diphenyldiazomethane, made from benzophenone hydrazone (0.392 g, 2 mmol). The mixture was stirred for 16 h at 40° C., then 0.5 mL of acetic acid was added and the stirring was continued for 2 h to decompose the excess of diphenyldiazomethane. The mixture was evaporated and the crude product was purified by chromatography on a silica gel column (3×50 cm bed, packed with CHCl$_3$), eluant: CHCl$_3$ to get compound 165 (0.382 g, 81%) as a orange oil, which solidified upon standing.

Diphenylmethyl Ester 166.

To a solution of aldehyde 165 (0.230 g, 0.485 mmol) in CH$_2$Cl$_2$ (20 mL) 2,4-dimethylpyrrole (0.12 mL, 1.16 mmol)

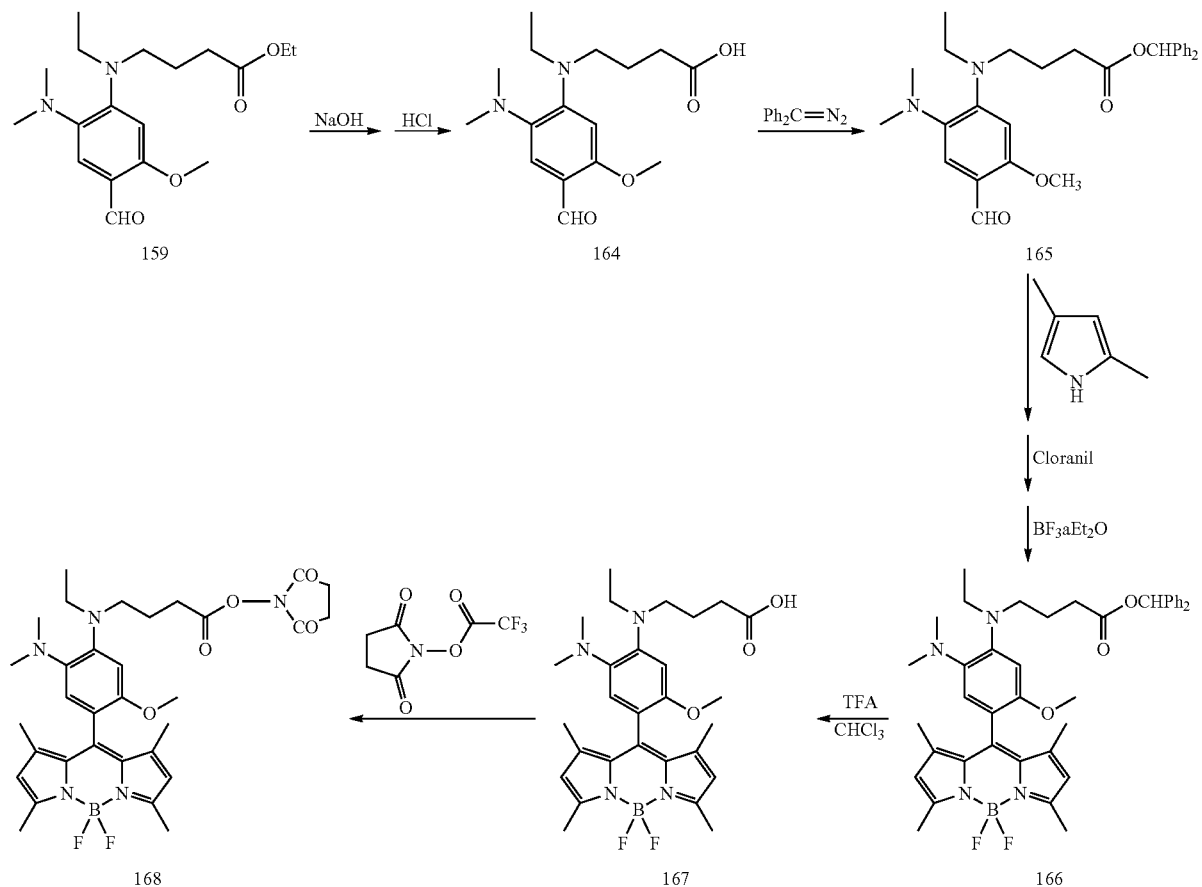

was added, followed by TFA (0.05 mL, 0.580 mmol). The reaction was stirred for 16 h, diluted with $CHCl_3$ (100 mL) and washed successively with 1% $Me_4NOH$ (2×30 mL), water (100 mL), brine (100 mL), filtered through paper filter, evaporated and co-evaporated with toluene (2×30 mL). The residue was dissolved in toluene (15 mL) and stirred with chloranil (0.143 g, 0.582 mmol) for 2 h, then DIEA (0.84 mmol, 4.85 mmol) was added, followed by $Et_2OBF_3$ (0.55 mL, 3.88 mmol). The mixture was stirred for 4 h, evaporated, and the residue was purified on a silica gel column (4×50 cm bed, packed with $CHCl_3$), eluant: $CHCl_3$ to get the compound 166 (0.240 g, 71%) as a dark-red oil.

BODIPY—Acid 167.

To a solution of the compound 166 (0.200 g, 0.29 mmol) in $CHCl_3$ (10 mL) was added TFA (5 mL). The mixture was stirred for 3 min, diluted with $CHCl_3$ and washed with 3N NaOAc (200 ml) and brine (200 mL). The chloroform solution was evaporated and the residue was purified by preparative TLC on four silica gel plates using 7.5% $H_2O$ in MeCN as eluant to give compound 167 (0.025 g, 16%) as a dark red solid.

N-Hydroxysuccinimidyl Ester 168.

To a solution of the acid 167 (22 mg, 0.04 mmol) in DMF (0.5 mL) and DIEA (70 μL, 0.4 mmol) was added dry N-hydroxysuccinimidyl trifluoroacetate (84 mg, 0.4 mmol). The mixture was stirred for 16 h, evaporated and the residue was purified by flash chromatography on a silica gel column (0.5×25 cm bed, packed with $CHCl_3$), eluant: $CHCl_3$ to get the compound 168 (20 mg, 80%) as a dark orange semi-solid.

Example 119

Synthesis of pH sensor 171 having methoxy- and dimethylamino pKa-enhancing groups, labeling succinimidyl ester moiety and BODIPY fluorophore (Scheme 119).

Scheme 119

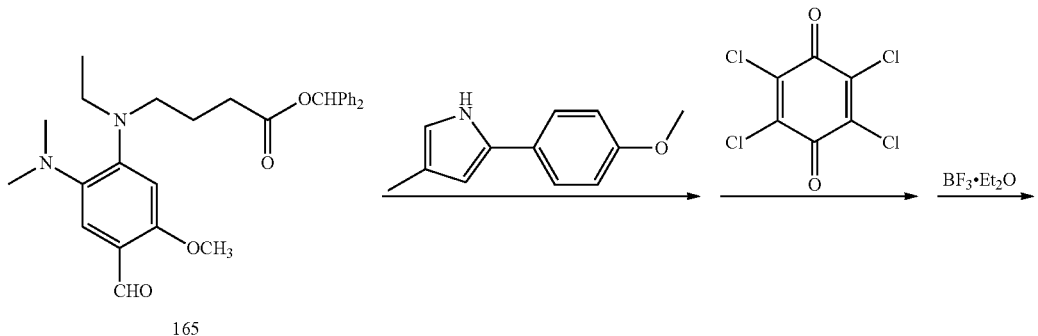

165

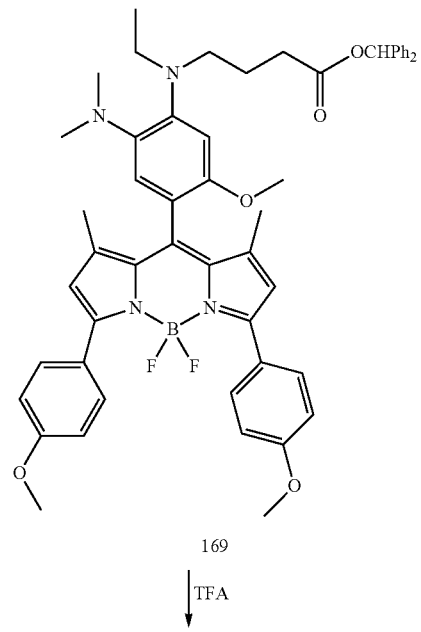

169

TFA

-continued

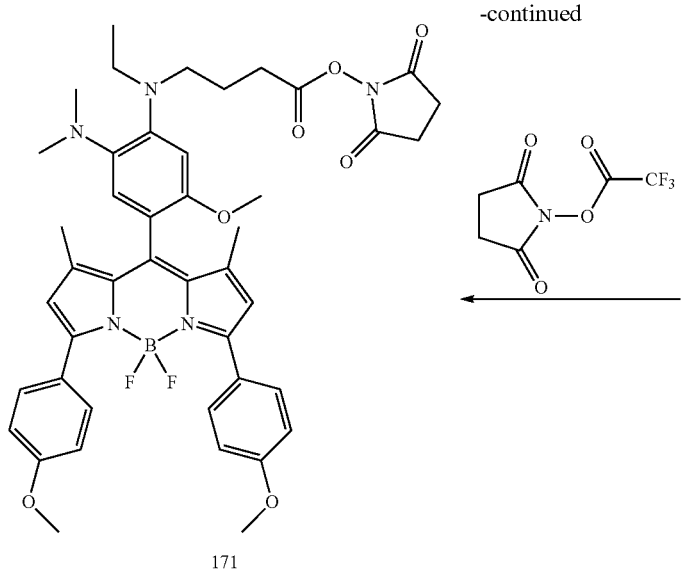

171

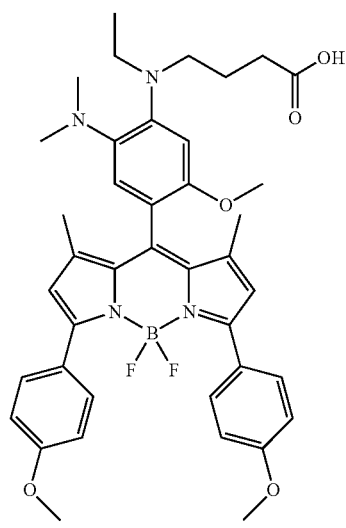

170

Diphenylmethyl Ester 169.

To a solution of aldehyde 165 (0.142 g, 0.3 mmol) in CH$_2$Cl$_2$ (15 mL) 2-(4-methoxyphenyl)pyrrole (0.125 g, 0.72 mmol) was added, followed by TFA (0.03 mL, 0.36 mmol). The reaction was stirred for 16 h, diluted with CHCl$_3$ (100 mL) and washed successively with 1% Me$_4$NOH (2×30 mL), water (100 mL), brine (100 mL), filtered through paper filter, evaporated and co-evaporated with toluene (2×30 mL). The residue was dissolved in toluene (10 mL) and stirred with chloranil (0.089 g, 0.36 mmol) for 2 h, then DIEA (0.52 mmol, 3.0 mmol) was added, followed by Et$_2$OBF$_3$ (0.30 mL, 2.4 mmol). The mixture was stirred for 4 h, evaporated, and the residue was purified on a silica gel column (4×50 cm bed, packed with CHCl$_3$), eluant: CHCl$_3$ to get the compound 169 (0.150 g, 59%) as a dark-red semi-solid.

BODIPY—Acid 170.

To a solution of the compound 169 (50 mg, 0.06 mmol) in CHCl$_3$ (10 mL) was added TFA (5 mL). The mixture was stirred for 3 min, diluted with CHCl$_3$ (100 mL) and washed with 3N NaOAc (200 ml) and brine (200 mL). The chloroform solution was evaporated and the residue was purified by preparative TLC on two silica gel plates using 7.5% H$_2$O in MeCN as eluant to give compound 170 (0.28 g, 68%) as a dark red solid.

N-Hydroxysuccinimidyl Ester 171.

To a solution of the acid 170 (23 mg, 0.034 mmol) in DMF (0.5 mL) and DIEA (60 mL, 0.34 mmol) was added a dry N-hydroxysuccinimidyl trifluoroacetate (72 mg, 0.34 mmol). The mixture was stirred for 2 h, diluted with CHCl$_3$ (50 mL), washed with 1% AcOH (50 mL), water (3×50 mL), brine (50 mL). The CHCl$_3$ solution was dried over MgSO$_4$ and evaporated to get the compound 171 (22 mg, 83%) as a dark red semi-solid.

Example 120

Synthesis of pH sensor 173 having amidine indicator group and fluorescein fluorophore (Scheme 120).

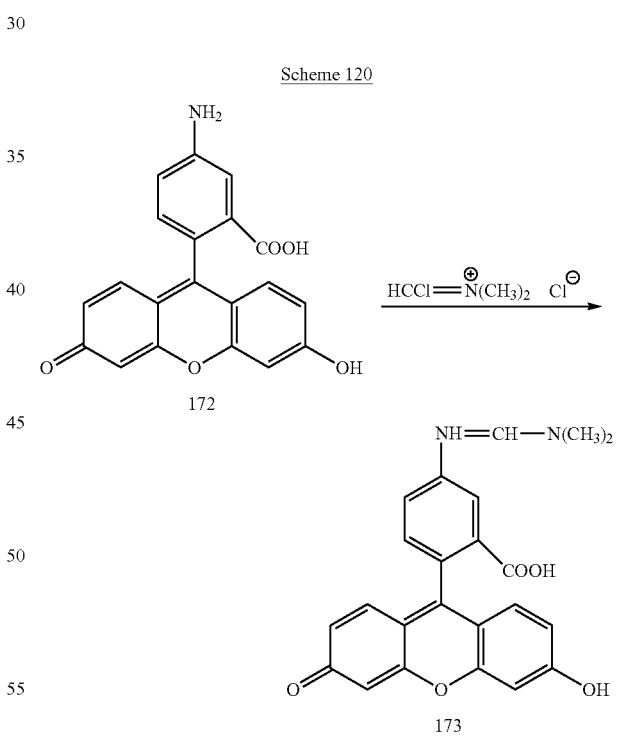

Scheme 120

Fluorescein Formamidine 173.

5-Aminofluorescein (172) (0.100 g, 0.29 mmol) and (chloromethylene)dimethylimminium chloride (0.135 g, 1.11 mmol) were stirred for 16 h in DMF (2 mL). The reaction mixture was evaporated, and the crude product was purified on a silica gel column (1.5×25 cm bed, packed with 10% H$_2$O in MeCN), eluant: 10% H$_2$O in MeCN to give amidine 173 (0.049 g, 42%) as a yellow solid.

Example 121

Synthesis of pH sensor 175 having amidine indicator group and tetramethylrhodamine fluorophore (Scheme 121).

Scheme 121

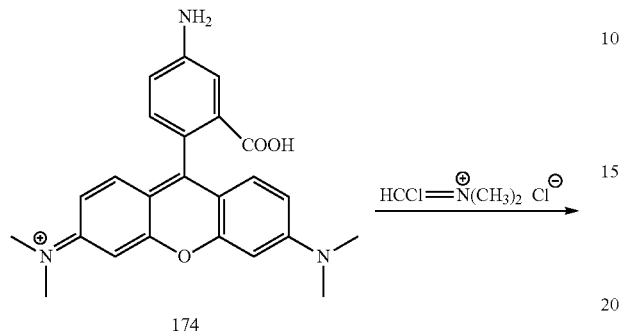

Scheme 122

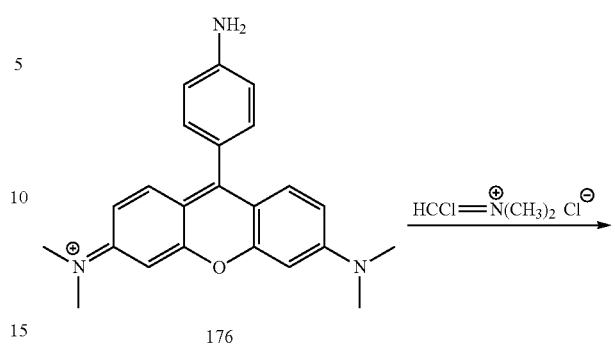

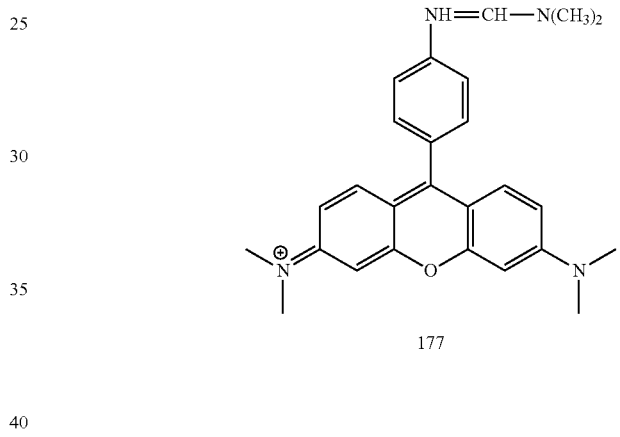

Rhodamine Formamidine 175.

5-Aminorhodamine 174 (0.100 g, 0.249 mmol), (chloromethylene)dimethylimminium chloride (0.304 g, 2.49 mmol), and DIEA (0.50 mL, 2.87 mmol) were stirred in 4 mL of DMF for 16 h. The reaction mixture was evaporated and the crude product was purified on a silica gel column (1.5×25 cm bed, patched in MeCN/H$_2$O/AcOH (8:2:2.5)), eluant: MeCN/H$_2$O/AcOH (8:2:2.5) to give amidine 175 (0.050 g, 44%) as a red solid.

Example 122

Synthesis of pH sensor 177 having amidine indicator group and tetramethylrhodamine fluorophore (Scheme 122).

Tetramethylrhodamine Formamidine 177.

5-Amino(tetramethyl)rhodamine 176 (0.100 g, 0.254 mmol), (chloromethylene)dimethylimminium chloride (0.155 g, 1.27 mmol), and DIEA (0.22 mL, 1.26 mmol) were stirred in 4 mL of DMF for 16 h. The reaction mixture was evaporated and the crude product was purified on a silica gel column (1.5×25 cm bed, patched in MeCN/H$_2$O/AcOH (8:2:2.5)), eluant: MeCN/H$_2$O/AcOH (8:2:2.5) to give amidine 177 (0.050 g, 48%) as a red solid.

Example 123

Synthesis of pH sensor 178 having sulfonic acid group, compound 179 with a labeling succinimidyl ester moiety, and C$_{16}$-derivative 180 (Scheme 123).

Scheme 123

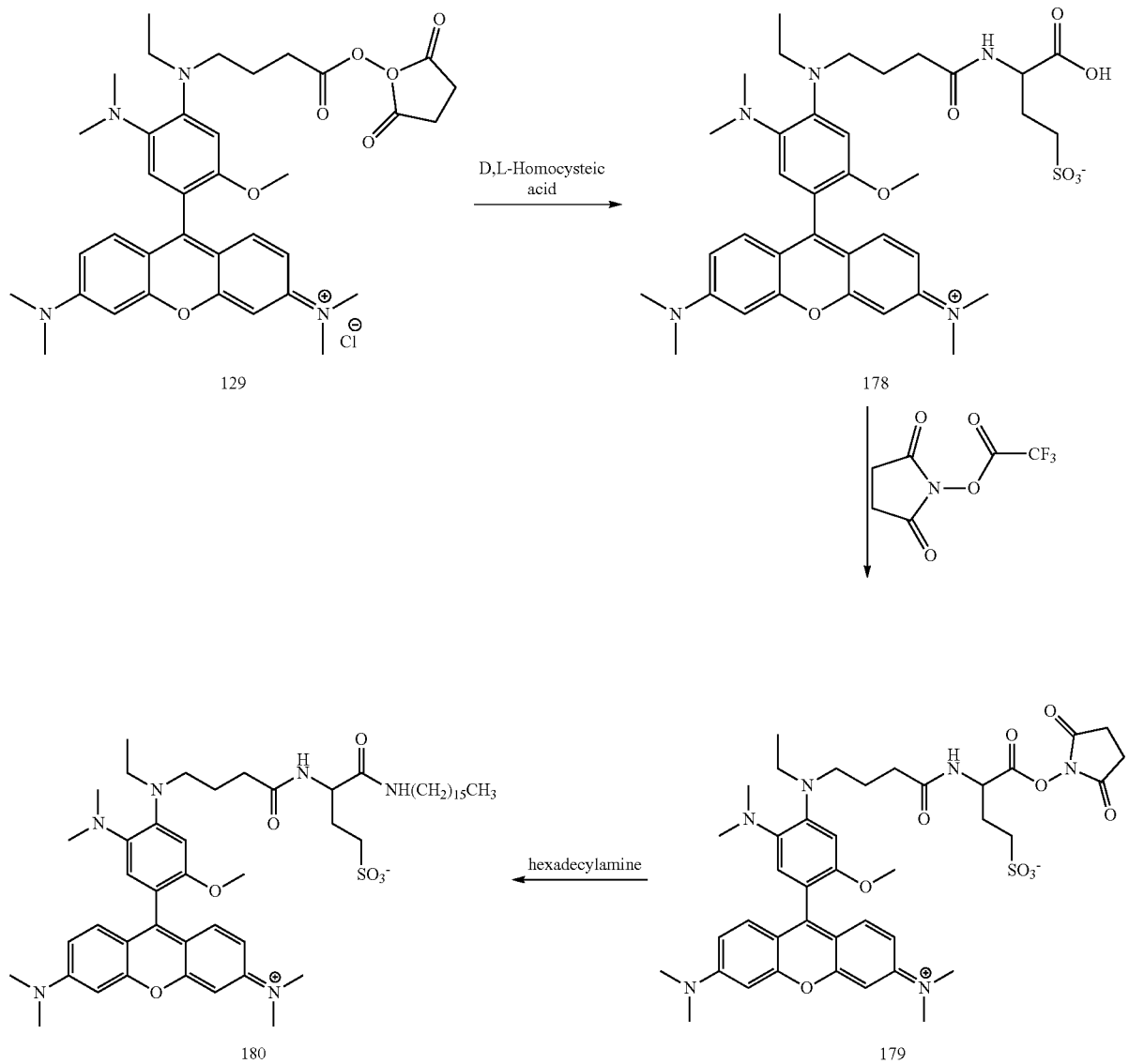

Sulfonic Acid Derivative 178.

To a stirred solution of D,L-homocysteic acid (16 mg, 0.0087 mmol) in 1 mL of water containing 37 μL (0.037 mmol) of 1M Et$_3$NH$_2$CO$_3$ buffer was added succinimidyl ester 129 (5 mg, 0.007 mmol) and the mixture was stirred for 2 h and evaporated. The residue was co-evaporated with water (3×10 mL) and the crude product was purified on reversed-phase preparative TLC plate, eluant: 50% 2-PrOH containing 0.2% TFA to give sulfonic acid derivative 178 (5 mg, 81%) as a purple powder.

Succinimidyl Ester (179).

Acid 178 (5 mg, 0.006 mmol), N,N-disuccinimidyl carbonate (2 mg, 0.0074 mmol), and DMAP (1 mg, catalyst) were stirred in MeCN (1 mL) for 40 min and evaporated. The residue was dissolved in CHCl$_3$ (1 mL) and diluted with of ether (20 mL). The mixture was centrifuged and the supernatant was removed. The pellet was suspended in ether (20 mL) and the suspension was centrifuged again. After removing supernatant the procedure was repeated and the solid was dried in vacuum to give succinimidyl ester 179 (5 mg, 84%) as a purple solid.

Hexadecyl Amide (180).

Succinimidyl ester 179 (5 mg, 0.006 mmol), DIEA (2 μL, 0.01 mmol), and hexadecylamine (2 mg, 0.0075 mmol) were stirred in MeCN (2 mL) for 25 min, and evaporated. The residue was dissolved in CHCl$_3$ (1 mL) and diluted with of ether (20 mL). The purple precipitate was filtered and dried in vacuum to give amide 180 (5 mg, 89%) as a purple solid.

Example 124

Synthesis of pH sensor 183 with tetramethylrhodamine fluorophore having extra negative charges (Scheme 124).

Scheme 124

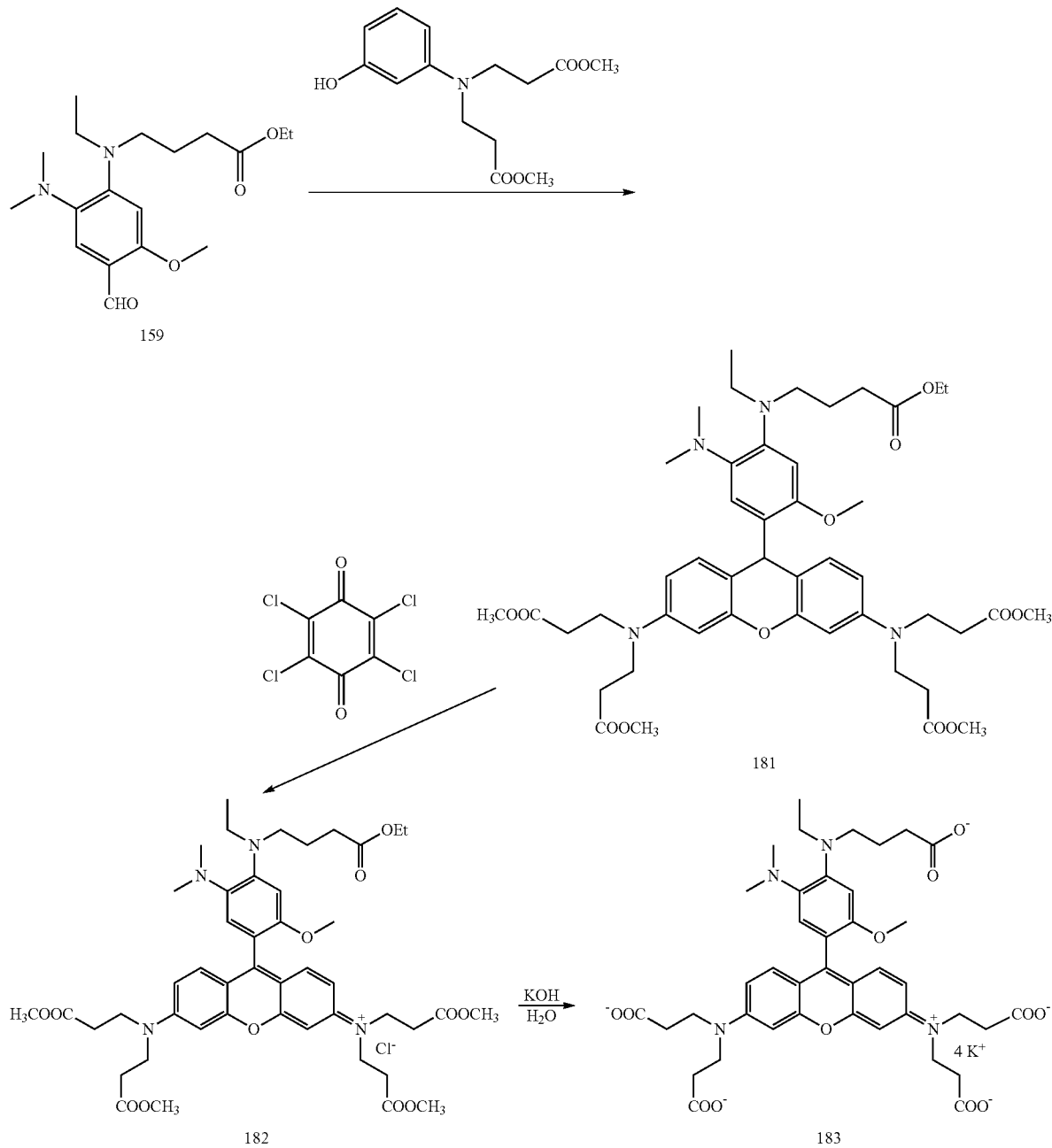

Tetramethoxycarbonyl Derivative 182.

Aldehyde 159 (0.336 g, 1.0 mmol), 3-N,N-bis(2-methoxycarbonylethyl)amino phenol (0.674 g, 2.4 mmol), and 10-camphorsulfonic acid (20 mg, catalyst) in propionic acid (20 mL) were stirred for 18 h at 65-70° C., cooled to rt and poured into aqueous 3N NaOAc (200 mL) and sat. NaHCO$_3$ (10 mL). The mixture was extracted with CHCl$_3$ (7×30 mL), extract was washed with brine (200 mL), dried over MgSO$_4$, and evaporated to give a crude dihydro derivative 181. It was dissolved in CHCl$_3$ (15 mL) and MeOH (15 ML), stirred with chloranil (0.271 g, 1.1 mmol) for 3 h, filtered from excess oxidant, and evaporated. The residue was purified on a silica gel column (4×50 cm bed, packed with 3% MeOH and 1% AcOH in CHCl$_3$), eluant: 3% to 6% gradient MeOH and 1% AcOH in CHCl$_3$. The fractions containing the compound were evaporated, and co-evaporated with toluene (3×20 mL). The residue was dissolved in CHCl$_3$ (250 mL), allowed to stand for 2 h, filtered from precipitating silicates and evaporated to get compound 182 (0.320 g, 36%) as a dark red semi-solid.

Pentacarboxylic Derivative 183.

A solution of the compound 172 (17 mg, 0.02 mmol) in MeOH (2 mL) and 1N KOH (0.3 mL, 0.3 mmol) was stirred for 16 h, then diluted with water (10 mL). Aqueous 0.2 N HCl was added to pH 9.5, and the mixture was evaporated. The residue was purified by chromatography on a Sephadex LH-20 column (2×60 cm bed, packed with H₂O), eluant: water. The fractions containing product were pulled together and lyophilized to give the compound 183 (7 mg, 38%) as dark purple flakes.
Example 125
Synthesis of pH sensor 189 having hydroxyl and methoxy enhancing group.
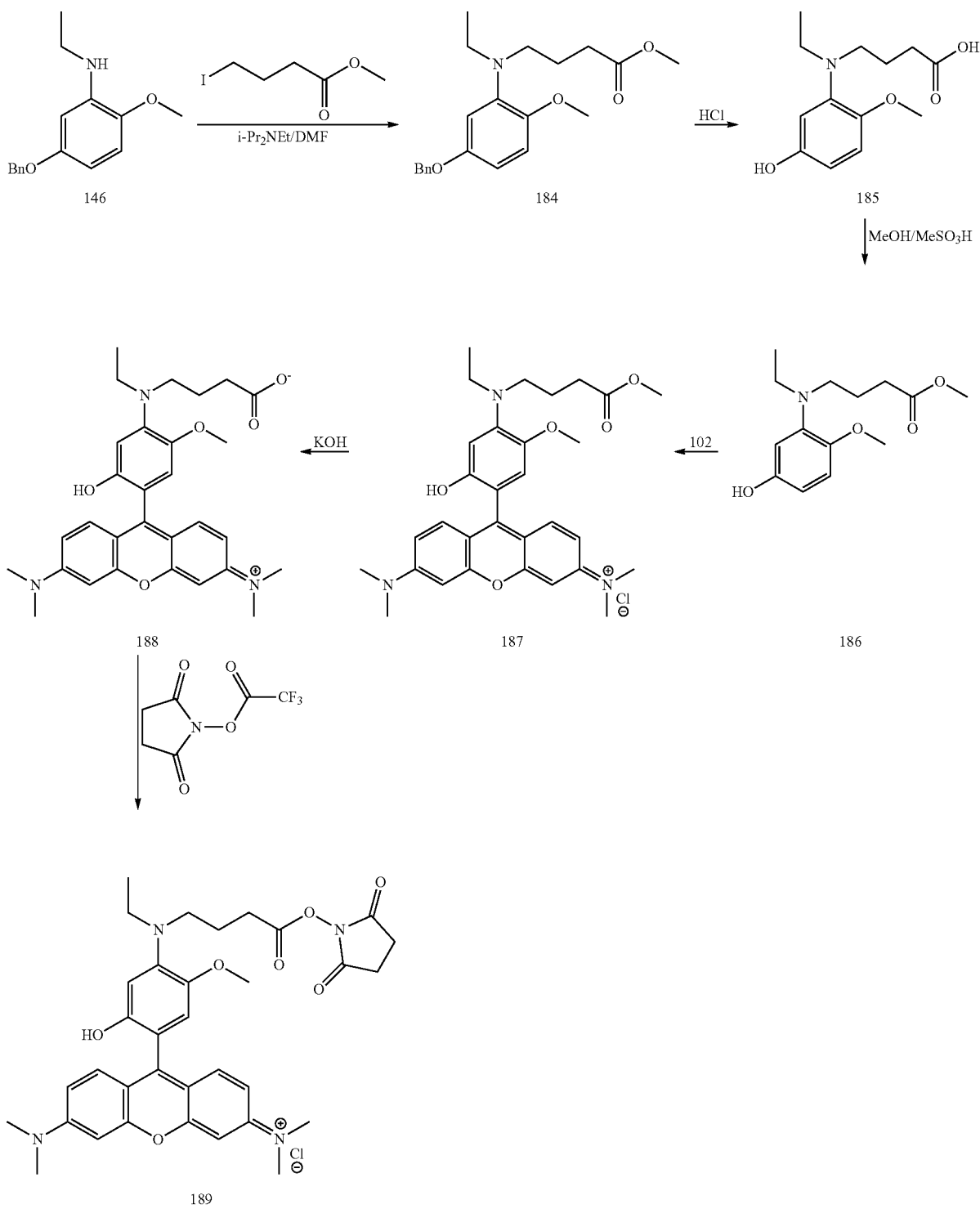

Methyl 4-((5-(benzyloxy)-2-methoxyphenyl)(ethyl) amino)butanoate (184)

5-(Benzyloxy)-N-ethyl-2-methoxyaniline (146) (0.681 g, 2.65 mmol), DIEA (0.92 mL, 5.3 mmol), and methyl 4-iodobutyrate (0.72 mL, 5.3 mmol) in DMF (5 mL) were stirred at 70° C. for 5 days. The reaction mixture was cooled to rt, diluted with EtOAc (60 mL), washed with water (4×50 mL), brine (75 mL), dried over $Na_2SO_4$ and evaporated. The residue was purified by chromatography on a silica gel column (2.5×30 cm bed, packed with $CHCl_3$), eluant: 5% MeOH in $CHCl_3$ to get compound 184 (0.72 g, 76%) as a dark amber oil.

Methyl 4-(ethyl(5-hydroxy-2-methoxyphenyl)amino)butanoate (186)

Ester 184 (0.72 g, 2.0 mmol) was stirred under reflux with 6 mL of water and 6 mL of conc HCl for 1.5 hrs and then evaporated to dryness to give acid 185 as a brown gum. The crude acid was dissolved in 50 mL of methanol containing 1 drop (cat.) of methanesulfonic acid and the solution was kept for 2 hrs at rt. After that the mixture was concentrated in vacuum and the residue was mixed with 20 mL of saturated $NaHCO_3$. The product was extracted with EtOAc (3×40 mL). The extract was washed with brine (40 mL), dried over $Na_2SO_4$ and evaporated. The residue was purified by chromatography on a silica gel column (2.5×30 cm bed, packed with $CHCl_3$), eluant: 5% MeOH in $CHCl_3$ to get compound 186 (0.444 g, 83%) as a brown oil.

N-(6-(dimethylamino)-9-(4-(ethyl(4-methoxy-4-oxobutyl)amino)-2-hydroxy-5-methoxyphenyl)-3H-xanthen-3-ylidene)-N-methylmethanaminium Chloride (187)

To a stirred suspension of tetramethylrhodamine ketone 101 (0.234 g, 0.830 mmol) in 10 mL of dry chloroform was added oxalyl chloride (72 μL, 0.82 mmol) upon cooling to 0-5° C. The resulting red solution was stirred for 0.5 h at 5° C., and the solution of compound 186 (0.222 g, 0.831 mmol) in dry chloroform (5 mL) was introduced. The reaction was allowed to heat to rt, stirred for 72 h, diluted with $CHCl_3$ (100 mL and washed with sat. $NaHCO_3$ solution (2×30 mL) The organic layer was extracted with 5% HCl (3×25 mL). The combined acid extract was washed with $CHCl_3$ (2×15 mL; discarded), saturated with sodium acetate and extracted with $CHCl_3$ (5×30 mL). The extract was washed with brine (50 mL), dried over $Na_2SO_4$ and evaporated. The crude product was purified by chromatography on silica gel column (2×50 cm bed, packed with $CHCl_3/MeOH/AcOH/H_2O$ (100:20:5:1)), eluant: $CHCl_3/MeOH/AcOH/H_2O$ (100:20:5:1) to give the product 187 (0.138 g, 29%) as a purple solid.

4-((4-(6-(dimethylamino)-3-(dimethyliminio)-3H-xanthen-9-yl)-5-hydroxy-2-methoxyphenyl)(ethyl) amino)butanoate (188)

Methyl ester 187 (0.136 g, 0.240 mmol) was dissolved in 5 mL of 1M KOH (5 mmol). The reaction mixture was kept at rt for 1.5 hrs and the acetic acid (1 mL) was added. The mixture was extracted with $CHCl_3$ (4×30 mL) and combined extract was washed with brine (20 mL), filtered through the paper filter and. The crude product was purified by chromatography on silica gel column (2×50 cm bed, packed with $MeCN/H_2O$ (4:1)), eluant: $MeCN/H_2O/AcOH/$ (4:1:1) to give the product 188 (0.069 g, 98%) as a purple solid.

N-(6-(dimethylamino)-9-(4-((4-(2,5-dioxopyrrolidin-1-yloxy)-4-oxobutyl)(ethyl)amino)-2-hydroxy-5-methoxyphenyl)-3H-xanthen-3-ylidene)-N-methyl-methanaminium Chloride (189)

To a solution of the acid 188 (69 mg, 0.12 mmol) in DMF (2 mL) and DIEA (58 μL, 0.33 mmol) was added N-hydroxysuccinimide trifluoroacetate (70 mg, 0.33 mmol). The reaction mixture was stirred for 30 min, diluted with chloroform (100 mL) and washed with water (5×50 mL), brine (50 mL), filtered through paper and concentrated in vacuum. The crude product was purified by precipitation from $CHCl_3$ solution (5 mL) with ether (20 mL) to give compound 189 (55 mg, 67%) as a purple powder.

Example 126

AM Ester Synthesis:

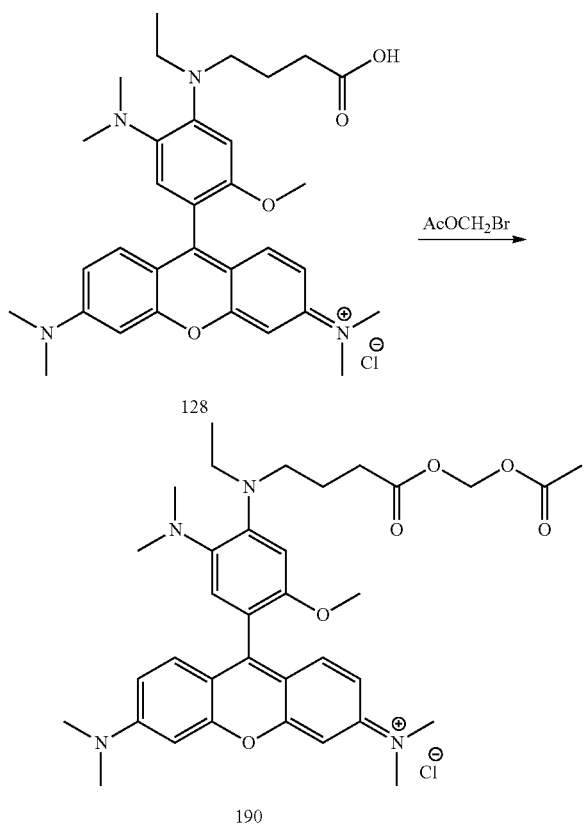

N-(9-(4-((4-(acetoxymethoxy)-4-oxobutyl)(ethyl) amino)-5-(dimethylamino)-2-methoxyphenyl)-6-(dimethylamino)-3H-xanthen-3-ylidene)-N-methyl-methanaminium Chloride (190)

To the stirred solution of carboxylic acid 128 (0.043 g, 0.079 mmol) and DIEA (0.041 mL, 0.23 mmol) in 1 mL of dry DMF bromomethyl acetate (0.023 mL, 0.23 mmol) was added. The resulting solution was kept at rt for 2 hrs and then diluted with 90 mL of chloroform. The solution was washed with water (5×20 mL), brine (30 mL), filtered through the paper filter and evaporated. The residue was re-evaporated with chloroform-toluene mixture and then re-dissolved in 2 mL of chloroform. The solution was diluted with 50 mL of ether and the resulting precipitate was collected on glass-fritted funnel. The product was washed with ether and dried in vacuo to provide AM ester 190 as a dark purple solid (0.0187 g, 36%).

Fluorimetric pH-Titration of the Sensor Molecules

Example 201. Fluorimetric pH Titration

The study of the fluorescent response of the sensor molecules to changes in pH was performed in solution in aqueous buffers (in concentrations around 10 µmol/L). The results of the titration are listed in Table 3.

Figure 2:
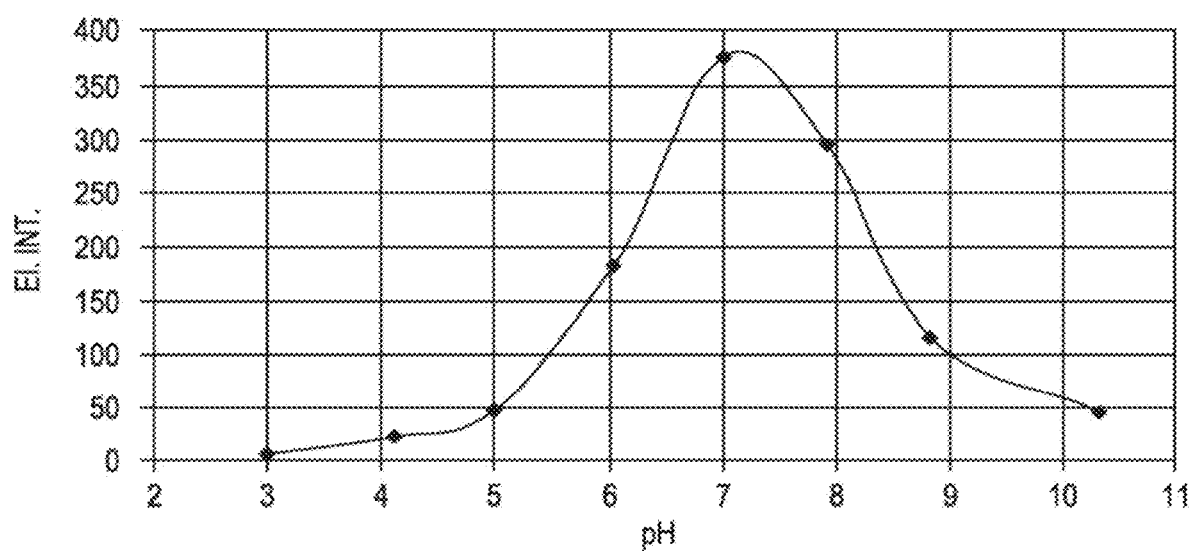
FIG. 2 shows the titration curve of the compound 173 having both amidine and fluorescein indicator groups, which resembles the fluorescein titration curve (increase in fluorescence with pKa about 5.5) and amidine titration curve (drop in fluorescence with pKa around 8.0). The resulting curve has a pronounced maximum at pH 7.2.

The titration curve of the compound 173 having both amidine and fluorescein indicator groups resemble the superposition of the fluorescein titration curve (increase in fluorescence with pKa about 5.5) and amidine titration curve (drop in fluorescence with pKa around 8.0). The resulting curve has a pronounced maximum at pH 7.2 (FIG. 2).

TABLE 3

Fluorescent response of the sensor molecules to the pH changes

| Compound | $\lambda_{ex}$, nm | $\lambda_{em}$, nm | pK | S = F/F$_0$ |
|---|---|---|---|---|
| 109 | 557 | 588 | 5.3 | 120 |
| 127 | 561 | 587 | 7.3 | 130 |
| 133 | 561 | 587 | 7.3 | 180 |
| 139 | 556 | 588 | 5.6 | 80 |
| 141 | 560 | 588 | 7.4 | 65 |
| 151 | 347 | 442 | 2.4; 6.6 | 6; 100 |
| 152 | 325 | 393 | 2.4; 7.2 | 30; 10 |
| 155 | 586 | 611 | 5.0 | 53 |
| 157 | 349 | 424 | 5.4 | 270 |
| 158 | 490 | 515 | 5.0 | 700 |
| 162 | 587 | 611 | 7.2 | 88 |
| 163 | 490 | 515 | 7.7 | 100 |
| 173 | 490 | 517 | 7.2 | 200 |
| 175 | 550 | 576 | 7.7 | 10 |

Example 202. Quantum Yield Determination

Quantum yields at pH=2.0 and pH=10.0 were determined for the compounds 178 and 179 relative to the pH-insensitive standard 180 by comparing integrated absorption and emission spectral curves.

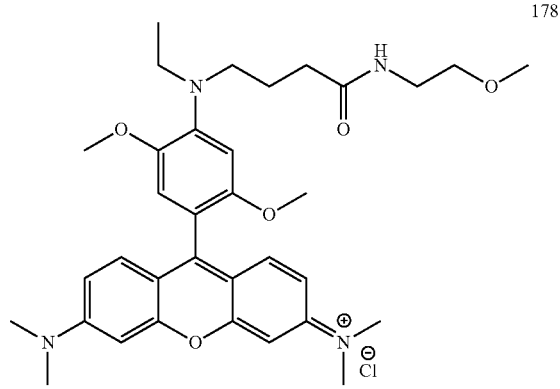

178

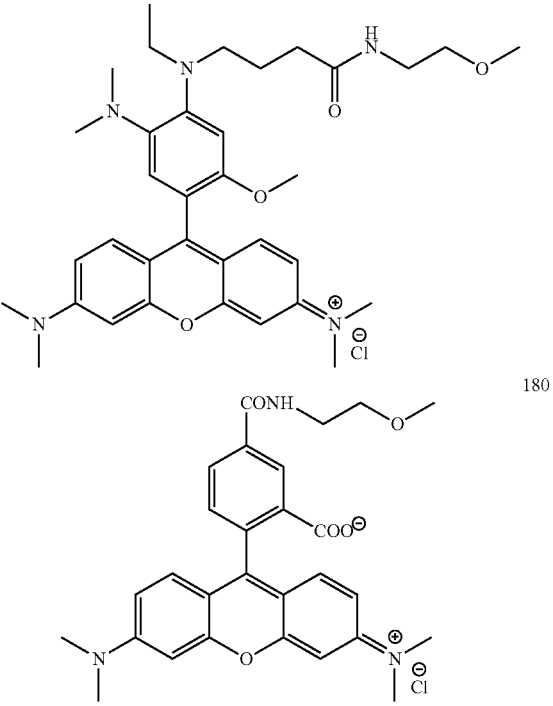

179

180

Compounds 178 and 179 were prepared by treatment of the corresponding succinimidyl esters 111 and 129 with methoxyethylamine. The reference standard 180 was obtained in the reaction of commercial succinimidyl 5-carboxy-tetramethylpdodamine (TAMRA-5-SE) with the same amine. The results are listed in table 4.

TABLE 4

Relative quantum yields of the pH sensors at low and high pH values

| Compound | pKa | QE (pH = 2.0) | QE (pH = 10.0) |
|---|---|---|---|
| 178 | 4.6 | 0.78 | 0.008 |
| 179 | 7.0 | 0.63 | 0.009 |

Biological Applications of pH Sensor Molecules

Example 301

The fluorogenic nature of the novel pH indicators described herein makes them very useful for studying a variety of internalization processes that occur in cells such as phagocytosis and endocytosis. This is because upon internalization there is a drop in pH inside the phagosome or endosome which results in an increase in fluorescence from the pH indicator. Conjugation of the pH sensor to biomolecules of interest provide for convenient assays of internalization of these molecules. Examples include transferrin, egf, ldl for studying receptor mediated endocytosis and labeled bioparticles such a *E. coli, Staphylococcus*, and zymosan for studying phagocytosis. Assays using these fluorogenic bioconjugates offer significant advantage over existing techniques due to the fact that the indicator is relatively non-fluorescent at the neutral pH outside the cell. This reduces or eliminates the need for wash steps and quencher dyes normally needed to reduce background signal from bioconjugates outside of the cells.

Labeling of Transferrin with pH Sensing Dyes.

All materials are from Invitrogen unless otherwise stated. Dissolve transferrin from human serum (Sigma, T4132) in 0.1 M NaHCO3, pH 8.3, to a concentration of 10 mg/mL. Make a 10 mg/mL solution of the succinimidyl ester of the dye in dry DMSO and sonicate briefly to aid in dissolution of the dye. Add a 10 to 30-fold molar excess of the reactive dye solution to the transferrin solution dropwise while stirring. Note that the volume of dye added depends on the specific dye and the amount of transferrin to be labeled. Protect the reaction vessel from light and stir for 1 hour at RT. Purify the conjugate on a P-30M gel filtration column (BioRad, 150-4150) in PBS, pH 7.2. Centrifuge the conjugate at 19,000 rpm for 20 minutes to remove aggregates, if present. Determine the degree of labeling by measuring A560 nm/A280 nm.

TABLE 5

Results

| Labeling Sensor | Mol. ratio | DOL | pKa | S = $F/F_0$ |
|---|---|---|---|---|
| 120 | 20 | 2.3 | 5.0 | |
| 129 | 10 | 1.0 | 4.2 | |
| 137 | 15 | 2.0 | 4.0 | |
| 139 | 30 | 6.0 | 4.6 | 15 |
| 168 | 30 | 7.0 | 6.4 | 100 |
| 171 | 20 | 9.0 | 2.8 | 13 |

Staining of Endocytic Recycling Compartment Using Transferrin Conjugated with pH Sensing Dye (Compound 129).

Figure 3:
FIG. 3 shows the perinuclear staining pattern of the endocytic recycling compartment of HeLa cells after incubation with transferrin conjugated to compound 111.

HeLa (ATCC) cells were plated in a 96 well microplate at 10,000 cells per well in McCoy 5A media with 5% FBS and 4 uM deferoxamine (Sigma). Cells were grown overnight and then rinsed 2 times in DMEM with-out phenol red plus 0.5% FBS. Transferrin conjugates were applied in same media at 20 ug/mL for 45 minutes at 37 C. Cells were then rinsed 1 time with DMEM and imaged on a Zeiss 200M inverted fluorescence microscope using a 40× objective, TRITC filters, a CoolSnap HQ (Photometrics) ccd camera, and Metamorph (Universal Imaging Corp.) acquisition software. FIG. 3 shows the characteristic perinuclear staining pattern of the endocytic recycling compartment.

Example 303: Labeling E. Coli Bioparticles for Use in Assays of Phagocytosis

*Escherichia coli* Strain K12, lyophilized cells (Sigma, EC1-5G) were resuspended in PBS at 20 mg/mL and vortexed vigorously and sonicated for several minutes. The suspensions were divided into 100 uL aliquots spun down at 10,000×g for 2 minutes, supernatants removed and resuspended in 100 uL of PBS. This was done twice to clean up the E. coli. The amine reactive SE versions of the novel pH dyes were made up in DMSO at concentration of 10 mM. For labeling, 100 uL of the E. coli suspension was combined with 100 uL of the dye stock solution, so 2 mg of E. coli was labeled with 1 umole of dye. The labeling was carried out at 37 C for 45 minutes followed by the same spin down and resuspension procedure as described above 5 times to remove free dye. The final resuspension was 10 mg/mL. pH Titration of Labeled E. Coli.

Figure 4:
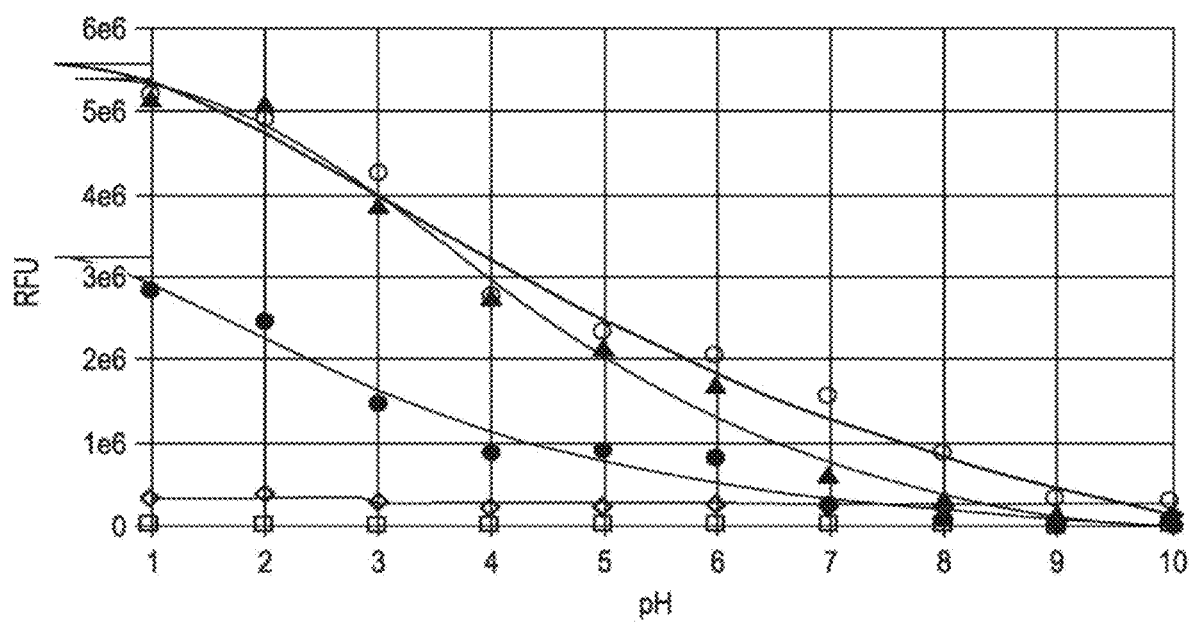
FIG. 4 shows fluorescence intensity measurements versus pH for pH dye labeled (compound 111 and compound 129) bioparticles and compares them to tetramethylrhodamine labeled bioparticles and unlabeled bioparticles. The dye-conjugates show a large increase in fluorescence at acidic pHs. The symbol (○) corresponds to compound number 129. The symbol (Δ) corresponds to compound 111. The symbol (◇) corresponds to tetramethylrhodamine. The symbol (•) corresponds to compound 189. The symbol (□) corresponds to a negative control.

The fluorescence of the labeled *E. coli* was measured at a range of pH values in 50 mM potassium phosphate buffer, from pH 1 to 10, using a Flexstation II (Molecular Devices) plate reader. The conjugates were diluted 1:50 into the potassium phosphate buffers, so the final concentration of the labeled bioparticles was 0.2 mg/mL. FIG. 4 shows the fluorescence intensity measurements versus pH for 3 novel pH dye labeled bioparticles and compares them to tetramethylrhodamine labeled bioparticles and unlabeled bioparticles. The dyes show a large increase in fluorescence at acidic pHs.

Assay of Phagocytic Activity Using Bioparticles Labeled with pH Sensing Dyes.

Figure 5A:
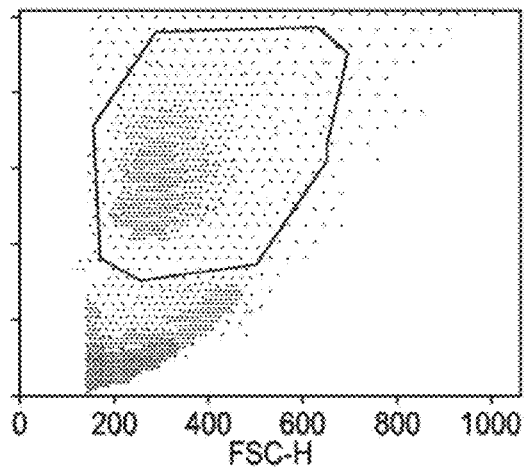
FIGS. 5A, 5B and 5C show a flow cytometry experiment indicating an increase in fluorescence of white blood cells (granualcytes) that have taken up the labeled (with compound 129) E. coli relative to unlabeled E. coli and compared with the iced negative control sample.
Figure 5A:
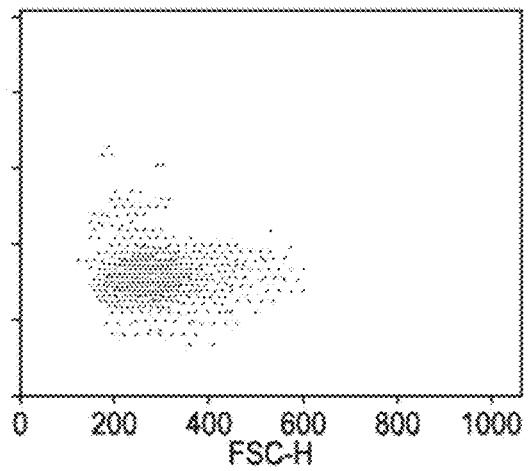
Figure 5B:
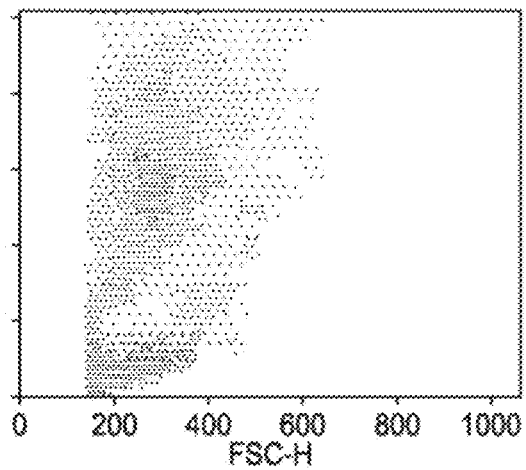
Figure 5B:
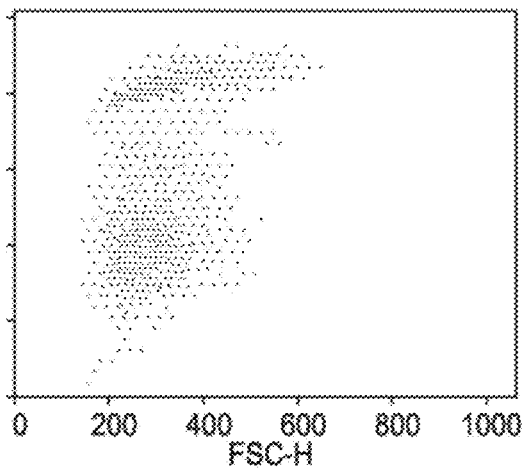
Figure 5C:
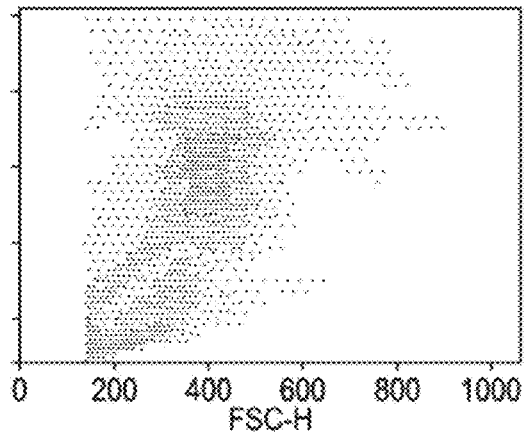
Figure 5C:
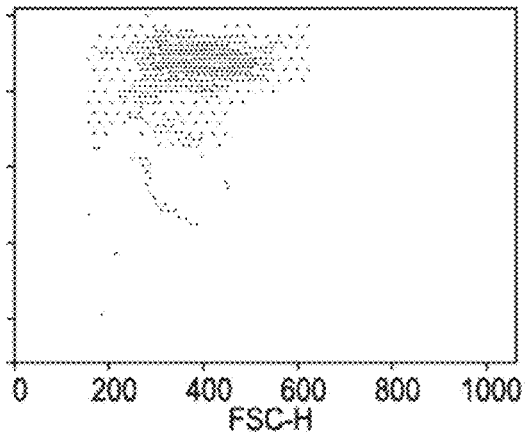

A whole blood sample was collected in a sodium heparin tube. Aliquots of whole blood (100 uL) were combined with labeled *E. coli* (20 uL of 10 mg/mL) in 12×75 mm flow cytometry Falcon tube, and the samples were incubated in a 37° C. water bath for 15 minutes. A negative control was put on ice. After incubation, the tubes were placed in a rack and the red blood cells were lysed with 1 mL of an ammonium chloride lysis solution (0.187 M NH4Cl, 10 mM KHCO3, 0.095 mM EDTA) for 10 minutes at room temperature. The samples were centrifuged at 1200 rcf for 5 minutes, the supernatants were removed, and the cell pellets were resuspended in HBSS buffer. The resuspended cells were put into a 96 well microplate, 100 uL per well, and the plate was spun to settle the cells to the bottom of the wells. Imaging was done on a Zeiss 200M inverted fluorescence microscope using a 40× objective, TRITC filters, a CoolSnap HQ (Photometrics) ccd camera, and Metamorph (Universal Imaging Corp.) acquisition software. FIGS. 5A, 5B and 5C show a flow cytometry experiment indicating an increase in fluorescence relative to the iced negative control sample. FIGS. 6A and 6B show the bright vesicular staining of the phagosomes filled with the engulfed *E. coli* within the cells. The left panel shows the staining found with the pH sensitive dye (compound 129). On the right TMR labeled *E. coli* were used and since they are fluorescent outside the cell you see the smaller dots of the *E. coli* that have not been engulfed. This would give an overestimation of phagocytic activity in a plate reader experiment, unless other steps were taken such as including a quencher dye.

Example 304: C16 Chain to Localize pH Sensor to Membrane

Figure 7A:
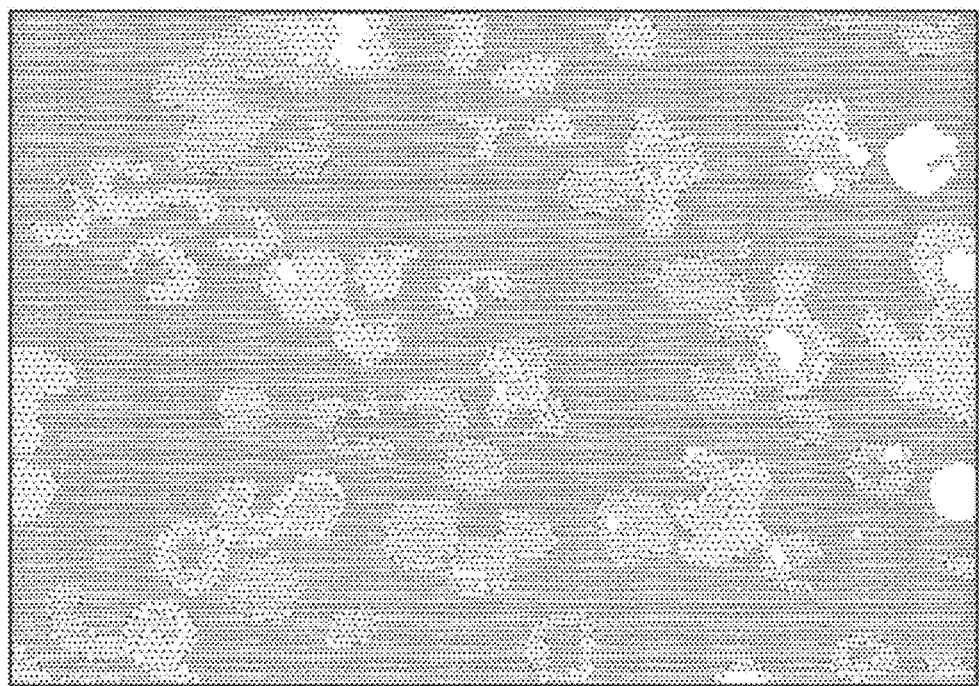
FIG. 7A shows that the C16 version of compound 109 labels the cells.
Figure 7B:
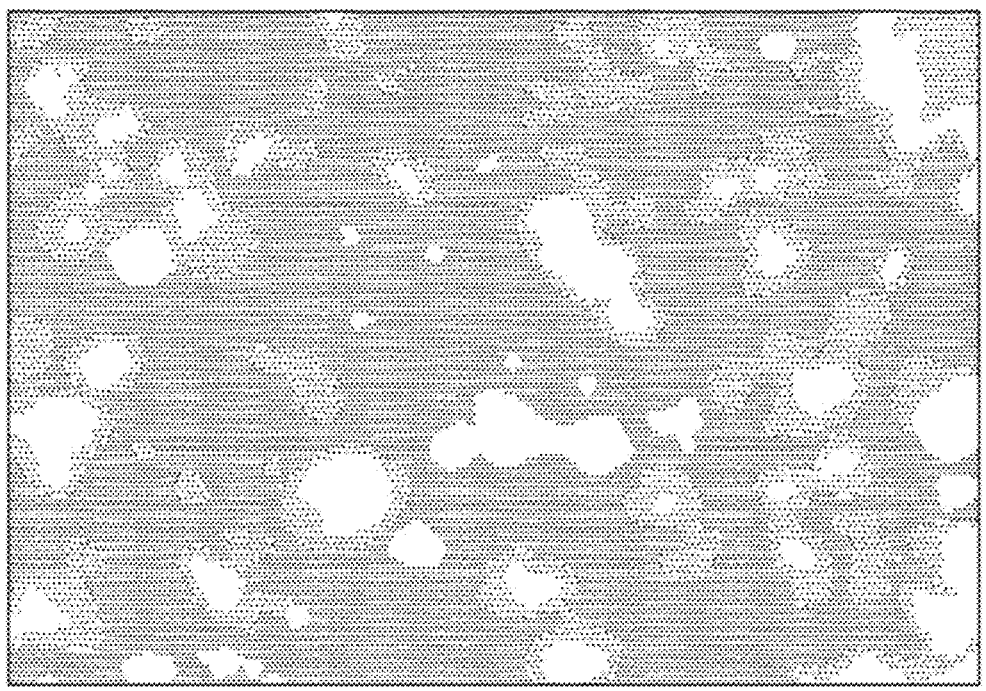
FIG. 7B shows the increase in signal of the membrane stain after it is internalized into acidic vesicles upon addition of un-labeled E. coli.
Figure 8A:
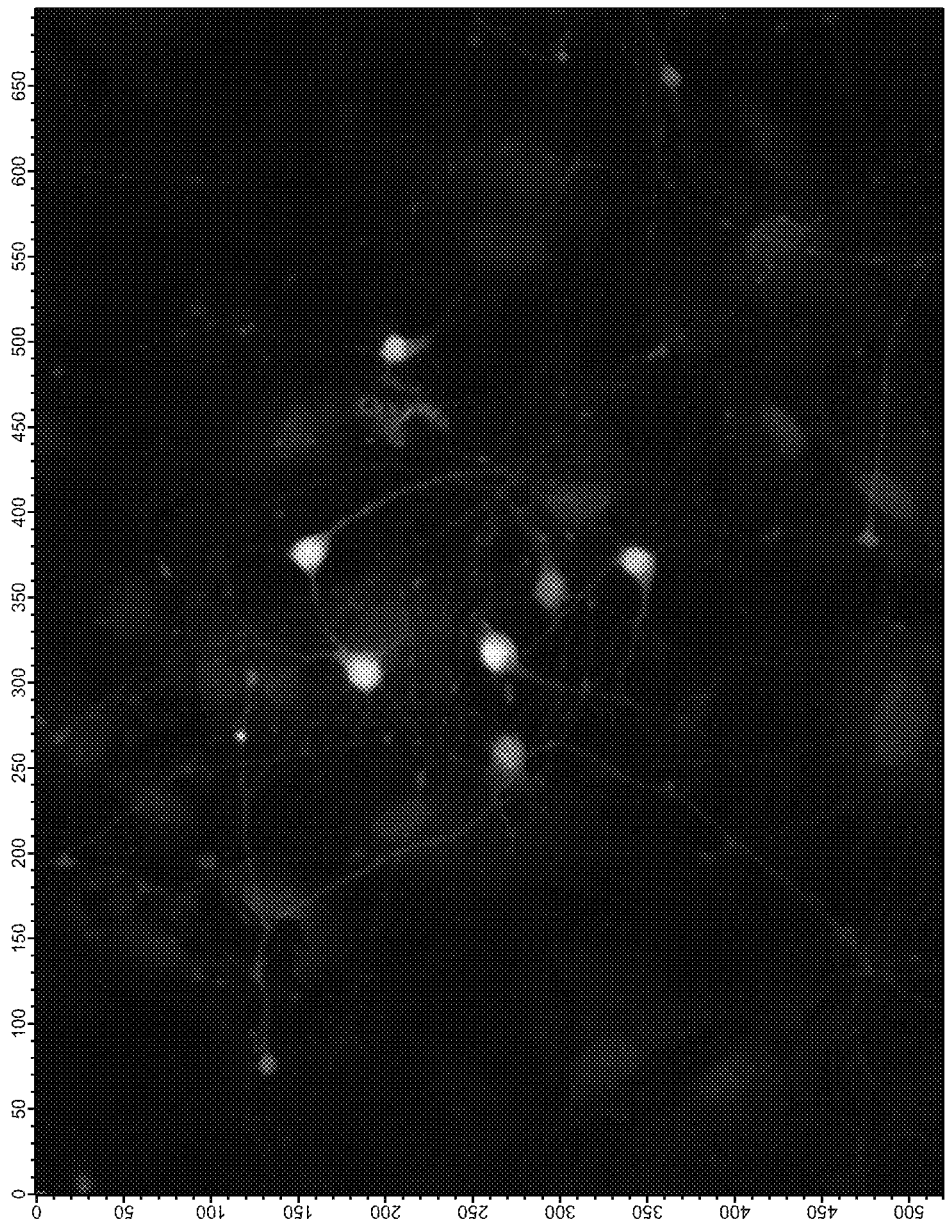
FIGS. 8A and 8B show the succinimidyl ester form of the dye specifically staining the neurons in the mixed cell culture. The low intensity image (FIG. 8A) shows very specific staining of the neurons in this preparation. The high intensity image (FIG. 8B) shows specific staining of the neurons as well as the relatively faint staining of the glial cells that form the feeder layer for the neurons in this mixed culture.
Figure 8B:
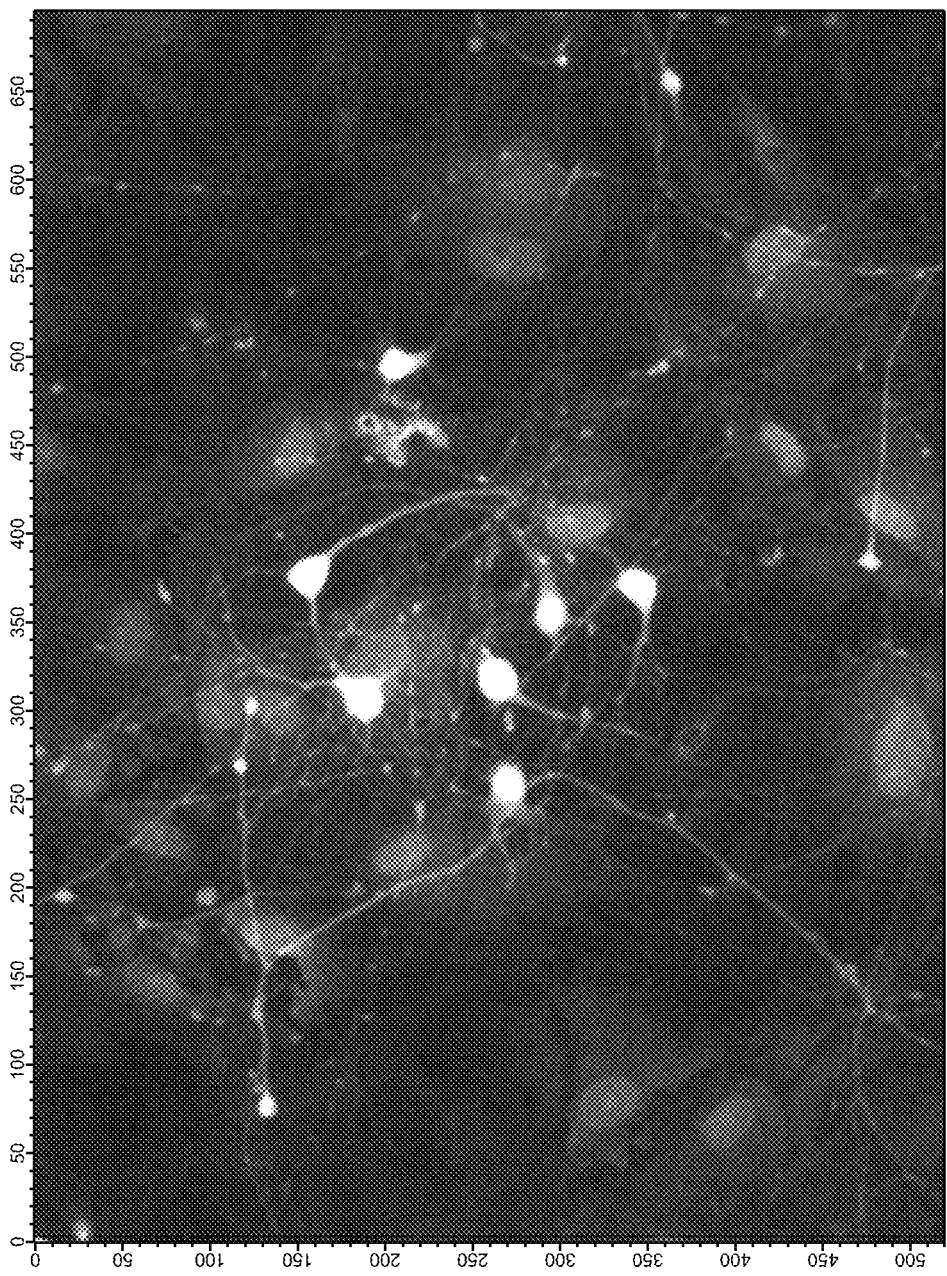
Figure 9A:
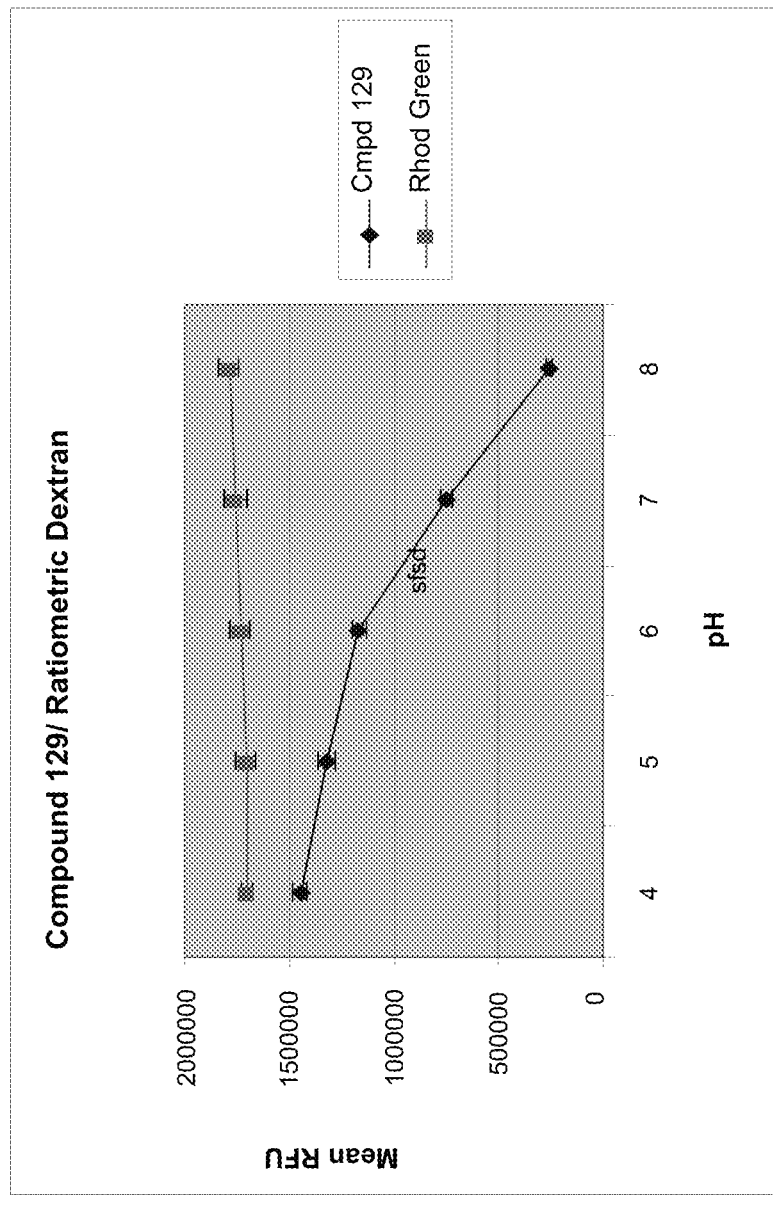
FIG. 9A shows the fluorescence responses from ratiometric dextran conjugates with rhodamine green at a higher degree of label than Compound 129. The conjugate was diluted at 0.1 mg/mL in 50 mM phosphate buffers that were prepared and adjusted to the indicated pH values, and then scanned on a fluorometric plate reader to determine the fluorescence from 1) rhodamine green (excites at 488, emits at 525, cutoff 515) does not change with pH, and 2) compound 129 in the red channel (ex 540, em 600 cutoff 590), whose fluorescence does change with pH.
Figure 9B:
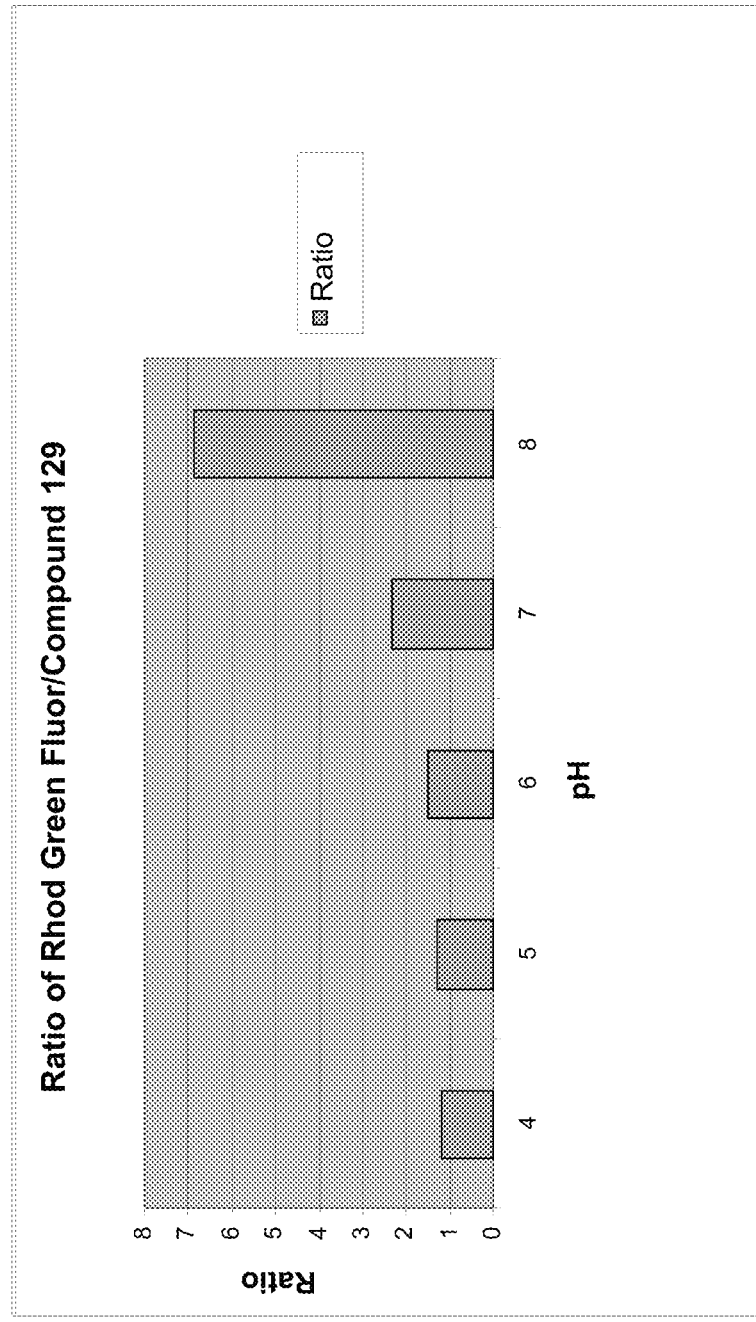
FIG. 9B shows bar graphs of the plots in FIG. 9A depicting the ratio of rhodamine green fluorescence/Compound 129 fluorescence for the two different constructs, across the pH range from 4 to 8.
Figure 10A:
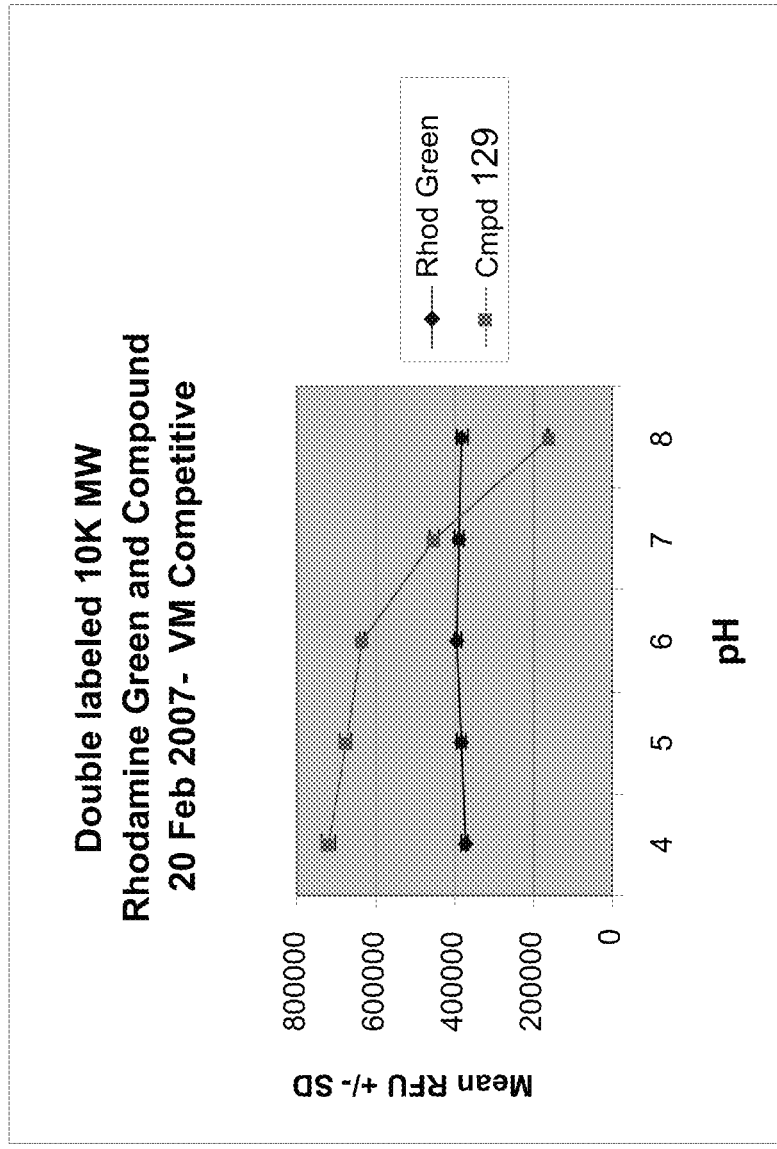
FIG. 10A shows fluorescence responses from 10,000 MW dextran conjugate. The conjugate was diluted at 0.1 mg/mL in 50 mM phosphate buffers that were prepared and adjusted to the indicated pH values, and then scanned on a fluorometric plate reader to determine the fluorescence from 1) rhodamine green (excites at 488, emits at 525, cutoff 515) does not change with pH, and 2 compound 129 in the red channel (ex 540, em 600 cutoff 590), whose fluorescence does change with pH.
Figure 10B:
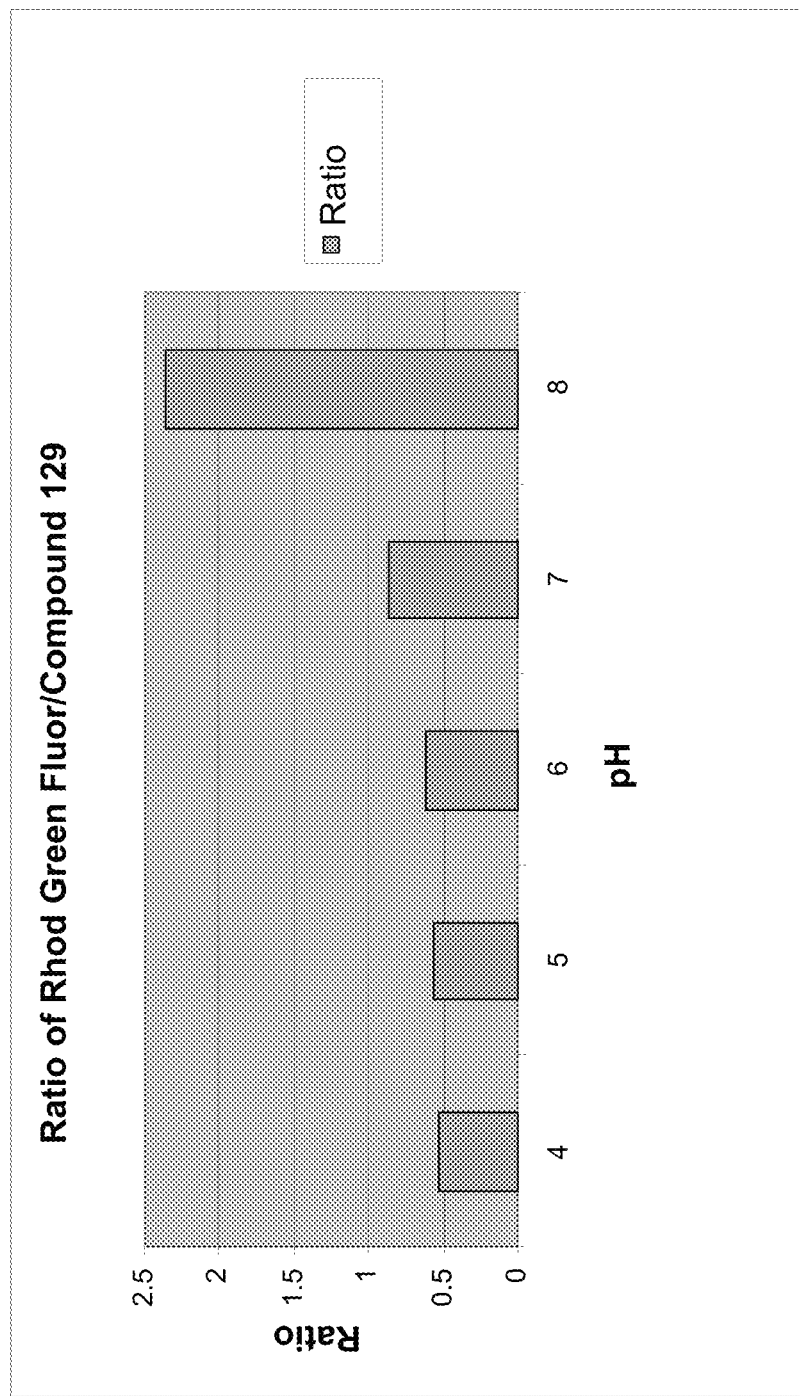
FIG. 10B shows bar graphs of the plots in FIG. 10A depicting the ratio of rhodamine green fluorescence/compound 129 fluorescence for the two different constructs, across the pH range from 4 to 8.
Figure 11A:
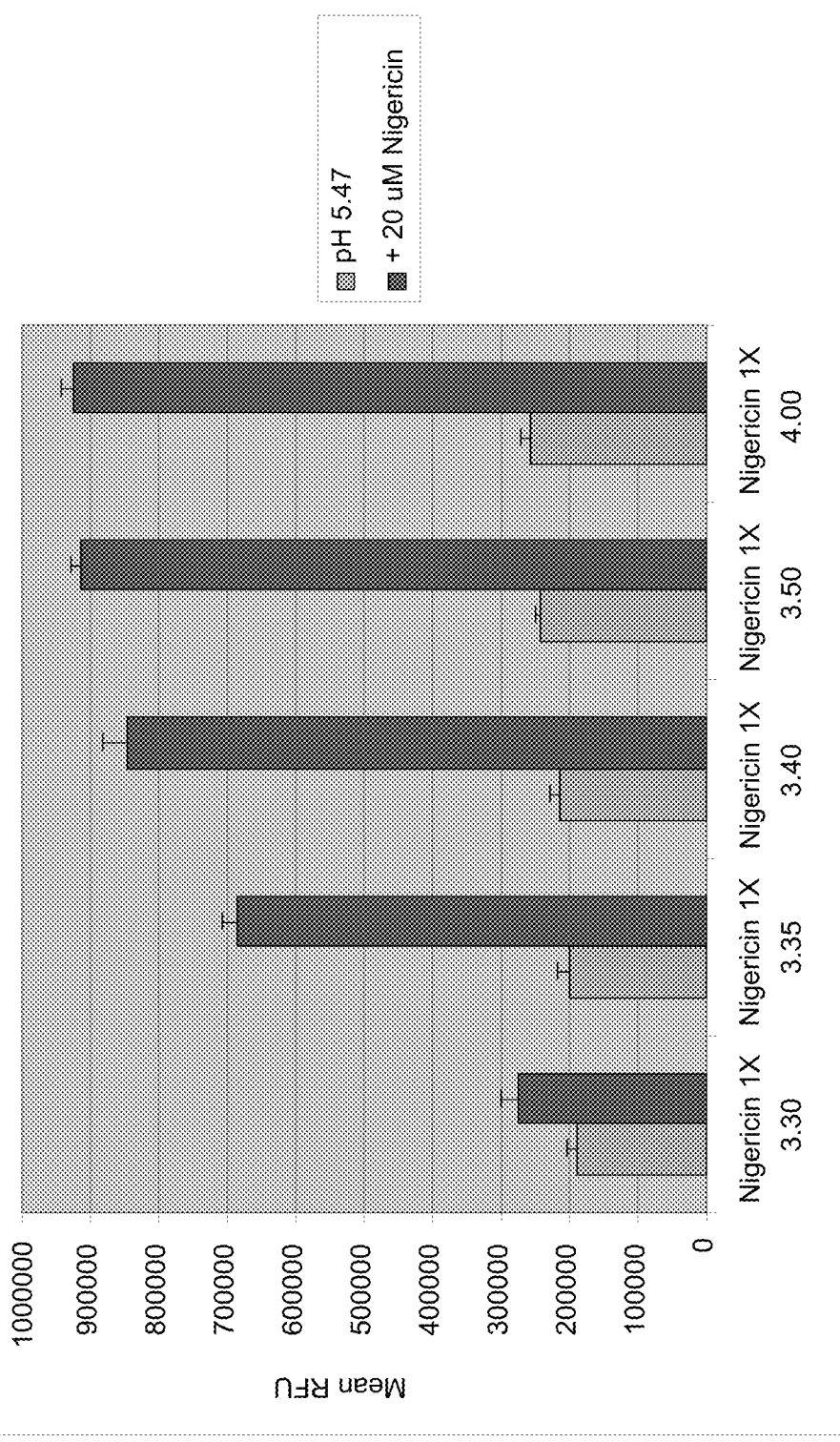
FIGS. 11A, 11B, 11C and 11D show the fluorescence output of a dye in solutions of varying extracellular pH, with the signal calibrated to specific pH values. Cells were incubated with compound 190 to load the cytosolic compartment at 5 uM in saline solution, and incubated with the cells for 30 minutes at 37 degrees, and 30 minutes at room temp. The cells are washed once with normal saline, and then treated with high potassium saline, plus or minus nigericin, at varying pH. The nigericin is a proton/potassium exchanger that uses the elevated potassium in the solution (it is substituted for sodium) to carry protons across the membrane until the cytosolic pH matches the pH of the extracellular solution.
Figure 11B:
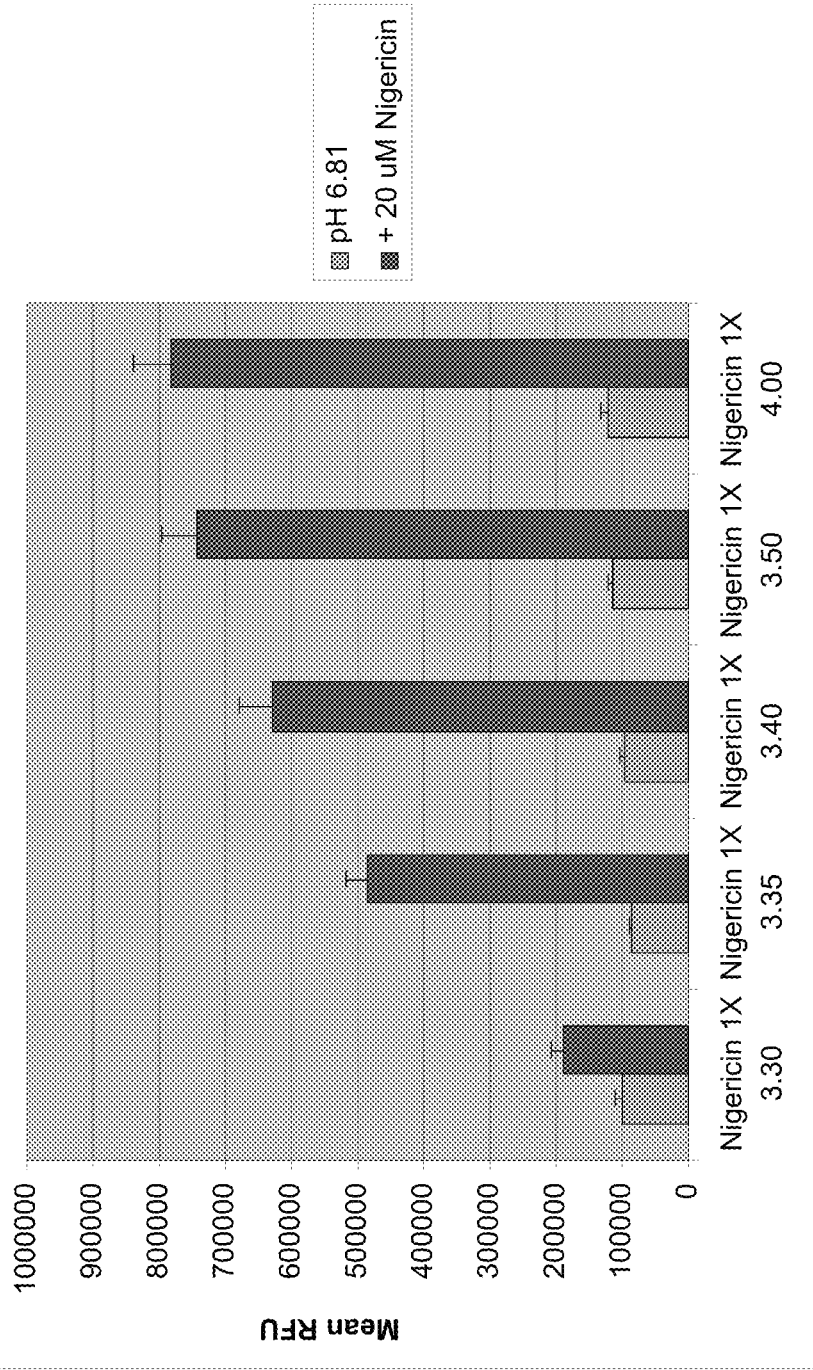
Figure 11C:
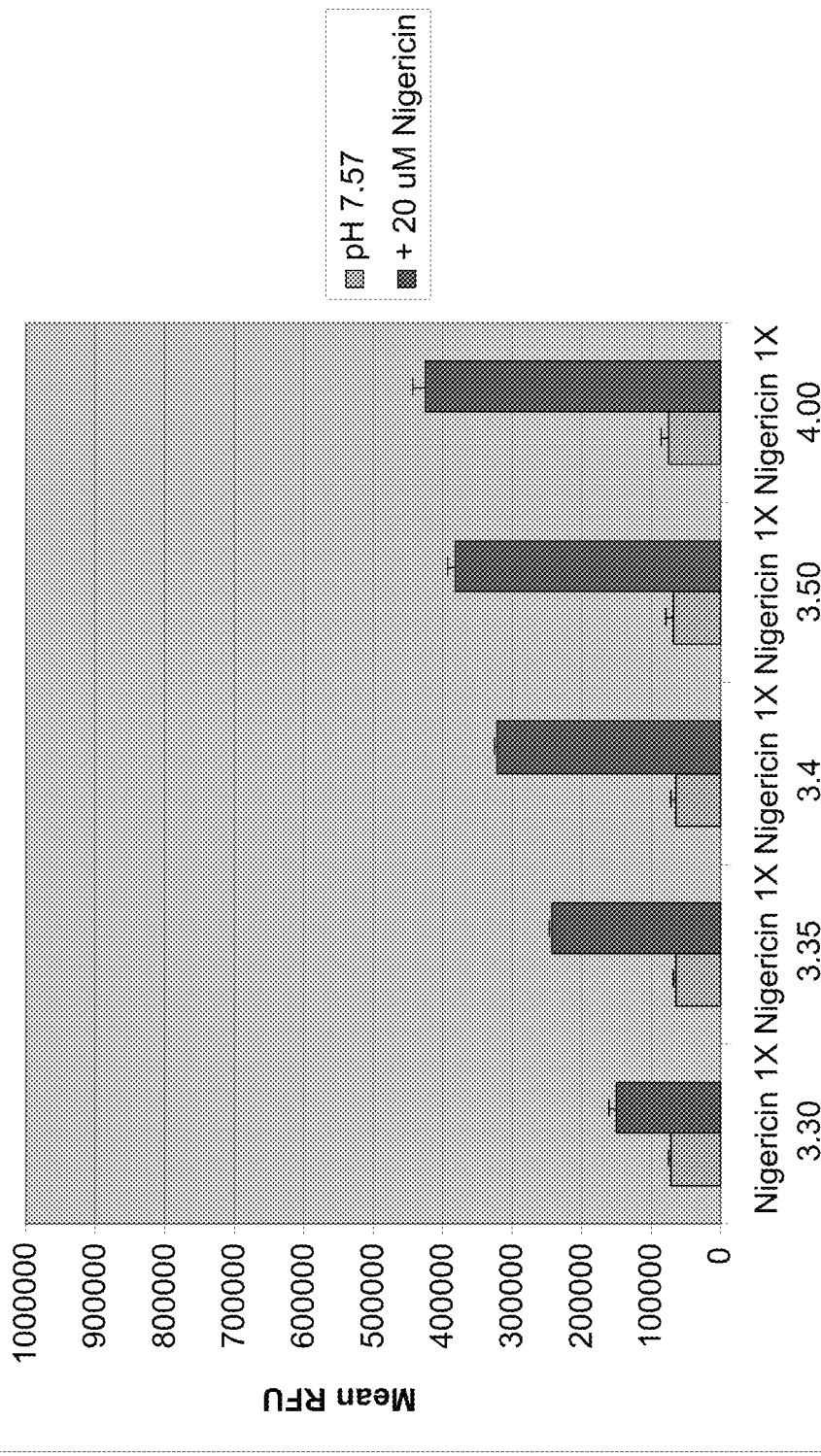
Figure 11D:
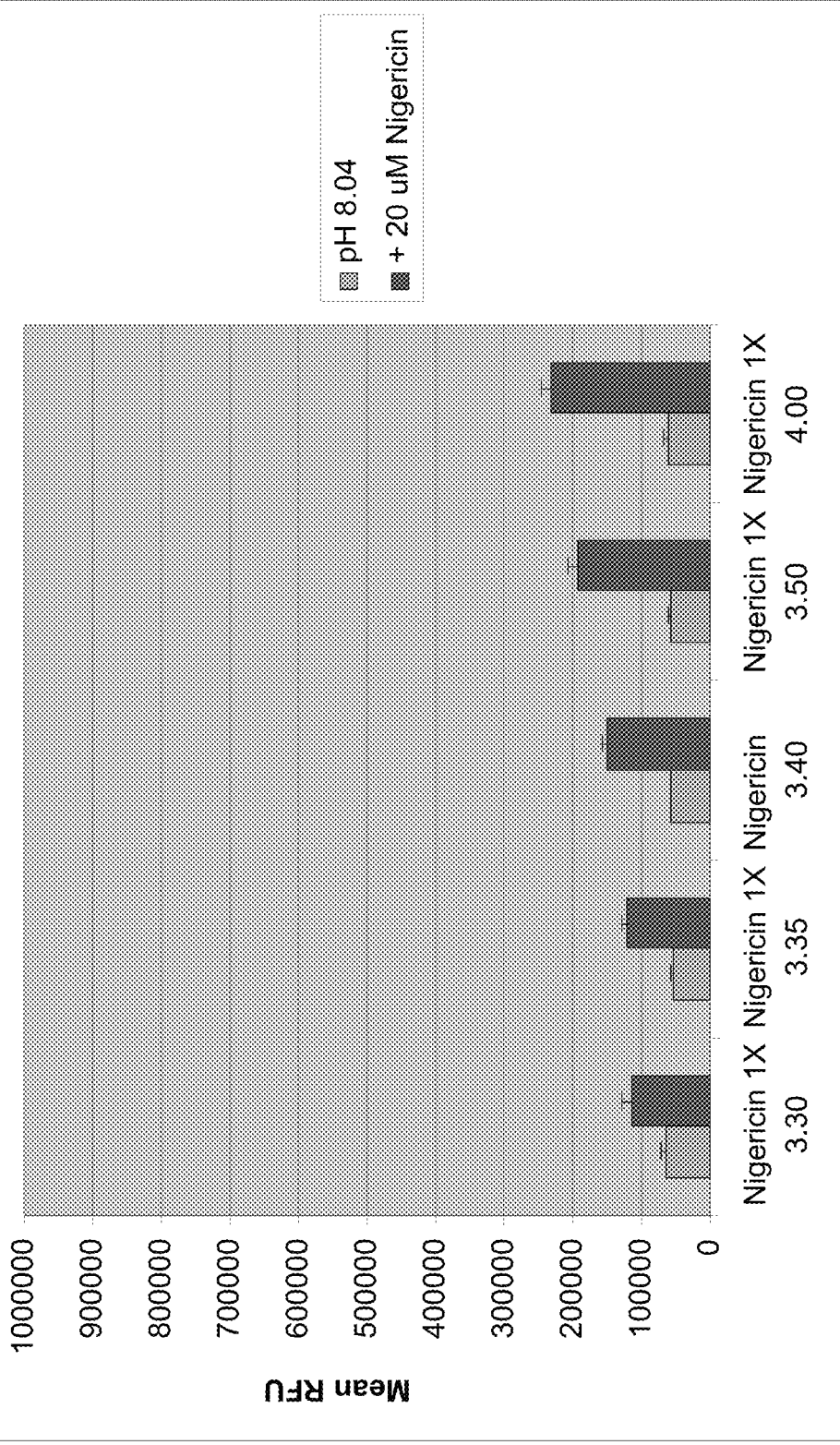
Figure 12B:
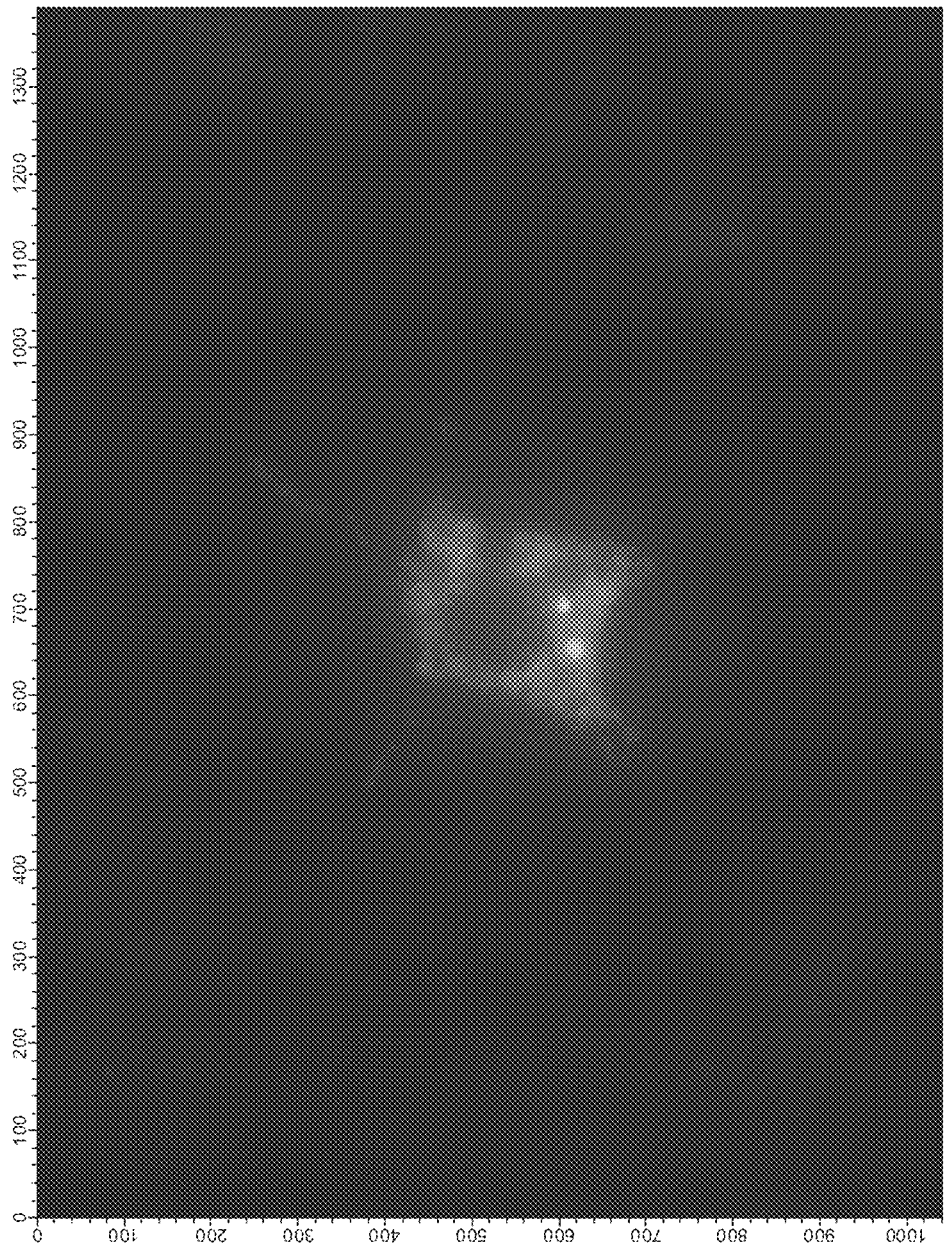

A more general label of the membrane may provide a passive mechanism for monitoring a variety of internalization events. As the membrane invaginates and forms vesicular compartments, the dye should follow and upon acidification show an increase in fluorescence. A c16 version of compound 129 was incubated with J774.2 cells at 10 uM at RT for 20 minutes and then visualized on a Zeiss 200M inverted fluorescence microscope using a 40× objective, TRITC filters, a CoolSnap HQ (Photometrics) ccd camera, and Metamorph (Universal Imaging Corp.) acquisition software. FIG. 7A shows that the dye labels the cells, and 7B shows the increase in signal of the membrane stain after it is internalized into acidic vesicles upon addition of un-labeled *E. coli*.

Example 305: Monitoring Cytosolic Acidification Associated with Ion Channel or Transporter Activation A cytosolically localized version of the pH sensitive dye should be a useful indication of proton influx through ion channels or transporters. This could be used for screening of antagonists, agonists, and other modulators of channel/transporter function.

Example 306: Receptor Internalization Assay

The β-2-Adrenergic Receptor (β2AR) is modified to incorporate an epitope tag (VSV-G tag YTDIEMNRLGK) at the N-terminus. A clonal, stable HEK 293 cell line is established which expresses this receptor (approximately 1.8 pmoles/mg cell homogenate). Anti-VSV-G antibody labeled with a compound described herein is used to monitor agonist-mediated receptor internalization in these live cells. The assay is performed in the presence and absence of a specific agonist, isoproterenol.

Isoproterenol-Induced Receptor Internalization in VSV-G-B2 Adrenergic Cells.

For HEK 293 cells it is preferable to coat plates with poly-D-lysine (Sigma P-6407, 5 mg in 50 ml sterile PBS) prior to seeding the cells. 30-80 µl/well is added and maintained at room temperature for 45 minutes. The coating solution is then aspirated, wash 4× (or more) with 100 µl sterile PBS. Plates can be treated in advance and stored at 4° C. for up to a week (with the final PBS wash still in the wells). Cultured cells can be seeded directly into the wells without first drying the plates. Cultured cells are diluted to ~1.6×10$^5$ cells/ml in complete MEM media (Sigma M2279) containing 200 µg/ml G418. 100 µl of cell suspension is pipetted into each assay well of a poly-D-lysine treated 96-well Packard Viewplate (cell density=16000 cells per well). Plates are then incubated 24-48 hours at 37° C. with 5% CO2. 250 µg lyophilized compound labeled anti-VSV-G antibody (PA45407) is reconstituted with 0.5 ml sterile deionized water and mixed thoroughly (stock concentration 0.5 mg/ml). The mixture is centrifuged to remove any precipitate. The compound labeled anti-VSV-G antibody is further diluted to a concentration of 2.5-5 µg/ml using serum-free, phenol red free MEM media. Hoechst 33342 nuclear stain can be added to the 2.5-5 µg/ml antibody solution to a final concentration of 5 µM. Media is subsequently removed from the cells and 100 µl antibody and Hoechst solution is added to each well. The solution is then incubated at room temperature for 15 minutes. 3 µM working dilution of isoproterenol agonist (from 10 mM stock in sterile water; Sigma 15627) is added to the solution and then 50 µl is added to required wells, giving 1 uM final concentration. The wells are incubated at 37° C. for 30 minutes (in a CO2 incubator or on the IN Cell Analyzer 3000). The cells are imaged on either an IN Cell Analyzer 3000, IN Cell Analyzer 1000 or a confocal microscope.

Internalization of Compound-Labeled Anti-VSV-G Antibody.

HEK 293 cells expressing a VSV-G-32-Adrenergic Receptor are preincubated with anti-VSV-G antibody-compound conjugate and stimulated with 1 µM isoproterenol. The cells are imaged using an IN Cell Analyzer 1000. Quantification of the agonist-mediated response is achieved using a granularity algorithm, which defines grains as distinct focal regions within a cell that have pronounced intensity differences from the region of the cell immediately surrounding the grains. The operator can adjust a variety of parameters to control what size and intensity of grain will be counted and analyzed.

Internalization of Compound-Labeled Anti-VSV-G Antibody.

HEK VSV-G-32-Adrenergic Receptor cells are preincubated with compound labeled anti-VSV-G antibody and increasing concentrations of isoproterenol (0-1 µM) are then added to the cells. After 30 minutes at 37° C., agonist mediated internalization is analysed by measuring the increase in compound fluorescence using the IN Cell Analyzer 1000 and the granularity analysis algorithm.

Example 307: Detection of Neuronal Cells with a Present Compound

Astroglial feeder layers were established for one week in culture on glass bottomed culture dishes, 35 mm diameter, coated with Poly-L-Lysine. Neurons from embryonic day 18 rat hippocampi were dissociated in culture medium, and seeded onto the feeder layers at a density of 25-35,000 cells per milliliter, two milliliters per dish, and allowed to grow in neuronal culture medium plus mitotic inhibitors to prevent glial proliferation.

Cells were pre-stained for 15 minutes with 200 ng/mL Hoercsht to visualize DNA in the nuclei, and 50 ng/mL calcien AM ester to visualize cytoplasm by adding 1000× DMSO stocks of these compounds to the cells in complete medium, then returning them to the cell culture incubator for fifteen minutes at 37 degrees celcius. Cells were removed, and the medium gently poured off. The cells were immediately placed in 5 uM Compound 129, diluted from a 1 mM DMSO stock into normal saline plus 20 mM HEPES and 20 mM glucose, final pH set to 7.4 with NaOH. The cells were incubated in labeling solution for ten minutes at room temperature, and then gently washed twice with saline (above) minus dye for imaging.

Neurons labeled with Compound 129 appear bright over the dimly labeled astrocytes in the TRITC channel, owing to the higher metabolic levels and consequently acidic pH of neurons relative to the feeder cells. Labeling with calcien AM shows a slightly brighter signal in the neurons than the glia, but this is due to the relative thickness of the neuronal cell bodies sitting on top of the flat glial feeder layer. The neuronal processes, less than 0.5 uM thick, demonstrate specificity of the present compounds because they are nearly invisible in calcein, but show up very clearly with the present compounds.

Acidification of the preparation shows that the glial cells had in fact taken up Compound 129 but that due to the pH were not visible.

Example 308: Phagocytosis of Betal Amyloid Conjugates 1 mg of beta amyloid 1-42 was purchased from California Peptide, #641-15, and labeled with Compound 129 to yield Compound 129-beta amyloid conjugate, which was purified by gel filtration to yield a solution of approximately 200 ng/mL with a degree of labeling between 1 and 2 dye molecules per beta amyloid molecule.

2 mL of J774A.1 cells were seeded onto 35 mm, poly-D-lysine coated glass bottom culture dishes at a density of 35,000 cells per mL one day in advance of the study, in serum-free OptiMem culture medium. Compound 129 beta amyloid conjugate was filtered through a 0.2 micron syringe filter, and 20 microliters of the solution was added to the cells. The culture was returned to the incubator (37 degrees celcius, 5% CO2) for overnight incubation, and imaged on the following day.

The representative brightfield image on the left shows several J774A.1 macrophage cells in a 40× field of view on the day of data collection. Imaging was done on a Zeiss Axiovert 200M microscope using MetaMorph™ imaging software. Cells were imaged in the same medium that they were labeled in, without removal of the compound 129 beta amyloid conjugate from the medium. The fluorescence image on the right was collected from the same field of view, using a standard TRITC filter set with a 200 millisecond exposure and shows labeling of one of the macrophages with the compound 129 beta amyloid conjugate, which was phagocytosed by the cell and compartmentalized into acidic phagosomes.

The label of a single cell in the field indicates that 1) compound 129 beta amyloid fed to macrophages results in a specific label, and no residual, free compound 129 succinimidyl ester dye remained in the solution from the amyloid labeling reaction. Free dye would have labeled all of the cells in the culture nonspecifically. 2) Compound 129 beta amyloid present outside of the cells in solution is not visible at the neutral pH of the culture medium, while phagocytosed compound 129 labeled beta amyloid is brightly labeled, giving a specific and high fidelity indicator of the uptake and acidification of compound 129 beta amyloid by the macrophages. 3) The fluorescence is coming from inside of the cells and not the cell surface, giving a specific label of internalization. Previous measurements of the phagocytosis of fluorescently labeled beta amyloid (FITC labeled) resulted in a combination of intracellular and extracellular surface labeling of the conjugate, confounding attempts to measure specific internalization and phagocytosis of beta amyloid by flow cytometry (Fiala et al., Journal of Alzheimer's Disease 7 (2005) 221-232; Zhang et al Journal of Alzheimer's Disease 10 (2006) 1-71 IOS Press, supra). Compound 129 beta amyloid labeled cells should therefore be visible in flow cytometry. J774A.1 macrophages labeled to a similar degree with Compound 129 *E coli* bioparticles conjugate were easily identified and quantified by flow cytometry in previous demonstrations, See Example 303.

What is claimed is:

1. A method for determining the pH of a sample, the method comprising:
   (a) contacting the sample with a compound of Formula I:

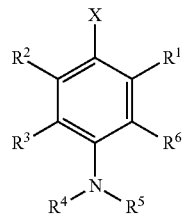

I wherein,
   $R^1$ and $R^2$ are each independently H, Z, or an electron donating group (EDG), provided that $R^1$ and $R^2$ are not hydroxyl or thiol or their deprotonated forms;
   $R^3$ and $R^6$ are each independently H, Z, or an electron donating group (EDG);
   EDG is selected from the group consisting of alkyl, substituted alkyl, alkenyl, substituted alkenyl, aryl, substituted aryl, cycloalkyl, substituted alkyl, heterocyclyl, substituted heterocyclyl, heteroaryl, and substituted heteroaryl;
   $R^4$ is selected from the group consisting of H, alkyl, substituted alkyl, acyl, aryl, substituted aryl, heteroaryl, substituted heteroaryl, cycloalkyl, substituted cycloalkyl, a reactive group, a carrier molecule, heterocyclyl, and substituted heterocyclyl;
   $R^5$ is independently selected from the group consisting of Y, alkyl, substituted alkyl, alkenyl, substituted alkenyl, acyl, aryl, substituted aryl, heteroaryl, substituted heteroaryl, cycloalkyl, substituted cycloalkyl, a reactive group, a carrier molecule, heterocyclyl, and substituted heterocyclyl;
   X is a fluorophore;
   Y is =$CR^bR^c$ or =$CR^bR^d$;
   Z is —$OR^c$, —$SR^c$, —$NR^bR^c$;
   $R^b$ is H, alkyl, or substituted alkyl;
   $R^c$ is alkyl or substituted alkyl; and
   $R^d$ is amino or substituted amino, to form a contacted sample;
   (b) incubating the contacted sample to form an incubated sample;
   (c) illuminating the incubated sample to form an illuminated sample; and
   (d) detecting fluorescent emissions from the illuminated sample;
   wherein the fluorescent emissions are used to determine the pH of the sample.

2. The method of claim 1, wherein the sample comprises cells, intracellular fluids, extracellular fluids, sera, biological fluids, biological fermentation media, environmental sample, industrial samples, proteins, peptides, buffer solutions, chemical reactors, blood cells, immune cells, cultured cells, muscle tissue, neurons, extracellular vesicles, vascular tissue, blood fluids, saliva, urine, water, soil, waste water, sea water, pharmaceuticals, foodstuffs or beverages.

3. The method of claim 2, wherein the sample is immobilized on a polymeric membrane, within a polymeric gel, on a microparticle, on a microarray, on a silicon chip, on a glass slide, on a microwell plate, or on a microfluidic chip.

4. The method of claim 3, wherein the contacting step further comprises contacting the sample with a second dye.

5. The method of claim 4, wherein the second dye is a pH sensitive dye having a different fluorescent emission spectrum from the dye or compound and a different pKa from the pKa of the compound.

6. The method of claim 2, wherein the cells are live cells and the incubating comprises the compound entering the cell to form a labeled cell.

7. The method of claim 1, wherein X is a xanthene, an indole or a borapolyazaindacine.

8. The method of claim 1, wherein X is:

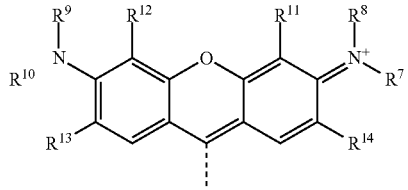

wherein,
   $R^7$, $R^8$, $R^9$ and $R^{10}$ are each independently selected from the group consisting of alkyl, substituted alkyl, aryl, substituted aryl, heteroaryl, substituted heteroaryl, cycloalkyl, substituted cycloalkyl, heterocyclyl, and substituted heterocyclyl; and
   $R^{11}$, $R^{12}$, $R^{13}$ and $R^{14}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester) oxy, cyano, halo, hydroxyl, nitro, —$SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or $R^{11}$ and $R^{14}$ are taken together with $R^7$ and $R^8$ to form a fused ring; and $R^{12}$ and $R^{13}$ are taken together with $R^9$ and $R^{19}$ to form a fused ring.

\* \* \* \* \*

UNITED STATES PATENT AND TRADEMARK OFFICE
CERTIFICATE OF CORRECTION

PATENT NO. : 10,845,373 B2  
APPLICATION NO. : 15/899021  
DATED : November 24, 2020  
INVENTOR(S) : Jeffrey Dzubay et al.

Page 1 of 1

It is certified that error appears in the above-identified patent and that said Letters Patent is hereby corrected as shown below:

On the Title Page

In Column 1, delete "(60) Division" and insert --(62) Division--, therefor.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*